US010590397B2

(12) United States Patent
Rayment et al.

(10) Patent No.: US 10,590,397 B2
(45) Date of Patent: Mar. 17, 2020

(54) MUTANT UDP-GLYCOSYLTRANSFERASE VARIANTS OF OS79 OR HOMOLOGS THEREOF FOR T-2 TOXIN INACTIVATION

(71) Applicant: Wisconsin Alumni Research Foundation, Madison, WI (US)

(72) Inventors: Ivan Rayment, Fitchburg, WI (US); Karl Wetterhorn, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/910,717

(22) Filed: Mar. 2, 2018

(65) Prior Publication Data

US 2018/0346921 A1 Dec. 6, 2018

Related U.S. Application Data

(60) Provisional application No. 62/470,726, filed on Mar. 13, 2017.

(51) Int. Cl.
*C12N 9/10* (2006.01)
*C12N 15/82* (2006.01)

(52) U.S. Cl.
CPC ....... *C12N 9/1051* (2013.01); *C12N 15/8282* (2013.01); *C12Y 204/00* (2013.01)

(58) Field of Classification Search
None
See application file for complete search history.

(56) References Cited

PUBLICATIONS

Wetterhorn et al. Crystal structure of Os79 (Os04g0206600) from *Oryza sativa*: a UDP-glucosyltransferase involved in the detoxification of deoxynivalenol. (2016) Biochemistry; vol. 55; pp. 6175-6186 (Year: 2016).*
Li et al. Transgenic wheat expressing a barley UDP-glucosyltransferase detoxifies deoxynivalenol and provides high levels of resistance to Fusarium graminearum. (2015) MPMI; vol. 28; pp. 1237-1246 (Year: 2015).*
Poppenberger et al. Detoxification of the Fusarium mycotoxin deoxynivalenol by a UDP-glucosyltransferase from *Arabidopsis thaliana*. (2003) J. of Biological Chemistry; vol. 278; pp. 47905-47914 (Year: 2003).*
Woo et al. DNA-free genome editing in plants with preassembled CRISPR-Cas9 ribonucleoproteins. (2015) Nature Biotechnology; vol. 33; pp. 1162-1165 (Year: 2015).*
Chivian, D., et al., "Prediction of CASP6 Structures Using Automated Robetta Protocols," Proteins 61, Suppl. 7:157-66, 2005.
Delano, W.L., PyMOL: An Open-Source Molecular Graphics Tool, 2002, Delano Scientific, Palo Alto, CA, USA; <https://www.pymol.org/>.
Gardiner, S.A., et al.; "Transcriptome Analysis of the Bariey-deoxynivalenol Interaction: Evidence for a Role of Glutathione in Deoxynivalenol Detoxification," Molecular Plant-Microbe Interactions (MPMI) 23(7):962-976, 2010.
Grove; J.F., "The Trichothecenes and Their Biosynthesis," Chem. Org. Naturst. 86:63-130, 2007.
Lairson, L.L., et al., "Glycosyltransferases: Structures, Functions, and Mechanisms," Annual Review of Biochemistry 77:521-555, 2008.
Lemmens, M., et al., "The Ability to Detoxify the Mycotoxin Doxynivalenol Colocalizes with a Major Quantitative Trait Locus for Fusarium Head Blight Resistance in Wheat," Molecular Plant-Microbe Interactions 18(12):1318-1324, 2005.
Li, X., et al., "Transgenic Wheat Expressing a Barley UDP-glucosyltransferase Detoxifies Doxynivalenol and Provides High Levels of Resistance to Fusarium graminearum," Molecular Plant-Microbe Interactions 28(11):1237-1246, 2015.
McCormick; S.P., et al., "Trichothecenes: From Simple to Complex Mycotoxins," Toxins 3(7):802-614, 2011.
Michlmayr, H., et al., "Biochemical Characterization of a Recombinant UDP-glucosyltransferase from Rice and Enzymatic Production of Deoxynivalenol-3-O-β-glucoside," Toxins 7(7):2685-2700, 2015.
Muhitch, M.J., et al., "Transgenic Expression of the TRI101 or PDR5 Gene Increases Resistance of Tobacco to the Phytotoxic Effects of the Trichothecene 4, 15-diacetoxyscirpenol," Plant Science 157:201-207, 2000.
GenBank Accession No. XM_002447461, dated Jun. 13, 2017.
GenBank Accession No. GU170355, dated Jun. 23, 2011.
GenBank Accession No. XP_015635481, dated Aug. 7, 2018.
GenBank Accession No. NP_181215, dated Feb. 14, 2019.
GenBank Accession No. NP_181218, dated Feb. 14, 2019.
GenBank Accession No. 5TMB_A, dated Dec. 2, 2017.
GenBank Accession No. NP_181217, dated Feb. 14, 2019.
GenBank Accession No. XP_003581017, dated Mar. 27, 2017.
GenBank Accession No. XP_010239695, dated Mar. 27, 2018.
Poppenberger, B., et al., "Detoxification of the Fusarium Mycotoxin Deoxynivalenol by a UDP-glucosyltransferase from *Arabidopsis thaliana*," Journal of Biological Chemistry 278(48):593-601, 2003.
Proctor, R.H., et al., "Reduced Virulence of Gibberella zeae Caused by Disruption of a Trichothecene Toxin Biosynthetic Gene," Molecular Plant-Microbe Interaction 6(4):593-601, 1995.
Russell, R.B., et al., "Recognition of Analogous and Homologous Protein Folds: Analysis of Sequence and Structure Conservation," Journal of Molecular Biology 269(3):423-439, 1997.
Schweiger, W., et al., "Functional Characterization of two Clusters of Brachypodium distachyon UDP-glycosyltransferase Encoding Putative Deoxynivalenol Detoxification Genes," Molecular Plant-Microbe Interactions (MPMI) 26(7):781-792, 2013.
Schweiger, W., et al., "Validation of a Candidate Deoxynivalenol-inactivating UDP-glucosyltransferase from Barley by Heterologous Expression in Yeast," Molecular Plant-Microbe Interactions (MPMI) 23(7):977-986, 2010.

(Continued)

*Primary Examiner* — Cathy Kingdon Worley
(74) *Attorney, Agent, or Firm* — Dentons US LLP

(57) ABSTRACT

Compositions and methods for increasing resistance to *Fusarium* infection in plants are provided herein. Polynucleotides, polypeptides, and expression constructs for expressing mutant UDP-glycosyltransferase proteins, plants comprising the polynucleotides, polypeptides or expression constructs, and methods of producing transgenic plants are also provided.

31 Claims, 3 Drawing Sheets
Specification includes a Sequence Listing.

(56) References Cited

PUBLICATIONS

Van Den Ent, F., and Lowe, J., "RF Cloning: A Restriction-Free Method for Inserting Target Genes into Plasmids," Journal of Biochemical and Biophysics Methods 67(1):67-74, 2006.

Wetterhorn, K.M., et al., "Crystal Structure of Os79 (Os04g0206600) from *Oryza sativa*: A UDP-glucosyltransferase Involved in the Detoxification of Deoxynivalenol," Biochemistry 55(44):6175-6186, 2016.

Winn, M.D., et al., "Overview of the CCP4 Suite and Current Developments," Acta Crystallographica Section D Biological Crystallography 67(pt 4):235-242, 2011.

Wu, Q., et al., "Trichothecenes: Structure-Toxic Activity Relationships," Current Drug Metabolism 14(6):641-660, 2013.

Yang, J., et al., "The I-TASSER Suite: Protein Structure and Function Prediction," Nature Methods 12(1):7-8, 2015.

\* cited by examiner

FIG. 2 (con't)

```
AT_73C4_+ve_Q9Z    395  LP..PCNQ.LVQYLKA..SAGVEEVMKWGEE..I..VD....KAVE..GAS.DAK
DOGT1_73C5_+ve_    394  L....FCNE.LVEVLKA..SGVEQPMKWGEE..I..VD....KFAVE..GES.DAK
AT_73C6_UGT_+we    394  L....FCNE.LVQILK...SAEVKEVMKWGEE..I..VD....KFAVE..GES.DAK
Brad15g02780.1_    383  .....DPTA.YVESA..GVRY---------NRDNE.V.-R..EEVERCI.EV.-...
Os_79_+ve_XP_01    382  .ADPTI..YVE....GVR.----------QL.G..P-QR.EVERCI.EV.-....
Sb06g002180_wea    386  .ADPTI..YVESI..IGVRY---------RKDEK.C.-T.EVERCI.EV.-...
Brad15g03300.1_    384  .ADPTIA.YVESANDMGVR.----------KSLN..R-R..EEVERCI.EV.-...
HvUGT13248_BarI    390  .ADOPTIA.YVES.WG.GVEA---------RKN.N.C.-K..EEVERCI.EV.-...

AT_73C4_+ve_Q9Z    455  ..RVKELGES.RK..EGGS.RS..TYLLQDIMQQVKSKN          (SEQ ID NO:24)
DOGT1_73C5_+ve_    454  ...KELGDS.RK..EGGS.RS..SPLLQDIMELAEPNN          (SEQ ID NO:26)
AT_73C6_UGT_+we    454  ...KELGES.RK..EGGS.RS..TFLLQDIMQL-----          (SEQ ID NO:28)
Brad15g02780.1_    432  ....ARW..KAKEAMQEGGSSDKN.IAEPAA.YA.S-----        (SEQ ID NO:30)
Os_79_+ve_XP_01    431  ....TRL..KAKEMQEGGSSDKN.IAEPAA.K.------         (SEQ ID NO:2)
Sb06g002180_wea    435  ....TMW..KAKEAMQNGGSSSK.NVCEP.AK.SS-----        (SEQ ID NO:32)
Brad15g03300.1_    433  ....AKW..KAKETMBAGGSSNK..IAEPAAAKYS.S-----      (SEQ ID NO:34)
HvUGT13248_BarI    439  ....MNW..KAKEAMQEGGSSDK..AEP..KYSSI-----        (SEQ ID NO:20)
```

MUTANT UDP-GLYCOSYLTRANSFERASE VARIANTS OF OS79 OR HOMOLOGS THEREOF FOR T-2 TOXIN INACTIVATION

CROSS-REFERENCE TO RELATED APPLICATIONS

This application claims the priority of U.S. Provisional Appl. Ser. No. 62/470,726, filed Mar. 13, 2017, the entire disclosure of which is incorporated herein by reference.

STATEMENT REGARDING FEDERALLY SPONSORED RESEARCH OR DEVELOPMENT

This invention was made with government support under 59-0206-1-117 awarded by the USDA/ARS and 17-CRHF-0-6055 awarded by the USDA/NIFA. The government has certain rights in the invention.

FIELD OF THE INVENTION

The present disclosure relates to the field of biotechnology. More specifically, the disclosure relates to recombinant DNA molecules encoding proteins that inactivate T-2 toxin, as well as methods of producing T-2 toxin resistant plants and plants exhibiting increased T-2 toxin resistance.

INCORPORATION OF SEQUENCE LISTING

A sequence listing contained in the file named "WARF111US.txt" which is 106 kilobytes (measured in MS-Windows®) and created on Mar. 2, 2018, is filed electronically herewith and incorporated by reference in its entirety.

BACKGROUND

Agricultural crop production often utilizes novel traits created using the methods of biotechnology. A recombinant DNA molecule encoding a modified polypeptide can be introduced into a plant to produce a novel trait. Expression of the recombinant DNA molecule in the plant confers a trait, such as T-2 toxin resistance, to the plant.

SUMMARY OF THE INVENTION

The present disclosure provides a polynucleotide comprising a DNA sequence encoding a modified UDP-glycosyltransferase polypeptide, the polypeptide comprising at least a first mutation relative to a wild-type UDP-glycosyltransferase polypeptide, wherein mutation renders the modified UDP-glycosyltransferase polypeptide capable of glycosylating T-2 toxin, diacetoxyscirpenol (DAS), 4-acetyl-NIV (4-ANIV) and/or 4,15-diacetyl-NIV (4,15-di-ANIV) from *Fusarium*. In certain embodiments, the modified UDP-glycosyltransferase polypeptide comprises at least two mutations relative to a wild-type UDP-glycosyltransferase polypeptide. In particular embodiments the modified UDP glycosyltransferase polypeptide comprises a mutation at positions corresponding to amino acids 122 and 123 of SEQ ID NO:2. In some embodiments, the modified UDP glycosyltransferase polypeptide comprises the amino acid sequence of SEQ ID NO:4, SEQ ID NO:6 or SEQ ID NO:22. In other embodiments, the modified UDP-glycosyltransferase polypeptide comprises at least three mutations relative to a wild-type UDP-glycosyltransferase polypeptide. In yet other embodiments the modified UDP glycosyltransferase polypeptide comprises a mutation at positions corresponding to amino acids 122, 123 and 202 of SEQ ID NO:2. In further embodiments the modified UDP glycosyltransferase polypeptide comprises the amino acid sequence of SEQ ID NO:8 or SEQ ID NO:10.

In additional embodiments the polynucleotide is operably linked to a regulatory element. In various embodiments the regulatory element is a heterologous regulatory element. In certain embodiments the regulatory element is a promoter, for example a promoter that is functional in a plant or an inducible promoter.

The present disclosure further provides a polypeptide encoded by a polynucleotide comprising a DNA sequence encoding a modified UDP-glycosyltransferase polypeptide, the polypeptide comprising at least a first mutation relative to a wild-type UDP glycosyltransferase polypeptide, wherein mutation renders the modified UDP-glycosyltransferase polypeptide capable of glycosylating T-2 toxin from *Fusarium*. In certain embodiments the polynucleotide encodes the amino acid sequence of SEQ ID NO:4, SEQ ID NO:6, SEQ ID NO:8, SEQ ID NO:10, SEQ ID NO:12. SEQ ID NO:14, SEQ ID NO:16, SEQ ID NO:18, SEQ ID NO:20 or SEQ ID NO:22, or amino acid sequences comprising a T291V, T291S, Q202E, F199Q, Q143A, S203L or S203A mutation relative to wild-type Os79 (SEQ ID NO:2). In other embodiments the polynucleotide comprises the nucleic acid sequence of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 or SEQ ID NO:21, or nucleic acid sequences encoding a T291V, T291S, Q202E, F199Q, Q143A, S203L or S203A mutation relative to wild-type Os79 (SEQ ID NO:2).

The present disclosure also provides a plant, plant part, cell, or seed comprising a polynucleotide comprising a DNA sequence encoding a modified UDP-glycosyltransferase polypeptide, the polypeptide comprising at least a first mutation relative to a wild-type UDP glycosyltransferase polypeptide, wherein mutation renders the modified UDP-glycosyltransferase polypeptide capable of glycosylating T-2 toxin from *Fusarium*. In some embodiments the plant, plant part, cell, or seed is defined as a monocotyledonous plant, seed, cell, or plant part. In additional embodiments the monocotyledonous plant, seed, cell, or plant part is a corn, wheat, rice, barley, oats and *sorghum plant, seed, cell, or plant part*. In other embodiments the plant, plant part, cell, or seed is defined as a dicotyledonous plant, seed, cell, or plant part. In further embodiments the dicotyledonous plant, seed, cell, or plant part is a *soybean, alfalfa, sunflower, cotton, canola, sweet potato, tomato, banana, curcubits, peppers and sugar beet plant, seed, cell, or plant part*.

The present disclosure additionally provides a method of increasing the resistance of a plant to *Fusarium* infection, comprising expressing in the plant a polynucleotide comprising a DNA sequence encoding a modified UDP-glycosyltransferase polypeptide, the polypeptide comprising at least a first mutation relative to a wild-type UDP glycosyltransferase polypeptide, wherein mutation renders the modified UDP-glycosyltransferase polypeptide capable of glycosylating T-2 toxin from *Fusarium*. In various embodiments the plant is defined as a monocotyledonous plant or a dicotyledonous plant. In certain embodiments the method comprises transforming the plant with the polynucleotide and regenerating the plant therefrom. In other embodiments the method comprises crossing a parent plant comprising the polynucleotide with itself or a second plant to obtain the plant in which resistance to *Fusarium* infection is increased.

The present disclosure further provides a method of increasing the resistance of a plant to *Fusarium* infection, comprising modifying a UDP-glycosyltransferase polypeptide of the plant. In particular embodiments the modifying comprises mutating at least one amino acid of the UDP-glycosyltransferase polypeptide. In some embodiments the modifying comprises site-specific mutagenesis. In certain embodiments the site-specific mutagenesis comprises the use of single primer, zinc finger nucleases (ZFN), TALEN, or CRISPR technology.

BRIEF DESCRIPTION OF THE DRAWINGS

FIG. 1: Selected amino acid side chains and the secondary structural elements that carry them that define the active site architecture for the trichothecene binding site in Os79 (PDB accession number 5TMB). Members of the GT-B family of glucosyl transferase enzymes that exhibit activity towards DON will have an architecture (structure) that differs by less than an rms difference 2 Å for the structurally equivalent alpha carbon atoms surrounding the active site from this model and thus will contain residues equivalent to H122, L123, and Q202 (others) that can be mutated to yield activity towards T-2 toxin.

FIG. 2: Clustal alignment of the amino acid sequences for UDP-glucosyl transferase 73C6 from *Arabidopsis thaliana* (AT_73C6_UGT_+we; SEQ ID NO:28), DON-glucosyltransferase 1 from *Arabidopsis thaliana* (DOGT1_73C5_+ve; SEQ ID NO:26), UDP-glycosyltransferase superfamily protein from *Arabidopsis thaliana* (AT_73C4_+ve_Q9Z; SEQ ID NO:24), predicted crocetin glucosyltransferase 2-like isoform X1 from *Brachypodium distachyon* (Bradi5g02780.1 ; SEQ ID NO:30), Os79 (Os_79_+ve_XP_01; SEQ ID NO:2), hypothetical protein from *Sorghum bicolor* (sorghum) (Sb06g002180_wea; SEQ ID NO:32), predicted UDP-glycosyltransferase 74E2-like from *Brachypodium distachyon* (Bradi5g03300.1 ; SEQ ID NO:34), and *Hordeum vulgare* subsp. vulgare UDP-glucosyltransferase HvUGT13248 from *Hordeum vulgare* subsp. vulgare (domesticated barley; SEQ ID NO:20).

BRIEF DESCRIPTION OF THE SEQUENCES

SEQ ID NO:1: Os79 Codon Optimized DNA Sequence.
SEQ ID NO:2: Os79 WT Protein Sequence.
SEQ ID NO:3: Os79 H122A/L123G DNA Sequence.
SEQ ID NO:4: Os79 H122A/L123G Protein Sequence.
SEQ ID NO:5: Os79 H122A/L123A DNA Sequence.
SEQ ID NO:6: Os79 H122A/L123A Protein Sequence.
SEQ ID NO:7: Os79 H122A/L123A/Q202A DNA Sequence.
SEQ ID NO:8: Os79 H122A/L123A/Q202A Protein Sequence.
SEQ ID NO:9: Os79 H122A/L123A/Q202L DNA Sequence.
SEQ ID NO:10: Os79 H122A/L123A/Q202L Protein Sequence.
SEQ ID NO:11: Os79 Q202A DNA Sequence.
SEQ ID NO:12: Os79 Q202A Protein Sequence.
SEQ ID NO:13: Os79 Q202V DNA Sequence.
SEQ ID NO:14: Os79 Q202V Protein Sequence.
SEQ ID NO:15: Os79 Q202L DNA Sequence.
SEQ ID NO:16: Os79 Q202L Protein Sequence.
SEQ ID NO:17: Os79 A384S DNA Sequence.
SEQ ID NO:18: Os79 A384S Protein Sequence.
SEQ ID NO:19: HvUGT13248 WT DNA Sequence.
SEQ ID NO:20: HvUGT13248 WT Protein Sequence.
SEQ ID NO:21: HvUGT13248 H132A/L133A DNA Sequence.
SEQ ID NO:22: HvUGT13248 H132A/L133A Protein Sequence.
SEQ ID NO:23: AT_73C4_+ve_Q9Z DNA Sequence.
SEQ ID NO:24: AT_73C4_+ve_Q9Z Protein Sequence.
SEQ ID NO:25: DOGT1_73C5_+ve_DNA Sequence.
SEQ ID NO:26: DOGT1_73C5_+ve_Protein Sequence.
SEQ ID NO:27: AT_73C6_UGT_+we DNA Sequence.
SEQ ID NO:28: AT_73C6_UGT_+we Protein Sequence.
SEQ ID NO:29: Bradi5g02780.1_DNA Sequence.
SEQ ID NO:30: Bradi5g02780.1_Protein Sequence.
SEQ ID NO:31: Sb06g002180_wea DNA Sequence.
SEQ ID NO:32: Sb06g002180_wea Protein Sequence.
SEQ ID NO:33: Bradi5g03300.1_DNA Sequence.
SEQ ID NO:34: Bradi5g03300.1_Protein Sequence.
SEQ ID NO:35: Os79 forward primer.
SEQ ID NO:36: Os79 reverse primer.
SEQ ID NO:37: Os79: Q202A mutagenesis primer.
SEQ ID NO:38: Os79: Q202L mutagenesis primer.
SEQ ID NO:39: Os79: Q202V mutagenesis primer.
SEQ ID NO:40: Os79: A384S mutagenesis primer.
SEQ ID NO:41: Os79: H122A/L123A mutagenesis primer.
SEQ ID NO:42: Os79: H122A/L123G mutagenesis primer.
SEQ ID NO:43: HvUGT13248: H132A/L133A mutagenesis primer.
SEQ ID NO:44: HvUGT13248 forward primer.
SEQ ID NO:45: HvUGT13248 reverse primer.
SEQ ID NO:46: Os79 WT DNA Sequence.
SEQ ID NO:47: Os79: T291V mutagenesis primer.
SEQ ID NO:48: Os79: T291S mutagenesis primer.
SEQ ID NO:49: Os79: Q202E mutagenesis primer.
SEQ ID NO:50: Os79: F199Q mutagenesis primer.
SEQ ID NO:51: Os79: Q143A mutagenesis primer.
SEQ ID NO:52: Os79: S203L mutagenesis primer.
SEQ ID NO:53: Os79: S203A mutagenesis primer.

DETAILED DESCRIPTION

The present disclosure describes novel UDP-glycosyltransferase (UGT) polypeptides. The disclosed UGT polypeptides contain at least a first mutation compared to wild-type UGT, and in certain further embodiments comprise three mutations compared to wild-type UGT.

*Fusarium* head blight and *Fusarium* ear rot are devastating plant diseases that affect small grain cereals and maize on a global scale. Infection is caused by fungi of the genus *Fusarium*; members of the *Fusarium graminearum* species complex are the most prevalent agents (Starkey, et al., *Fungal Genet. Biol.* 44:1191-1204, 2007; van der Lee, et al., *Food Addit. Contam., Part A* 32:453-460, 2015). The trichothecene mycotoxins produced by these fungi are virulence factors and accumulate in the grain of infected plants. They are potent inhibitors of eukaryotic protein synthesis (Cundliffe, et al., *Proc. Natl. Acad. Sci. USA* 71:30-34, 1974), posing a significant threat to both animal and human consumers (Pestka, *Arch. Toxicol.* 84:663-679, 2010).

Trichothecene mycotoxins are a highly diverse group of tricyclic sesquiterpenoid epoxides (Evans, et al., *J. Chem. Soc., Chem. Commun.* 465a, 1973). More than 200 trichothecenes have been identified, all of which are characterized by a 12,13-epoxytrichothec-9-ene skeleton (McCormick, et al., *Toxins* 3:802-814, 2011; Grovey, *Chem. Org. Naturst.* 88:63-130, 2007). Variations in the substitution pattern of the trichothecene backbone exist in different producing organisms. *F. graminearum* synthesizes either deoxynivalenol (DON) and its acetylated derivatives, 3-acetyl-deoxynivalenol and 15-acetyl-deoxynivalenol, or nivalenol (NIV) and acetylated derivatives, while T-2 toxin and HT-2 toxin are produced by *Fusarium sporotrichioides* (McCormick, 2011, supra). Differences in substitution can have a dramatic effect on the toxicity to both plants and animals, and have important implications in developing resistance strategies (Anderson, et al., *J. Med. Chem.* 32:555-562, 1989).

Previous research has been directed at understanding the role of the trichothecene mycotoxins in plant infection. Most efforts have focused on DON because it is the most prevalent mycotoxin associated with *Fusarium* head blight (Kim, et al., *Mycol. Res.* 107:190-197, 2003; Larsen, et al., *Toxicol. Lett.* 153:1-22, 2004). There is strong evidence to suggest that DON is a virulence factor for plant pathogenesis (Proctor, et al., *Mol. Plant-Microbe Interact.* 8:593-601, 1995). Disruption of trichothecene biosynthesis by knocking out trichodiene synthase (tri5) led to *Fusarium* that were still capable of causing infection, however with decreased virulence in wheat and a decreased ability to spread from the infection site (Proctor, et al., 1995, supra; Jansen, et al., *Proc. Natl. Acad. Sci. USA* 102:16892-16897, 2005). The ability of DON to spread ahead of the fungus, causing bleaching and necrosis, is likely due to the inhibition of protein synthesis caused by the toxin and thereby facilitates the spread of infection in host tissue. As a result, DON resistance is considered an important component of *Fusarium* disease resistance (Lemmens, et al., *Mol. Plant-Microbe Interact.* 18:1318-1324, 2005).

One mechanism of DON resistance in plants is the ability to convert DON to deoxynivalenol 3-O-glucoside (D3G). It was shown that an increased ability to form D3G in hexaploid wheat was responsible for an increased resistance to both the bleaching effects of DON and fungal spreading (Lemmens, et al., 2005, supra). Additionally, transcriptome analysis of DON-treated barley revealed the upregulation of several UGTs in a genotype that was shown to convert DON to D3G (Gardiner, et al., *Mol. Plant-Microbe Interact.* 23:962-976, 2010). D3G has a significantly decreased ability to inhibit wheat ribosomes in vitro (Poppenberger, et al., *J. Biol. Chem.* 278:47905-47914, 2003). The first UGT capable of synthesizing D3G was cloned from *Arabidopsis thaliana* (DOGT1) and conferred increased tolerance to DON when constitutively overexpressed in *Arabidopsis* (Poppenberger, et al., 2003, supra). Interestingly, DOGT1 overexpression did not confer protection against nivalenol and was accompanied by a dwarfism phenotype associated with conversion of the brassinosteroid brassinolide to the inactive brassinolide 23-O-glucoside (Poppenberger, et al., *Appl. Environ. Microbiol.* 72:4404-4410, 2006). Subsequently, other UGT genes potentially associated with DON detoxification have been identified in *Arabidopsis*, wheat (Lulin, et al., *Mol. Biol. Rep.* 37:785-795, 2010), and barley (Gardiner, et al., 2010, supra). When tested for their ability to confer DON resistance in sensitized yeast, only one (HvUGT13248) of four DON-induced barley UGT genes and two of six *Arabidopsis* UGT genes showed protection (Schweiger, et al., *Mol. Plant-Microbe Interact.* 23:977-986, 2010). Expression of the barley UGT gene (HvUGT13248) in wheat provided reduction in incidence and severity of *Fusarium* head blight, without obvious morphological effects, but the response was variable (Li, et al., *Mol. Plant-Microbe Interact.* 28:1237-1246, 2015). This illustrates the difficulty in predicting which UGTs have the desired DON specificity among members of the very large gene family with 160-180 genes in diploid crop plants (Ross, et al., *Genome biology* 2, reviews 3004.1, 2001; Achnine, et al., *Plant J.* 41:875-887, 2005; Caputi, et al., *Plant J.* 69, 1030-1042, 2012). An additional problem is that the UGT genes are frequently located in gene clusters that seem to undergo rapid evolution, so that even highly similar genes in clusters have different substrate specificities (Schweiger, et al., *Mol. Plant-Microbe Interact.* 26:781-792, 2013). Furthermore, none of the described UGTs have been reported to be effective against T-2 toxin or diacetoxyscirpenol (DAS).

Importantly, the presently disclosed UGT polypeptides are capable of detoxifying T-2 toxin 4-acetyl-NIV (4-ANIV), 4,15-diacetyl-NIV (4,15-diANIV) and DAS, as well as DON, 15-acetyldeoxynivalenol (15-ADON), NIV, isotrichodermol (isoT) and HT-2. The present disclosure surprisingly provides variants of UGT that are able to detoxify a number of different toxins produced by *Fusarium* species, in addition to DON, and therefore provide a broader range of protection against and resistance to *Fusarium* infections. Initially, three amino acid positions in the wild-type UGT enzyme isolated from rice (Os79; nucleotide sequence SEQ ID NO:1; amino acid sequence SEQ ID NO:2) were targeted for mutagenesis. Changing the histidine residue at position 122 of Os79 to alanine, the leucine residue at position 123 of Os79 to alanine, and the glutamine residue at position 202 of Os79 to alanine resulted in a modified UGT (nucleotide sequence SEQ ID NO:7; amino acid sequence SEQ ID NO:8) that was capable of glycosylating not only DON, NIV, isoT and HT-2, but also T-2, 4-ANIV, 4,15-diANIV, and DAS. The following mutants also exhibited the ability to glycosylate T-2 toxin: Os79 Q202A (nucleotide sequence SEQ ID NO:11; amino acid sequence SEQ ID NO:12), Os79 Q202L (nucleotide sequence SEQ ID NO:15; amino acid sequence SEQ ID NO:16), Os79 Q202V (nucleotide sequence SEQ ID NO:13; amino acid sequence SEQ ID NO:14), Os79 H122A/L123G (nucleotide sequence SEQ ID NO:3; amino acid sequence SEQ ID NO:4), Os79 H122A/L123A (nucleotide sequence SEQ ID NO:5; amino acid sequence SEQ ID NO:6), and Os79 H122A/L123A/Q202L (nucleotide sequence SEQ ID NO:9; amino acid sequence SEQ ID NO:10). In addition, activity slightly above background was seen in Os79 A384S (nucleotide sequence SEQ ID NO:17; amino acid sequence SEQ ID NO:18). Some of the disclosed variants (for example Os79 A384S) have low activity that is only detectable by analyzing the samples for the glycosylated trichothecene product by LCMS.

The present disclosure therefore provides modified UGT polynucleotides and polypeptides that are capable of glycosylating, and therefore at least partially, or in certain embodiments completely, inactivating a range of toxins produced by different *Fusarium* species. The present disclosure thus also provides methods of producing plants with increased resistance to a variety of toxins produced by different *Fusarium* species, by providing a modified UGT polynucleotide or polypeptide, or by modifying a naturally-occurring UGT polynucleotide or polypeptide existing in a plant, as described in detail herein.

The disclosure therefore permits increases in crop performance, grain yield and quality. In view of increasing concerns regarding food shortages in various areas of the world, this represents a significant advance to agriculture and the art in general.

I. Recombinant DNA Molecules

As used herein, the term "nucleic acid" or "polynucleotide" refers to a single or double-stranded polymer of deoxyribonucleotide bases or ribonucleotide bases read from the 5' to the 3' end. A nucleic acid or polynucleotide may also optionally contain non-naturally occurring or altered nucleotide bases that permit correct read through by a polymerase and do not reduce expression of a polypeptide encoded by that nucleic acid. The terms "nucleotide sequence" or "nucleic acid sequence" refer to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA). The words "nucleic acid fragment," "nucleotide sequence fragment", or more generally "fragment" will be understood by those in the art as a functional term that includes genomic sequences, ribosomal RNA sequences, transfer RNA sequences, messenger RNA sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the present disclosure. The polynucleotide sequence includes both the sense and antisense strands either as individual strands or in the duplex.

As used herein, the term "recombinant nucleic acid," "recombinant polynucleotide" or "recombinant DNA molecule" refers to a polynucleotide that has been altered from its native state, such as by linkage to one or more other polynucleotide sequences to which the recombinant polynucleotide molecule is not normally linked to in nature. Such molecules may or may not be present, for example, in a host genome or chromosome.

The present disclosure further provides polynucleotides that are complementary in sequence to the polynucleotides disclosed herein. Polynucleotides and polypeptides of the disclosure can be provided in purified or isolated form.

The subject disclosure also concerns oligonucleotide probes and primers, such as polymerase chain reaction (PCR) primers, that can hybridize to a coding or non-coding sequence of a polynucleotide of the present disclosure. Oligonucleotide probes of the disclosure can be used in methods for detecting and quantitating nucleic acid sequences encoding a mutant UGT polypeptide of the disclosure. Oligonucleotide primers of the disclosure can be used in PCR methods and other methods involving nucleic acid amplification. In a preferred embodiment, a probe or primer of the disclosure can hybridize to a polynucleotide of the disclosure under stringent conditions. Probes and primers of the disclosure can optionally comprise a detectable label or reporter molecule, such as fluorescent molecules, enzymes, radioactive moiety (e.g., $^3$H, $^{35}$S, $^{125}$I, etc.), and the like. Probes and primers of the disclosure can be of any suitable length for the method or assay in which they are being employed. Typically, probes and primers of the disclosure will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the disclosure. Probes and primers of the disclosure can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity allowing the probe or primer to hybridize under stringent conditions to a nucleotide sequence of a polynucleotide of the disclosure. In one embodiment, a probe or primer of the disclosure has 70% or greater, 75% or greater, 80% or greater, 85% or greater, 90% or greater, or 95% to 100% sequence identity with a nucleotide sequence provided herein, including the complement thereof.

Because of the degeneracy of the genetic code, a variety of different polynucleotide sequences can encode polypeptides or mutant polypeptides disclosed herein. All possible triplet codons (and where U also replaces T) and the amino acid encoded by each codon is well-known in the art. In addition, it is well within the capability of one of skill in the art to create alternative polynucleotide sequences encoding the same, or essentially the same, mutant polypeptides of the subject disclosure. These variant or alternative polynucleotide sequences are within the scope of the subject disclosure. As used herein, references to "essentially the same" sequence refers to sequences that encode amino acid substitutions, deletions, additions, or insertions that do not materially alter the functional activity of the polypeptide encoded by the polynucleotides of the present disclosure. Allelic variants of the nucleotide sequences encoding a wild-type or mutant polypeptide of the present disclosure are also encompassed within the scope of the disclosure.

Amino acids can be generally categorized in the following classes: non-polar, uncharged polar, basic, and acidic. Conservative substitutions whereby a mutant UGT polypeptide of the present disclosure and/or a wild-type or mutant UGT polypeptide having an amino acid of one class is replaced with another amino acid of the same class fall within the scope of the subject disclosure so long as the polypeptide having the substitution still retains substantially the same functional activity (e.g., enzymatic and/or increased toxin resistance of the described wild-type or mutant UGT enzyme) as the polypeptide that does not have the substitution. Functional activity may be determined as set forth in the Examples section below. Polynucleotides encoding a mutant UGT polypeptide or a wild-type UGT polypeptide having one or more amino acid substitutions in the sequence are contemplated within the scope of the present disclosure.

Table 1 provides a listing of examples of amino acids belonging to each class.

TABLE 1

Classes of Amino Acids

| | |
|---|---|
| Nonpolar | Ala, Val, Leu, Be, Pro, Met, Phe, Trp, Gly, Cys |
| Uncharged Polar | Gly, Ser, Thr, Cys, Tyr, Asn, Gln |
| Acidic | Asp, Glu |
| Basic | Lys, Arg, His |

Glycine and cysteine are understood in the art to fall in both the nonpolar and uncharged polar classes. Substitution of amino acids other than those specifically exemplified or naturally present in the disclosed wild-type and/or mutant UGT polypeptides are also contemplated within the scope of the present disclosure. For example, non-natural amino acids can be substituted for the amino acids of a mutant UGT polypeptide, so long as the mutant UGT polypeptide having the substituted amino acids retains substantially the same functional activity as the mutant UGT polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, a-amino isobutyric acid, 4-aminobutyric acid, 2-amino butyric acid, γ-amino butyric acid, e-amino hexanoic acid, 6-amino hexanoic acid, 2-amino isobutyric acid, 3-amino propionic acid, norleucine, norvaline, sarcosine, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the disclosed proteins or polypeptides can be of the D (dextrorotary) form or L (levorotary) form. Allelic variants of the disclosed wild-type or mutant UGT polypeptides are also encompassed within the scope of the disclosure.

II. Methods of Modifying Nucleic Acids and Proteins

The subject disclosure also concerns variants of the polynucleotides of the present disclosure that encode functional wild-type or mutant UGT polypeptides of the disclosure. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand), or a linear polypeptide sequence of a reference polypeptide molecule as compared to a test polypeptide molecule, when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). Polynucleotides and polypeptides contemplated within the scope of the subject disclosure can also be defined in terms of identity and/or similarity ranges with those sequences of the disclosure specifically exemplified herein. In certain embodiments, the disclosure provides polypeptide sequences having at least about 70, 75, 80, 85, 90, 95, 99, or 99.5 percent identity to a polypeptide sequence provided herein, including, but not limited to, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32 or SEQ ID NO:34, as well as polypeptide sequences comprising a T291V, T291S, Q202E, F199Q, Q143A, S203L or S203A mutation relative to the wild-type Os79 protein sequence (SEQ ID NO:2). In certain embodiments, the disclosure provides polynucleotide sequences having at least about 70, 75, 80, 85, 90, 95, 99, or 99.5 percent identity to a polynucleotide sequence provided herein, including, but not limited to, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31 or SEQ ID NO:33, as well as polynucleotide sequences encoding a T291V, T291S, Q202E, F199Q, Q143A, S203L or S203A mutation relative to the wild-type Os79 protein sequence (SEQ ID NO:2).

In certain embodiments, structural similarity is used to determine the amino acid residues that "correspond to" the amino acid residues of Os79 (SEQ ID NO:2). It is known in the art that enzymes that belong to the same fold-family as indicated by sequence similarity within a family of proteins and that demonstrate similar enzymatic activity and specificity will exhibit a topologically identical active site. The protein fold is conserved because it maintains a framework on which to carry out the enzymatic activity, even though the sequence identity between evolutionarily distant enzymes might be below 30%. This occurs because catalytic activity requires a finely tuned architecture in the active site of the enzyme where the organization of the side chains are arranged to enhance a chemical reaction. It is the stereochemistry of the catalyzed reaction that dictates the three dimensional arrangement of the active site. An early example of this is seen in the conservation of catalytic residues in esterases and lipases (Cygler, et al., *Protein Sci.* 2:366-382, 1993). Thus, glycosyltransferases that have the same activity are expected to have a closely related active site architecture as defined below. Likewise, changes in the active site architecture to yield a new activity in one enzyme can be expected to can be transferred to a structurally related enzyme with similar effect. This is accepted knowledge in the field of structural enzymology.

Structural models for GT-B fold family members disclosed in the present application can be readily calculated by those familiar with structural biology with publically available software packages including Robetta (Chivian, et al., *Proteins* 61 (Suppl. 7):157-166, 2005) and I-TASSER (Zhang, *BMC Bioinformatics* 9:40, 2008; Roy, et al., *Nature Protocols* 5:725-738, 2010; Yang, et al., *Nature Methods* 12:7-8, 2015). These are proven algorithms for predicting a protein structure that only require the sequence of the enzyme that shows glucosyltransferase activity. These protocols are based on homology modeling, structural fragments, threading, molecular dynamics, and energy minimization, which are needed to yield a high quality molecular model. The resultant models can be superimposed on the structure of Os79 (accession number 5TMB in the protein data bank) and the root mean square difference (rms) for the alpha carbon atoms for the residues that constitute the binding site for trichothecene (Table 2) can be calculated with the program LSQAB in the CCP4 program package (Winn, et al., *Acta Crystallogr. D. Biol. Crystallogr.* 67 (Pt. 4):235-242, 2011), or within the graphic program Pymol for the selected secondary structural elements (DeLano, The PyMOL Molecular Graphics System, 2002). Visual inspection will demonstrate which amino acid residues are structurally equivalent to H122, L123, Q202, and A384 in Os79 in the new structural model and hence can be modified to generate activity towards, for example, T-2 toxin, 4-ANIV, 4,15-diANIV and DAS.

TABLE 2

| Selected Trichothecene Contact residues in Os79 that define the binding site | Secondary Structural Element carrying that residue |
|---|---|
| F21 | V16-F21 (β-strand and loop) |
| H27 | H27-R36 (β-helix) |
| H122, L123 | V116-A133 (β-strand, loop, and α-helix) |
| Q143 | A136-Q143 (β-strand and loop) |
| Q202 | P197-A208 (α-helix) |
| W383, A384 | W383-S395 (Loop and α-helix) |

Figure 1:
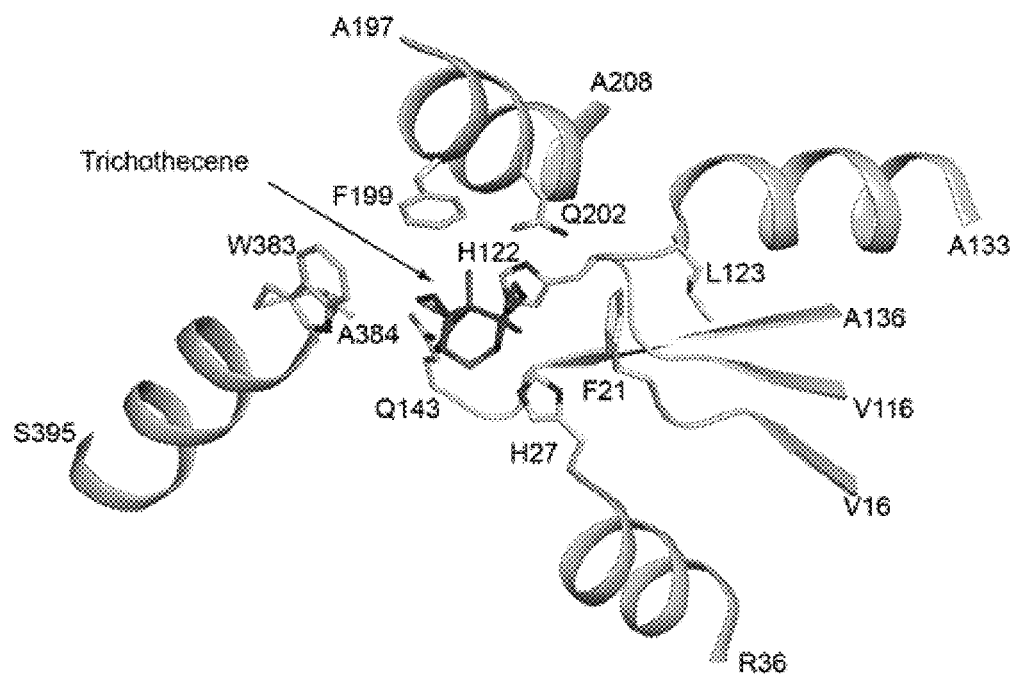

The UDP-glucosyltransferase family of enzymes exhibit a GT-B fold (Lairson, et al., *Annu. Rev. Biochem.* 77:521-555, 2008). This fold consists of two β/α/β Rossmann-like domains that face each other with the active-site lying within the resulting cleft. These domains are associated with the donor (UDP-glucose) and acceptor (DON) substrate-binding sites. The trichothecene binding site (acceptor site) in Os79 is defined by the residues given in Table 1 and their associated secondary structural elements (FIG. 1). The arrangement of ligands provided by the active site are consistent with the chemistry of glucosyl transfer and coordination of the trichothecene substrate. The corresponding structurally equivalent secondary structural elements in the trichothecene binding pocket will lie within an overall root mean square deviation (rms) 2 Å (for the alpha carbon atoms) for sequences that are 20% identical or less and belong to the same fold family (Russell, et al., *J. Mol. Biol.* 269:423-439, 1997). Members of the GT-B glucosyltransferase superfamily that have activity towards DON will have an active site architecture as defined above that exhibits an rms difference of less than 2 Å from that observed in Os79 (5TMB) for the structurally equivalent alpha carbon atoms surrounding the active site. Any GT-B member that falls within these specifications can be modified to yield activity towards T-2 toxin by changing the residues defined in Os79, and thus falls within the scope of the present disclosure.

In certain embodiments, the disclosure provides polynucleotides encoding polypeptides comprising the amino acid sequence provided herein, or a fragment or variant thereof. In certain embodiments, the polynucleotides encode polypeptides comprising a variant or mutant of the amino acid sequence provided herein, wherein the amino acid homologous or corresponding to position 122 ("at position 122") of SEQ ID NO:2 has been mutated, wherein the amino acid at position 123 of SEQ ID NO:2 has been mutated, wherein the amino acid at position 202 of SEQ ID NO:2 has been mutated, wherein the amino acid at position 384 of SEQ ID NO:2 has been mutated, or combinations, fragments, or variants thereof. As used herein, an amino acid homologous or corresponding to position 122, 123, 202 or 384 is an amino acid that is aligned with positions 122, 123, 202 or 384 of SEQ ID NO:2 when using the active site architecture methods to align polypeptides that are described herein. Thus, amino acids "corresponding to" amino acid positions 122, 123, 303 and/or 384 of SEQ ID NO:2 are those that lie within an overall root mean square deviation (rms) of 2 Å (for the alpha carbon atoms). In certain embodiments, the polynucleotides introduced into a plant encode one or more polypeptides comprising a variant wherein the amino acids corresponding to positions 122, 123, 202 and/or 384 of SEQ ID NO:2 have been mutated, or fragments or variants thereof. The disclosure further provides polynucleotides encoding polypeptides comprising a variant of the amino acid sequences provided herein wherein the amino acid corresponding to position 122 has been mutated to be an alanine (A) or other small to medium nonpolar amino acidresidue, wherein the amino acid at position 123 has been mutated to be an A, glycine (G) or other small to medium nonpolar amino acid residue, wherein the amino acid at position 202 has been mutated to be an A, leucine (L), valine (V) or other small to medium nonpolar amino acid residue, and/or wherein the amino acid at position 384 has been mutated to be a serine (S), or combinations thereof.

Fragments and variants of a mutant polypeptide of the present disclosure can be generated as described herein and tested for the presence of enzymatic activity as described herein, or using other standard techniques known in the art. Thus, an ordinarily skilled artisan can readily prepare and test fragments and variants of a mutant polypeptide of the disclosure and determine whether the fragment or variant retains functional activity relative to full-length or a non-variant mutant polypeptide. Fragments and variants of mutant polypeptides can be tested for UGT activity, for example using methods disclosed herein or by other methods well-known in the art.

The subject disclosure also concerns isolated mutant UGT polypeptides. In one embodiment, the mutant UGT polypeptide is an UGT polypeptide of *Oryza sativa*. In a specific embodiment, an UGT polypeptide of the disclosure has an amino acid sequence as shown in the sequence listing, or a functional fragment or variant thereof. An UGT polypeptide or enzyme of the disclosure can be purified using standard techniques known in the art. In one embodiment, a polynucleotide of the disclosure encoding an UGT polypeptide is incorporated into a microorganism, such as *E. coli*, and the UGT polypeptide is expressed in the microorganism and then isolated therefrom.

In certain embodiments, polypeptides of the disclosure, and functional peptide fragments thereof, can be used to generate antibodies that bind specifically to a polypeptide of the disclosure, and such antibodies are contemplated within the scope of the disclosure. The antibodies of the disclosure can be polyclonal or monoclonal and can be produced and isolated using standard methods known in the art.

Polypeptide fragments according to the disclosure typically comprise a contiguous span of at least about 25 and about 463 amino acids of a sequence disclosed herein, including, but not limited to, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32 or SEQ ID NO:34, as well as polypeptide sequences comprising a T291V, T291S, Q202E, F199Q, Q143A, S203L or S203A mutation relative to the wild-type Os79 protein sequence (SEQ ID NO:2). In certain embodiments, polypeptide fragments comprise about 50, about 100, about 150, about 200, about 250, about 300, about 350, about 400 or about 450 amino acids of a sequence provided herein.

Fragments of a mutant UGT polypeptide of the disclosure can be obtained by cleaving the polypeptides of the disclosure with a proteolytic enzyme (such as trypsin, chymotrypsin, or collagenase) or with a chemical reagent, such as cyanogen bromide (CNBr). Alternatively, peptide or polypeptide fragments can be generated in a highly acidic environment, for example at pH 2.5. Peptide or polypeptide fragments can also be prepared by chemical synthesis or using host cells transformed with an expression vector comprising a polynucleotide encoding a fragment of an UGT polypeptide of the disclosure, for example, a mutant polypeptide that is a fragment of an amino acid sequence provided herein.

III. Expression Constructs

Polynucleotides useful in the present disclosure can be provided in an expression construct. Expression constructs of the disclosure generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to one or a combination of nucleic acid sequences that provides for transcription of an operably linked nucleic acid sequence. As used herein, "operably linked" means two DNA molecules linked in manner so that one may affect the function of the other. Operably-linked DNA molecules may be part of a single contiguous molecule and may or may not be adjacent. For example, a promoter is operably linked with a polypeptide-encoding DNA molecule in a DNA construct where the two DNA molecules are so arranged that the promoter may affect the expression of the DNA molecule.

As used herein, the term "heterologous" refers to the relationship between two or more items derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell, seed, or organism into which it is inserted when it would not naturally occur in that particular cell, seed, or organism.

An expression construct of the disclosure can comprise a promoter sequence operably linked to a polynucleotide sequence encoding a modified polypeptide of the disclosure. Promoters can be incorporated into a polynucleotide using standard techniques known in the art. Multiple copies of promoters or multiple promoters can be used in an expression construct of the disclosure. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

Embodiments of the disclosure further provide a recombinant DNA molecule encoding a modified UGT polypeptide, wherein the modified UGT polypeptide comprises the amino acid sequence of SEQ ID NO:4, wherein the recombinant DNA molecule is further defined as operably linked to a heterologous regulatory element. In specific embodiments, the heterologous regulatory element is a promoter functional in a plant cell. In further embodiments, the promoter is an inducible promoter.

If the expression construct is to be provided in or introduced into a plant cell, then plant viral promoters, such as, for example, a cauliflower mosaic virus (CaMV) 35S (including the enhanced CaMV 35S promoter (see, e.g., U.S. Pat. No. 5,106,739)), a CaMV 19S promoter or a cassava vein mosaic virus promoter can be used. Other promoters that can be used for expression constructs in plants include, but are not limited to, zein promoters including maize zein promoters, prolifera promoter, Ap3 promoter, heat shock promoters, T-DNA 1'- or 2'-promoter of *A. tumefaciens*, polygalacturonase promoter, chalcone synthase A (CHS-A) promoter from *petunia*, tobacco PR-1a promoter, ubiquitin promoter, actin promoter, alcA gene promoter, pin2 promoter (Xu, et al., *Plant Mol. Biol.* 22:573-588, 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the disclosure.

Expression constructs of the disclosure may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the disclosure. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements should be present within the transcribed region and are orientation dependent. Examples include the maize shrunken-1 enhancer element (Clancy and Hannah, *Plant Physiol.* 130:918-929, 2002).

IV. Transformation Methods

One aspect of the disclosure includes plant cells, plant tissues, plants, and seeds that comprise the recombinant DNA provided by the disclosure. These cells, tissues, plants, and seeds comprising the recombinant DNA molecules exhibit resistance to diseases caused by *Fusarium*. Suitable methods for transformation of host plant cells for use with the current disclosure include virtually any method by which DNA can be introduced into a cell (for example, where a recombinant DNA construct is stably integrated into a plant chromosome) and are well-known in the art. Two effective methods for cell transformation are *Agrobacterium*-mediated transformation and microprojectile bombardment-mediated transformation. Microprojectile bombardment methods are illustrated, for example, in U.S. Pat. Nos. 5,550,318, 5,538,880, 6,160,208, and 6,399,861. *Agrobacterium*-mediated transformation methods are described, for example in U.S. Pat. No. 5,591,616. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores and pollen. Callus can be initiated from tissue sources including, but not limited to, immature or mature embryos, hypocotyls, seedling apical meristems, microspores and the like. Cells containing a transgenic nucleus are grown into transgenic plants.

In transformation, DNA is typically introduced into only a small percentage of target plant cells in any one transformation experiment. Marker genes are typically used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glypho sate (aroA or EPSPS). Examples of such selectable markers are illustrated in U.S. Pat. Nos. 5,550,318, 5,633,435, 5,780,708 and 6,118,047. Markers that provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

The present disclosure provides methods and constructs for regenerating a plant from a cell with modified genomic DNA resulting from genome editing. The regenerated plant can then be used to propagate additional plants.

V. Genome Editing

Targeted modification of plant genomes through the use of genome editing methods can be used to create improved mutant or transgenic plant lines through modification or insertion of plant genomic DNA. In addition, genome editing methods can enable targeted insertion of multiple nucleic acids of interest (a trait stack) into a plant genome. Exemplary methods for introducing recombinant DNA constructs into a plant or modifying genomic DNA of a plant include the use of zinc-finger nucleases, engineered or native meganucleases, TALE-endonucleases, or an RNA-guided endonuclease (for example a Clustered Regularly Interspersed Short Palindromic Repeat (CRISPR)/Cas9 system). Methods of genome editing to modify, delete, or insert genomic DNA are known in the art.

In exemplary methods provided by the disclosure, a CRISPR/Cas9 system is used to modify or replace an existing coding sequence within a plant genome, such as a sequence encoding an UGT polypeptide. In further embodiments, transcription activator-like effectors (TALEs) are used for modification or replacement of an existing coding sequence within a plant genome, such as a sequence encoding an UGT polypeptide. Modification or replacement of an endogenous UGT-encoding sequence according to the methods provided herein results in a polypeptide comprising a modified UGT enzyme, for example wherein the amino acid corresponding to position 122 of SEQ ID NO:2 has been mutated to A, wherein the amino acid at position 123 of SEQ ID NO:2 has been mutated to A or G, wherein the amino acid at position 202 of SEQ ID NO:2 has been mutated to A, L or V, and/or wherein the amino acid at position 384 of SEQ ID NO:2 has been mutated to S, or combinations thereof. The disclosure therefore provides DNA constructs capable of recognizing a specific nucleotide sequence of interest, such as an UGT sequence, within a genome of a plant to allow for mutation or integration at that site.

In certain embodiments, genome editing methods provided by the disclosure may introduce single nucleotide mutations, or alterations to a number of nucleotides within a target sequence, such as an UGT-encoding sequence. Modifications to an UGT-encoding sequence, for example a sequence provided herein as SEQ ID NO:2, may result in a sequence encoding an UGT polypeptide, for example wherein the amino acid corresponding to position 122 of SEQ ID NO:2 has been mutated to A, wherein the amino acid at position 123 of SEQ ID NO:2 has been mutated to A or G, wherein the amino acid at position 202 of SEQ ID NO:2 has been mutated to A, L or V, and/or wherein the amino acid at position 384 of SEQ ID NO:2 has been mutated to S, or combinations thereof as described herein, capable of conferring to a plant improved resistance to toxins produced by various species of *Fusarium*, which confers resistance to diseases caused by *Fusarium* species.

In further embodiments, a DNA sequence, such as a transgene or expression cassette, may be inserted or integrated into a specific site or locus within the genome of a plant or plant cell via site-directed integration. Recombinant DNA constructs and recombinant DNA molecules provided herein may thus include a donor template sequence comprising at least one transgene, expression cassette, or other DNA sequence for insertion into the genome of the plant or plant cell. In certain embodiments of the disclosure, a donor template sequence comprises a nucleotide sequence encoding a polypeptide wherein of SEQ ID NO:2 has been altered to have improved resistance to toxins produced by various species of *Fusarium*, for example the polypeptide of SEQ ID NO:4, SEQ ID NO:6, SEQ ID NO:8, SEQ ID NO:10, SEQ ID NO:12, SEQ ID NO:14, SEQ ID NO:16 or SEQ ID NO:18, or a sequence encoding a fragment of such a polypeptide, or a nucleotide sequence encoding a polypeptide wherein of SEQ ID NO:20 has been altered to have improved resistance to toxins produced by various species of *Fusarium*, for example the polypeptide of SEQ ID NO:22. A donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. As understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

The disclosure further provides plants produced by the methods disclosed herein. Plants of the present disclosure may be monocots or dicots, and may include, for example, rice, wheat, barley, oats, rye, sorghum, maize, soybean, alfalfa, sunflower, cotton, canola, sugar beet, sweet potato, tomato, tobacco, banana, curcubits and pepper plants.

VI. Toxins Produced by *Fusarium*

One aspect of the disclosure includes plant cells, plant tissues, plants, and seeds that comprise the recombinant DNA provided by the disclosure. These cells, tissues, plants, and seeds comprising the recombinant DNA molecules exhibit resistance to one or more of the toxins produced by various species of *Fusarium*. Non-limiting examples include: DAS, which is produced by *Fusarium acuminatum, Fusarium equiseti, Fusarium langsethiae, Fusarium poae, Fusarium sambucinum, Fusarium semitectum, Fusarium sporotrichioides, Fusarium venenatum*; T-2 toxin, which is produced by *Fusarium acuminatum, Fusarium armeniacum, Fusarium equiseti, Fusarium kyushuense, Fusarium langsethiae, Fusarium oxysporum, Fusarium sambucinum, Fusarium sporotrichioides*; DON, which is produced by *Fusarium asiaticum, Fusarium austroamericanum, Fusarium boothii, Fusarium culmorum, Fusarium graminearum, Fusarium mesoamericanum, Fusarium* pseudograminearum; HT-2, which is produced by *Fusarium acuminatum, Fusarium armeniacum, Fusarium langsethiae, Fusarium oxysporum, Fusarium sambucinum, Fusarium sporotrichioides*; and NIV, which is produced by *Fusarium asiaticum, Fusarium austroamericanum, Fusarium cortaderiae, Fusarium crookwellense, Fusarium culmorum, Fusarium equiseti, Fusarium graminearum, Fusarium kyushuense, Fusarium meridionale, Fusarium mesoamericanum, Fusarium pseudograminearum*. Examples of these and other toxins produced by these species and other *Fusarium* species are well-known to those of skill in the art.

As used herein, "resistance" or "*Fusarium* resistance" means a plant, seed, or cell's ability to resist the toxic effects of one or more toxin when infected or contacted with *Fusarium. The resistance of a plant, seed, plant tissue, plant part, or cell may be measured by comparing the plant, seed, plant tissue, plant part, or cell to a suitable control. For example, the resistance may be measured or assessed by applying Fusarium* to a plant comprising a recombinant DNA molecule encoding a modified polypeptide capable of conferring resistance to *Fusarium* (the test plant) and a plant not comprising the recombinant DNA molecule encoding the modified polypeptide capable of conferring resistance to *Fusarium* (the control plant) and then comparing the plant injury or toxin levels of the two plants (or parts thereof), where resistance of the test plant is indicated by a decreased injury rate or toxin level as compared to the injury rate or toxin level of the control plant. A *Fusarium* resistant plant, seed, plant tissue, plant part, or cells exhibits a decreased response to the toxic effects of *Fusarium* infection, or decreased levels of one or more *Fusarium* toxin, when compared to a control plant, seed, plant tissue, plant part, or cell. As used herein, a "*Fusarium* resistance trait" is a transgenic trait imparting improved resistance to a plant as compared to the wild-type plant.

EXAMPLES

Example 1

Cloning and Expression of Os79

The gene for Os79 was amplified by polymerase chain reaction (PCR) using the forward primer 5'-ATGGGCTCTATGTCCACTCCTGC-3' (SEQ ID NO:35) and the reverse primer 5'-ATTGGAATACTTTGCTGCAAACTC-3' (SEQ ID NO:36) from plasmid pWS57 that contained a codon optimized sequence for yeast (Michlmayr, et al., *Toxins* 7:2685-2700, 2015). The resulting product was introduced into plasmid pKLD116, a pET31b derivative containing His6-tagged maltose-binding protein (MBP) followed by a TEV protease cleavage site (Rocco, et al., *Plasmid* 59:231-237, 2008), using an enzyme-free "Quikchange" method (Chen, et al., *BioTechniques* 28:504-495, 2000; van den Ent and Lowe, *J. Biochem. Biophys. Methods* 67:67-74, 2006). Os79 was overexpressed in *E. coli* strain BL21 Codon Plus (DE3). Cultures from a single colony were used to inoculate 6 L of lysogeny broth (LB) supplemented with 100 μg/mL ampicillin and 30 μg/mL chloramphenicol. Expression of Os79 was induced with 1 mM isopropyl β-D-thiogalactopyranoside when cultures reached an OD600 of ~1.0. Induction was conducted at 16° C. for 20 hours. Cells were harvested by centrifugation at 2500 g, washed with buffer containing 10 mM 4-(2-hydroxyethyl)-1-piperazineethanesulfonic acid (HEPES) (pH 7.6), and 100 mM NaCl, and flash-frozen in liquid nitrogen. Cells were stored at −80° C. until they were used.

Example 2

Site-Directed Mutagenesis of Os79

Mutants of Os79 were generated using a single primer, PCR based method based on "Quikchange" mutagenesis (Chen, et al., *BioTechniques* 28:504-495, 2000; van den Ent and Lowe, *J. Biochem. Biophys. Methods* 67:67-74, 2006). The following mutagenesis primers were used for Os79: Q202A: 5'-TCCTGCCTTCTGTGAGGCGTCTATCGAGCAGTTTGCT-3' (SEQ ID NO:37); Q202L: 5'-TCCTGCCTTCTGTGAGCTGTCTATCGAGCAGTTTGCT-3' (SEQ ID NO:38); Q202V: 5'-TCCTGCCTTCTGTGAGGTGTCTATCGAGCAGTTTGCT-3' (SEQ ID NO:39); A384S: 5'-GCTATGCCTCACTGGTCTGATCAACCTACTATTAGCAAGTATG-3' (SEQ ID NO:40); H122A/L123A: 5'-AGAGTTTTAGTCTACGATCCAGCGGCGCCATGGGCTAGAAGAGT-3' (SEQ ID NO:41); H122A/L123G: 5'-AGAGTTTTAGTCT ACGATCCAGCGGGCCCATGGGCTAGAAGAGT-3 (SEQ ID NO:42); T291V: 5'-GGTTTT GGTGTCATACGGAGTGGTTTCTACTTTTGATGTTGCTAAAC-3' (SEQ ID NO:47); T291S: 5'-GGTTTTGGTGTCATACGGAAGCGTTTCTACTTTT- GATGTTGCTAAAC-3' (SEQ ID NO:48); Q202E: 5'-TCCTGCCTTCTGTGAGGAATCTATCGAGCAGTTTGCT-3' (SEQ ID NO:49); F199Q: 5'-CCTGAATTAACTCCTGCCCAATGTGAGCAATC-TATC GAGC-3' (SEQ ID NO:50); Q143A: 5'-CAGCCG-CATTTCTAAGTGCGCCATGTGCTG TGGAC-3' (SEQ ID NO:51); S203L: 5'-GCCTTCTGTGAGCAATTGATC-GAGCAGTTT GCTG (SEQ ID NO:52); and S203A: 5'-GCCTTCTGTGAGCAAGCTATCGAGCAGTTT GCTG (SEQ ID NO:53). The following mutagenesis primer was used for HvUGT13248: H132A/L133A: 5'-CCCGT-GCGCGTGCTGGTGTACGACGCTGCGGCG-GCGTGGGCAC GGCGGGTGGCACA-3' (SEQ ID NO:43). All mutations were verified by DNA sequencing using BigDye® protocols (ABI PRISM). Multiple mutations were introduced by adding all relevant primers to the Quikchange reaction mixture. For example, the H122A/L123A/Q202L mutant was generated adding both the H122A/L123A and Q202L primers.

Example 3

Expression and Purification of Os79 Mutants

Os79 mutants were overexpressed in *E. coli* strain BL21 Codon Plus (DE3). Cultures from a single colony were used to inoculate 6 L Lysogeny broth (LB) supplemented with 100 μg/mL ampicillin and 30 μg/mL chloramphenicol. Expression of Os79 was induced with 1 mM isopropyl-β-D-thiogalactopyranoside when cultures reached $OD_{600}$ ~0.8. Induction was carried out at 16° C. for 20 hours. Cells were harvested by centrifugation at 3,000×g, washed with buffer containing 10 mM HEPES pH 7.6 and 100 mM NaCl, and flash-frozen in liquid nitrogen. Cells were stored at −80° C. until use.

All Os79 mutants were purified in a similar manner. All purification steps were carried out on ice or at 4° C. Around twenty grams of *E. coli* cells expressing $His_6$-MBP-Os79 were resuspended in 100 mL buffer containing 20 mM HEPES pH 7.6, 50 mM NaCl, 0.2 mM tris(2-carboxyethyl) phosphine (TCEP), 1 mM PMSF, 50 nM leupeptin (Peptide International), 70 nM E-65 (Peptide International), 2 nM aprotinin (ProSpec), 2 mM AEBSF (Gold BioTechnology) and 50 mg lysozyme. Cells were lysed with 5 pulses (45 s) using a Qsonica Q700 sonicator, and the lysate was clarified by centrifugation at 40,000 rpm in a Ti 45 rotor (Beckman-Coulter) for 30 min. The concentration of NaCl and imidazole were raised to 300 mM and 20 mM, respectively, by the addition of 4 M stock solutions and loaded onto an 5 mL nickel-nitrilotriacetic acid (NiNTA; Qiagen) column equilibrated with NTA buffer: 50 mM HEPES, pH 7.6, 300 mM NaCl, 20 mM imidazole, and 0.2 mM TCEP. After loading, the column was washed with 120 mL of NTA buffer. Os79 was eluted with 40 mL NTA buffer containing 300 mM imidazole. $His_6$-tagged Tobacco etch virus (TEV) protease was added at 1:40 molar ratio to cleave the $His_6$-MBP from Os79. The mixture was dialyzed overnight in a buffer containing 10 mM HEPES pH 7.6, 50 mM NaCl, 0.5 mM EDTA, 0.2 mM TCEP. The NaCl and imidazole concentrations were brought up to 300 mM and 20 mM, respectively, and the solution was passed over a 5 mL NiNTA column equilibrated with NTA buffer. The flow-though contained Os79, while the column retained TEV protease, $His_6$-MBP, and undigested $His_6$-MBP Os79. Purified Os79 was concentrated using a centrifugal filter (Amicon) with a 30,000 nominal molecular weight limit to a final concentration of 10-20 mg/mL, estimated using calculated molar extinction coefficient of 57870 $M^{-1} \cdot cm^{-1}$ at 280 nm. Proteins were dialyzed against a storage buffer containing 10 mM HEPES pH 7.6, 0.2 mM TCEP, drop frozen in 30 μL aliquots in liquid nitrogen, and stored at −80° C.

Example 4

Crystallization

Crystallization of Os79.deoxynivalenol-3-O-glucoside (D3G).UDP. Os79 was screened for initial crystallization conditions with a 144-condition sparse-matrix screen developed by the inventors. Single, diffraction quality crystals were grown at 4° C. by hanging drop vapor diffusion by mixing 2 μL of Os79 at 12 mg/mL in 10 mM HEPES pH 7.6, 50 mM NaCl, 30 mM D3G, 5 mM UDP with 2 μL well solution containing 100 mM sodium acetate pH 5.0, 40% pentaerythritol propoxylate 426, 320 mM NaCl (Gulick, et al., *Acta Crystallogr. D Biol. Crystallogr.* 58:306-309, 2002). Hanging droplets were nucleated after 24 h from an earlier spontaneous crystallization event using a cat's whisker. Crystals grew to approximate dimensions of 100×100×300 μm within 15 days. The crystals were transferred to a cryoprotecting solution that contained 100 mM sodium acetate pH 5.0, 40% pentaerythritol propoxylate 426, 320 mM NaCl, 30 mM D3G, 5 mM UDP and vitrified by rapid-plunging into liquid nitrogen. Os79 crystallized in the space group $P3_221$ with unit cell dimensions of a=104.5 Å, b=104.5 Å, c=98.3 Å and one chain in the asymmetric unit.

Crystallization of Os79 Q202A.UDP. Os79 Q202A was screened for initial crystallization conditions as described above. Single, diffraction quality crystals were grown at 4° C. by hanging drop vapor diffusion by mixing 2 μL of 11 mg/mL Os79 Q202A in 10 mM HEPES pH 7.6, 5 mM UDP-glucose with 2 μL well solution containing 100 mM 3-(N-Morpholino)propanesulfonic acid pH 7.5, 15% methyl ether polyethylene glycol 5000 (MEPEG 5K), 160 mM potassium glutamate. Hanging droplets were nucleated after 24 h from an earlier spontaneous crystallization event using a cat's whisker. Crystals grew to approximate dimensions of 100×100×300 μm within 8 days. The crystals were transferred stepwise to a cryoprotecting solution that contained 100 mM 3-(N-Morpholino)propanesulfonic acid pH 7.5, 15% MEPEG 5K, 15% glycerol, 5 mM UDP-glucose and vitrified by rapid plunging into liquid nitrogen. Os79 Q202A crystallized in the space group $P2_12_12_1$ with unit cell dimensions of a=59.4 A, b=83.2 A, c=99.1 A and one chain in the asymmetric unit.

Crystallization of Os79 T291V.UDP. The Os79 protein complex T291V.UDP was screened for initial crystallization conditions as described above. Single, diffraction quality crystals were grown at 23° C. by hanging drop vapor diffusion by mixing 2 μL of 10 mg/mL T291V Os79 in 10 mM HEPES pH 7.6, 50 mM NaCl, 5 mM UDP-glucose with 2 μL well solution containing 50 mM HEPES pH 7.5, 32% MEPEG 5K. Hanging droplets were nucleated after 24 h from an earlier spontaneous crystallization event using a cat's whisker. Crystals grew to approximate dimensions of 75×75×300 μm within 11 days. The crystals were transferred to a cryoprotecting solution that contained 50 mM HEPES 7.5, 32% MEPEG 5K, 5 mM UDP-glucose and vitrified by rapid plunging into liquid nitrogen. Os79 crystallized in the space group $P2_12_12_1$ with unit cell dimensions of a=59.4 Å, b=83.2 Å, c=98.7 Å and one chain in the asymmetric unit.

Crystallization of Os79 H122A/L123A.UDP. Os79 was screened for initial crystallization conditions as described above. Single, diffraction quality crystals were grown at 23° C. by hanging drop vapor diffusion by mixing 2 μL of 11 mg/mL Os79 in 10 mM HEPES pH 7.6, 50 mM NaCl, 5 mM UDP with 2 μL well solution containing 50 mM HEPES pH 7.0, 18% methyl ether polyethylene glycol 2000. Hanging droplets were nucleated after 24 h from an earlier spontaneous crystallization event using a cat's whisker. Crystals grew to approximate dimensions of 75×75×300 μm within 4 days. The crystals were transferred stepwise to a cryoprotecting solution that contained 50 mM HEPES 7.0, 20% methyl ether polyethylene glycol 2000, 15% glycerol, and 5 mM UDP and vitrified by rapid plunging into liquid nitrogen. Os79 crystallized in the space group $P2_12_12_1$ with unit cell dimensions of a=59.3 Å, b=82.9 Å, c=99.0 Å and one chain in the asymmetric unit.

Data collection and Refinement. X-ray data for the Os79 structures were collected at 100 K. Diffraction data were integrated and scaled with HKL3000 (Minor, et al., *Acta Crystallogr. D Biol. Crystallogr.* 62:859-866, 2006). Data collection and refinement statistics are given in Table 3. The structures were determined by molecular replacement using coordinates from the RCSB (accession number 5TME) as the molecular replacement search model in the program Phaser (Wetterhorn, et al., *Biochemistry-Us* 55:6175-6186, 2016; McCoy, et al., *J. Appl. Crystallogr.* 40:658-674, 2007). Final models were generated by alternating cycles of manual building and least-squares refinement using Coot, Phenix and Refmac (Murshudov, et al., *Acta Crystallogr. D Biol. Crystallogr.* 53:240-255, 1997; Emsley amd Cowtan, *Acta Crystallogr. D Biol. Crystallogr.* 60:2126-2132, 2004; Adams, et al., *Acta Crystallogr. D Biol. Crystallogr.* 66:213-221, 2010).

Example 5

Glucosyltransferase Enzyme Assays

Steady-state kinetic analyses of wild-type Os79 (SEQ ID NO:2) and mutant Os79 (SEQ ID NO:4) with trichothecene substrates were performed in a coupled—continuous enzymatic assay at 23° C. in a 1 cm path length cuvette. Reactions were initiated by the addition of varying volumes of trichothecenes to a master mix containing Os79 (58 nM final concentration), 3 units rabbit muscle lactic dehydrogenase and 2 units rabbit muscle pyruvate kinase (Sigma-Aldrich, buffered aqueous glycerol solution), 1.5 mM phosphoenolpyruvate, 100 μM β-NADH, 50 mM KCl, 10 mM $MnCl_2$, and 100 mM glycylglycine pH 8.0 to yield a final volume of 100 μL. Lactic dehydrogenase, pyruvate kinase, phosphoenolpyruvate, β-NADH, Os79, and UDP-glucose were added to a master-mix containing the remaining reaction components prior to the initiation of each reaction. Reaction progress was followed by monitoring the decrease in $A_{340}$ caused by the oxidation of β-NADH. The rates of reaction were determined at various trichothecene concentrations and fit by non-linear regression to the Michaelis-Menten equation using GraphPad Prism software. The final mutant enzyme concentrations were 58 nM except for H122A/L123G which was 588 nM.

Os79 glycosylates DON ($k_{cat}$=0.57 $s^{-1}$, $K_m$=0.23 mM; Michlmayr, et al., 2015, supra), while the results of the assay shows that Os79 H122A/L123A/Q202L glycosylates DON ($k_{cat}$=0.85 $s^{-1}$, $K_M$=261 μM), T-2 toxin ($k_{cat}$=0.9 $s^{-1}$, $K_M$=118 μM) and 4-ANIV ($k_{cat}$=0.96 $s^{-1}$, $K_M$=88 μM). Os79 H122A/L123A/Q202A glycosylates DON ($k_{cat}$=0.9 $s^{-1}$, $K_M$=1.2 mM), T-2 toxin ($k_{cat}$=2.5 $s^{-1}$, $K_M$=89 μM), DAS ($k_{cat}$=1.8 $s^{-1}$, $K_M$=49 μM), and 4-ANIV ($k_{cat}$=1.1 $s^{-1}$, $K_M$=501 μM). Os79 H122A/L123A glycosylates T-2 toxin

TABLE 3

| Protein | Os79 Q202A · UDP | Os79 H122A/L123A · UDP | Os79 T291V · UDP | Os79 · D3G · UDP |
|---|---|---|---|---|
| PDB ID | 6BK0 | 6BK2 | 6BK1 | 6BK3 |
| space group | $P2_12_12_1$ | $P2_12_12_1$ | $P2_12_12_1$ | $P3_221$ |
| Unit cell dimensions, Å | a = 59.4, b = 83.2, c = 99.1 | a = 59.3, b = 82.9, c = 99.0 | a = 59.4, b = 83.2, c = 98.7 | a = 104.5, b = 104.5, c = 98.3 |
| Wavelength (Å) | 0.979 | 0.979 | 0.979 | 0.979 |
| resolution range (Å) | 50-1.47 (1.5-1.47)[a] | 50-1.29 (1.31-1.29)[a] | 50-1.58 (1.61-1.58)[a] | 50-2.17 (2.21-2.17)[a] |
| reflections: | 1095493 | 1504096 | 568452 | 382690 |
| reflections: unique | 79234 | 115974 | 63979 | 33082 |
| redundancy | 13.1 (12.6) | 12.3 (8.5) | 8.4 (6.2) | 11.6 (8.6) |
| completeness (%) | 99.2 (84.1) | 99.2 (96.9) | 99.8 (95.2) | 100 (100) |
| average I/σ | 41.3 (9.2) | 34.9 (4.0) | 83.6 (11) | 29.1 (4.4) |
| $R_{merge}$ (%)[b] | 5.1 (23.1) | 10.2 (0) | 5.2 (18.0) | 8.6 (55.5) |
| $R_{work}$ | 15.1 | 16.0 | 16.0 | 19.6 |
| $R_{free}$ | 17.9 | 18.0 | 19.2 | 21.0 |
| protein atoms | 3499 | 3464 | 3407 | 3353 |
| ligand atoms | 36 | 36 | 36 | 56 |
| water molecules | 608 | 398 | 557 | 197 |
| average B factors | 19.3 | 17.9 | 27.3 | 35.1 |
| Ramachandran | — | — | — | — |
| most favored | 96.8 | 97.2 | 97.5 | 96.0 |
| allowed | 2.98 | 2.8 | 2.5 | 4.0 |
| disallowed | 0.23 | 0 | 0.0 | 0.0 |
| rms deviations | — | — | — | — |
| bond lengths (Å) | 0.022 | 0.021 | 0.013 | 0.023 |
| bond angles (deg) | 1.889 | 1.755 | 1.573 | 2.234 |

[a] Values in parenthesis are for highest resolution shell.

[b] $R_{merge} = \Sigma |I_{(hkl)} - I| \times 100/\Sigma |I_{(hkl)}|$, where the average intensity I is taken over all symmetry equivalent measurements and $I_{(hkl)}$ is the measured intensity for a given observation.

($k_{cat}$=1.6 s$^{-1}$, $K_M$=926 µM). Os79 H122A/L123G glycosylates T-2 toxin ($k_{cat}$=0.26 s$^{-1}$, $K_M$=512 µM), and DON ($k_{cat}$=0.5 s$^{-1}$, $K_M$=2.5 mM). Any mutants or substrates for which kinetic parameters were not included were found to glycosylate/be glycosylated by the observation of activity at a single high substrate concentration and thus $k_{cat}$ and $K_M$ were not determined in these cases.

Example 6

Role of the Conserved Thr 291 in Os79

To address the structural role of Thr 291, the structure of Os79 T291V in complex with UDP was determined to 1.61 Å resolution (PDB: 6BK1) (Table 3). When the hydroxyl of Thr 291 is replaced with a methyl group in Os79 T291V the phosphate of UDP adopts a substantially different position in the active site compared to that seen in WT Os79. In the WT Os79 structure there is a hydrogen bond between the threonine hydroxyl and a phosphate oxygen atom of length about 2.5 Å. This is clearly lost when threonine is replaced by a valine. The change in the position of UDP is likely a direct result of the substitution since crystals of Os79 T291V and WT protein structures were grown at the same pH and under very similar crystallization conditions.

The importance of this interaction is confirmed as this interaction is present in all plant GT-1 glycosyltransferases. Comparison of the structures of six plant UGT structures that have been determined with UDP bound in their active sites reveals that the presence of a hydroxyl moiety within hydrogen bonding distance of a β-phosphate oxygen is a conserved characteristic in all of these enzymes. The proteins were aligned by superimposing an α-helix and two beta strands that surround the UDP binding site, because the overall architecture of these proteins varies substantially at the periphery of the protein, away from the UDP binding site. These three secondary structural elements that underlie the framework for the UDP binding site are very similar across the six proteins and align with an average rmsd (root mean square deviation) of 0.30 Å for the alpha carbon atoms. In every case, there is a threonine or serine hydroxyl positioned within 3.0 Å of the phosphate oxygen. In every structure the phosphate adopts almost exactly the same orientation. This provides further evidence that the change in the orientation of the phosphate of UDP in the T291V structure is caused by the lack of a hydroxyl group and the inability to form a hydrogen bond. This serine or threonine residue has not been previously identified as a catalytically extremely important residue. The present disclosure demonstrates that it is extremely important for orienting the phosphate in the active site. While this does not preclude it from participating as a catalytic acid, it does confirm a structural role for this side chain. This likely applies to many, if not all, plant UGTs.

Example 7

Steady-State Kinetic Parameters for WT Os79

Many plant UGTs demonstrate broad substrate specificity, a useful characteristic when considering enzymes that glycosylate xenobiotics. Os79 exhibits broad specificity and can glycosylate DON, HT-2, IsoT, and NIV but not T-2, 4-ANIV, 4,15-di-ANIV or DAS. T-2 is commonly produced by *Fusarium* species in Europe, Asia, Africa, and Australia. Given the importance of detoxifying T-2, expanding the specificity of Os79 to include this trichothecene and others would be of great benefit. Given that the only difference between T-2 and HT-2 toxin is the C4 acetyl group that is present on T-2 in place of the hydroxyl on HT-2 the inventors reasoned that this acetyl group prevented T-2 from binding in the active site of Os79. By this reasoning, 4-acetyl nivalenol (4-ANIV), commonly known as FUS-X, will not be a substrate for Os79. 4-ANIV is acetylated at the C4 position but lacks the C15 acetyl and C8 isovaleryl groups of T-2. Indeed, glycosylation could not be detected with the coupled assay with 4-ANIV, 4,15-diANIV or DAS. This confirms that the 4-acetyl group is responsible for precluding T-2, 4-ANIV, 4,15-diANIV and DAS from the acceptor binding pocket. To further examine the structural aspects of the acceptor binding pocket that contribute to its inability to accommodate an acetyl group on the C4 position, the structure of Os79 with the glycosylated trichothecene product D3G in the active site was determined.

Example 8

Structure of Os79 in Complex with UDP and D3G

Os79 was crystallized in the presence of the product D3G to further examine the structural components responsible for substrate specificity and further understand the nature of trichothecene binding in the acceptor pocket. The structure of Os79 in complex with UDP and D3G was determined to 2.17 Å resolution (PDB: 6BK3) (Table 3). The overall structure is very similar to the previously solved structure of Os79 with trichothecene (TRI) and UDP-2-fluoro-2-deoxy-D-glucose (U2F) bound in the active site with an rmsd of 0.7 Å for structurally equivalent α-carbons. Electron density corresponding to DON and UDP was observed, however there was no clear electron density corresponding to the glucose moiety of D3G and the moiety was not modeled. This appears to be the result of the flexibility of the glucose moiety.

There are two major conformational changes in Os79 with D3G bound compared to the structure with trichothecene bound in the active site. A loop from Ser 288 to Val 297 is shifted 9.5 Å away from the active site and the region that extends from Trp 316 to Lys 336, which is composed of a loop and two short α-helices, is shifted 5.9 Å away from the active site. These conformational changes highlight the flexibility of the acceptor binding region of the protein, and help to show the structural basis for UDP release after the donor sugar has been transferred. Aligning the structures with TRI or D3G bound in the active site reveals that the trichothecene skeleton of DON is rotated about 45 degrees compared to the backbone of TRI. This change is most probably the result of the presence of glucose on C3 and shows that the trichothecene backbone rotates in the acceptor binding pocket after the reaction is completed and before the glycosylated product is released. The orientation of trichothecene is more representative than D3G of the positioning of DON in the active site prior to glycosylation. Using the orientation of trichothecene as a reference, His 122, which is only 4.2 Å away from C4, was identified as a residue that could clash with the C4 acetyl of the substrates that WT Os79 is unable to glycosylate. Based on the presently disclosed structural information, the role of His 122 and other residues identified as potential contributors to the specificity of Os79 were investigated by kinetic analysis.

Example 9

Steady-State Kinetic Assays on Os79 Mutants

The remarkable substrate plasticity of Os79 prompted the inventors to investigate whether there are important residues in the trichothecene binding pocket that facilitate this ability. It also raised in the inventors the possibility of expanding the substrate specificity to accommodate trichothecenes with large substituents such as acetyl groups at the C4 position. Examination of the structures with trichothecene and D3G suggested seven residues that might influence binding. Three of these seven side chains, Phe 199, Gln 202, and Ser 203, are located on an α-helix that forms the back of the acceptor pocket. His 122 and Leu 123 are on a loop located in the binding pocket. Gln 143 and Ala 384 are on two separate loops in the binding pocket. Steady-state kinetic constants were determined for eight mutant proteins where these included single changes and combinations thereof. The effect of each of these mutations is discussed below.

Role of Gln 202. Gln 202 is located on an α-helix in the back of the acceptor binding pocket. In the presently disclosed model of DON binding in the acceptor pocket the carboxamide oxygen of Gln 202 is within hydrogen bonding distance (2.3 Å) of the C7 hydroxyl of DON. To examine the contribution of this residue to specificity it was changed to a glutamate, alanine, and leucine. The $K_M$ value of Os79 Q202E is 17.5-fold higher than the $K_M$ of WT with DON as a substrate where this is accompanied with a small increase in $k_{cat}$. The Q202E substitution maintains a similar residue size at the 202 position but adds a negative charge. The Q202E substitution may contribute a hydrogen bond to the enzyme substrate complex. To test whether there is a hydrogen bond that plays a role in DON binding between this hydroxyl and Gln 202 the kinetic constants for Os79 Q202A were determined. There is no significant difference in the $K_M$ value of Os79 Q202A compared to WT, indicating that either Gln 202 does not play a role in DON binding or that a water molecule can substitute the place of the side chain. Interestingly, the Q202L substitution decreases the $K_M$ for DON by 4.7-fold without a major change in the value of $k_{cat}$, which is in contrast to the increase generated by the Q202E mutation. Together these substitutions emphasize the impact that substitutions at position 202 can have on substrate and product binding. In summary, these mutations suggest that a polar interaction in this position is not important for activity and that an increased charge is detrimental.

Role of Phe 199. Phe 199 is located in the α-helix one helical turn away from Gln 202 and lies at the top of the active site and makes a substantial contribution to the primarily hydrophobic acceptor binding pocket. The side chain is about 5 Å above the hydrophobic trichothecene backbone. Changing this residue to glutamine maintains a residue with approximately the same volume but with much greater polarity. The introduction of the polar glutamine in the place of the hydrophobic phenylalanine eliminates enzymatic activity as measured in the coupled-continuous enzymatic assay with DON as a substrate. This, along with the fact that this residue is a conserved Phe in all UGTs that have activity towards DON, highlights the importance of this residue as a component of the acceptor binding pocket.

Role of Gln 143. Gln 143 is located on a loop in the acceptor binding pocket. The $O_ε$ oxygen of Gln 143 is 3.5 Å from the C6 oxygen of the glucose moiety on U2F. Even though this is somewhat on the long-side for a substantial hydrogen bond this side chain appears to play an important role in substrate binding. The Q143A substitution does not demonstrate activity in the coupled-continuous enzymatic assay with DON as a substrate.

Role of Ser 203. Ser 203 is located on the bottom of the α-helix in the back of the acceptor binding pocket adjacent to Gln 202. This side chain was changed to alanine to examine the role of a polar residue in this position. The $K_M$ value of the S203A mutant is similar to that of WT Os79. In order determine if a small residue is important at this position, the S203L substitution was created. There is a 10-fold increase in the $K_M$ of the S203L mutant but no change in $k_{cat}$, indicating that a bulkier residue at this position might hinder DON association or disassociation from the active site. The hydroxyl of S203 is 6.7 Å away from the closest carbon of DON (C4) and given that the change to an alanine has little effect it appears unlikely that it interacts directly with the substrate. It is more likely that a small residue is required at position 203 to allow Gln 202 to maintain a productive orientation. The 5-fold decrease in $K_M$ as a result of the Q202L mutation illustrates the importance of that side chain. This suggests that the S203L mutation might prompt a change in the position of Gln 202 that could increase the $K_M$ for DON.

Role of Ala 384. Ala 384 is positioned on a loop in the acceptor binding pocket about 5 Å from C3 of DON. To examine whether a hydrophobic residue at this position is important for activity this residue was changed to a serine. The $K_M$ value of the A384S mutant is similar to that of WT Os79. Similar to Ser 203, this appears to be a second sphere residue, where changes in polarity appear to have little influence on activity towards DON.

Structure of Os79 Q202A and Os79 H122A/L123A proteins. The kinetic measurements with a variety of trichothecene accepters discussed above revealed that the active site of Os79 is unable to accommodate the C4 acetyl group of trichothecene substrates. The preceding mutations indicate the importance of the helix that carries Phe 199, Gln 202, and Ser 203 where this α-helix is opposite and slightly above C4, C15, and C8 of the trichothecene. Inspection of the acceptor binding pocket revealed that His 122 and Leu 123 are opposite but below Phe 199, Gln 202, and Ser 203, with His 122 positioned only 4.2 Å away from C4. It is unlikely that 4.2 Å leaves sufficient space to accommodate an acetyl group. Although Leu 123 is positioned further from C4, its close proximity to C15 and C8 was viewed as a potential issue if the substrate needed to shift slightly in the active site to accommodate the acetyl moiety on C4. Consequently, His 122 and Leu 123 were simultaneously targeted for mutagenesis. Initially four amino acid substitutions provided Os79 the ability to glycosylate T-2 toxin as measured by an endpoint assay and analyzed by LC-MS/MS as described herein. These were the single substitutions of Q202L, Q202A, and Q202V, and the double substitution of H122A/L123G. The catalytic efficiency and $K_M$ values of Os79 H122A/L123G are $5.08 \times 10^2$ $s^{-1}$ $M^{-1}$ and 512 µM with T-2 toxin as a substrate and 1.99 $10^2$ $s^{-1}$ $M^{-1}$ and 2512 µM with DON as a substrate. Activity for Os79 Q202 with T-2 toxin as a substrate was not detected with the assay used in this example, possibly due to a very high $K_M$. Os79 H122A/L123G was largely insoluble. Based on these findings, Os79 H122A/L123A was expressed and purified. Changing Leu 123 to an alanine instead of glycine improved the solubility of the protein. The catalytic efficiency of the H122A/L123A mutant with T-2 as a substrate is $1.71 \times 10^3$, which is a 3.5-fold increase over WT. The $K_M$ value of 926 µM is similar to the H122A/L123G mutant. To improve the $K_M$, the H122A/L123A substitutions were combined with the Q202A substitution to make Os79 H122A/L123A/Q202A. The $K_M$ of the triple substitution with T-2 as a substrate is 89 µM and the catalytic efficiency is $2.84 \times 10^4$, these values represent a 10-fold decrease in $K_M$ and a 20-fold increase in catalytic efficiency compared to the H122A/L123A double mutant. Similar kinetic parameters are observed with DAS as a substrate. The $K_M$ of the H122A/L123A/Q202A triple mutant with 4-ANIV as a substrate is 501 µM, which is a 5.5-fold increase compared with T-2 toxin and DAS. Interestingly, the $K_M$ value of the H122A/L123A/Q202A triple mutant with DON as a substrate is 1202 µM, and the catalytic efficiency is 7.4×10$^2$, these values represent a 20-fold increase and 23-fold decrease respectively compared to WT. It is clear that although Os79 H122A/L123A/Q202A is capable of glycosylating a broader range of substrates than WT Os79, the triple substitution comes at the cost of decreasing the catalytic efficiency with DON as a substrate. Given the observation that the Q202L substitution decreases the $K_M$ for WT Os79 with respect to DON as a substrate, Os79 H122A/L123A/Q202L was made in an attempt to produce an enzyme with intermediate $K_M$ values for both DON and T-2 toxin. The $K_M$ values for Os79 H122A/L123A/Q202L are 118, 261, and 88 µM for T-2 toxin, DON, and 4-ANIV respectively.

The mutations all suggest that the volume of the active site of Os79 is an important determinant in broadening specificity by allowing the acceptor binding pocket to accommodate the C4 acetyl group. However, it could be possible that the mutations cause a structural change in the acceptor binding pocket. To address this question, the structures of Os79 H122A/L123A (PDB: 6BK2) and Os79 Q202A (PDB: 6BK0) were determined in the presence of UDP to a resolution of 1.47 Å and 1.29 Å respectively (Table 3). These structures show that the mutations result in very little change in the overall structures of the protein. The 50 residues that line and surround the acceptor binding pocket of the Os79 Q202A and H122A/L123A structures aligned to the corresponding residues of the Os79 WT structure with an rmsd of 0.12 and 0.16 Å respectively for structurally equivalent α-carbons. This indicates that the framework of the acceptor binding pockets of these proteins are almost identical to the WT enzyme. The main difference is the size of the trichothecene binding pocket. The H122A/L123A and Q202A mutations increase the volume of the active site. Specifically, these substitutions open up the side of the active site that accommodates the C4 acetyl group. This shows that the broad specificity is sanctioned by the general hydrophobicity and volume of the acceptor cavity, which affords the C4 acetyl group enough space to allow toxins such at 4-ANIV, DAS, and T-2 to bind.

As shown here, the wild-type trichothecene UDP-glucosyltransferase from rice, Os79, has a broad specificity that can modify substrates that differ in molecular weight by a factor of 1.8 (isotrichodermol and HT-2 toxin; 250.3 and 424.5 respectively) with catalytic efficiencies over $1 \times 10^4$ s$^{-1}$ M$^{-1}$. The wild-type enzyme is unable to glycosylate T-2 toxin and yet it readily modifies HT-2, which compared to T-2 is deacetylated at the C4-position. Indeed, as demonstrated herein, the wild-type enzyme is unable to accommodate substrates that are substituted at the C4 position.

The three dimensional structure of the product complex (Os79.UDP.D3G) in combination with the structure of trichothecene bound to Os79 revealed that the acceptor pocket is mostly hydrophobic and includes only a few residues capable of forming hydrogen bonds. Mutagenesis of these polar residues that might interact with the trichothecene substrate had small effects on $k_{cat}$ and $K_M$, whereas mutagenesis of Phe 199 to a glutamine eliminated activity. These observations confirmed that the hydrophobicity and volume of the active site are primary factors in substrate specificity. Based on this structural knowledge, the volume of the active site was increased by mutagenesis with the consequence that Os79 H122A/L123A showed excellent activity towards T-2 toxin but reduced activity towards DON. Addition of the Q202L substitution created an enzyme that is a compromise which allows essentially equivalent activity towards both DON and T-2 toxin. The broad specificity of Os79 H122A/L123A/Q202L, as well as other mutations disclosed herein, makes it extremely useful for incorporation in transgenic plants that are susceptible to infection of both T-2 toxin and DON producing *Fusarium* species, like maize (*F. sporotrichioides* and *F. graminearum*), oat (*F. langsethiae* and *F. culmorum*), or potatoes (*F. sambucinum* and *F. graminearum*) (see Example 12, below).

Example 10

UGT Sequences from Additional Species

The gene for the wild-type (WT) HvUGT13248 was amplified by PCR from barley genomic DNA using the forward primer 5'-ATGGAGACCACGGTCACC-3' (SEQ ID NO:44) and the reverse primer 5'-TTATATTGAC-GAATACTTGGTAGCGAATT-3' (SEQ ID NO:45). The resulting product was introduced into the plasmid pKLD116 as described above for Os79. The H132A/L133A mutation was introduced to the WT gene using a single primer, PCR based method based on "Quikchange" mutagenesis (Chen, et al., supra; van den Ent and Lowe, supra). The following primer was used: 5'-CCCGTGCGCGTGCTGGTGTAC-GACGCTGCGGCGGC GTGGGCACGGCGGGTG-GCACA-3' (SEQ ID NO:43).

HvUGT13248 WT (DNA sequence SEQ ID NO:19, protein sequence SEQ ID NO:20) and H132A/L1233A (DNA sequence SEQ ID NO:21, protein sequence SEQ ID NO:22) were overexpressed and purified using the same procedure as described above for Os79 with the exception that MBP was not cleaved from HvUGT13248. HvUGT13248 WT and H132A/L133A activity with different trichothecene substrates was determined with an end-point assay. The procedure for this activity assay was identical to the coupled assay performed with Os79 and described above with the exception that only a single, high concentration (~2 mM) of toxin was used and the final enzyme concentration was around 50 µM. HvUGT13248 WT exhibited no activity above the control with T-2 toxin as the substrate. HvUGT13248 H132A/L133A exhibited clear activity above the control with T-2 toxin as the substrate. Both enzymes exhibited activity with DON as the substrate.

Example 11

Sequence Alignments and Structural Predictions for UGTs that Exhibit DON UDP-Glucosyltransferase Activity Eight wild-type UDP-glucosyltransferases including Os79 have been shown to exhibit activity towards DON as demonstrated by introduced resistance in yeast and isolation of the reaction product for Os79 and HvUGT13248: UDP-glycosyltransferase superfamily protein from *Arabidopsis thaliana* (Schweiger, et al., *Mol. Plant Microbe Interact.* 23:977-986, 2010; DNA sequence SEQ ID NO:23; protein sequence SEQ ID NO:24), DON-glucosyltransferase 1 from *Arabidopsis thaliana* (Schweiger, et al., 2010, supra; Schweiger, et al., *Mol. Plant Microbe Interact.* 26:781-792, 2013; Poppenberger, et al., *J. Biol. Chem.* 278:47905-47914, 2003; DNA sequence SEQ ID NO:25; protein sequence SEQ ID NO:26), UDP-glucosyl transferase 73C6 from *Arabidopsis thaliana* (Schweiger, et al., 2010, supra; DNA sequence SEQ ID NO:27; protein sequence SEQ ID NO:28), predicted crocetin glucosyltransferase 2-like isoform X1 from *Brachypodium distachyon* (Schweiger, et al., 2013, supra; DNA sequence SEQ ID NO:29; protein sequence SEQ ID NO:30), Os79 (Wetterhorn, et al., *Biochemistry* 55:6175-6186, 2016; Michlmayr, et al., *Toxins* (Basel) 21:2685-2700, 2-15; Schweiger, et al., 2013, supra; codon optimized DNA sequence SEQ ID NO:1; protein sequence SEQ ID NO:2, WT DNA sequence SEQ ID NO:46), hypothetical protein from *Sorghum bicolor* (sorghum) (Schweiger, et al., 2013, supra; DNA sequence SEQ ID NO:31; protein sequence SEQ ID NO:32), predicted UDP-glycosyltransferase 74E2-like from *Brachypodium distachyon* (Schweiger, et al., 2013, supra; DNA sequence SEQ ID NO:33; protein sequence SEQ ID NO:34), and *Hordeum vulgare* subsp. *vulgare* UDP-glucosyltransferase HvUGT13248 from *Hordeum vulgare* subsp. *vulgare* (domesticated barley; Schweiger, et al., 2013, supra; DNA sequence SEQ ID NO:19; protein sequence SEQ ID NO:20). All of these enzymes belong to the glucosyltransferase family of proteins and based on sequence similarity are predicted to exhibit a GT-B fold (shown to be true for Os79). Molecular modeling shows that all of these enzymes will have an active site architecture closely related to that observed in Os79. This means that the active site architecture as defined above exhibits an rms difference of less than 2 Å from that observed in Os79 for the structurally equivalent alpha carbon atoms surrounding the active site. The amino acid side chains that line the active site pocket in Os79 and these related enzymes are similar, which is consistent with their specificity towards DON. Even though the sequence identity might be as low as ~30%, the active site architecture (structural mechanism and specificity) is conserved. It is widely accepted that parallel changes within an enzyme family will (to a first approximation) produce the same results.

Figure 2:
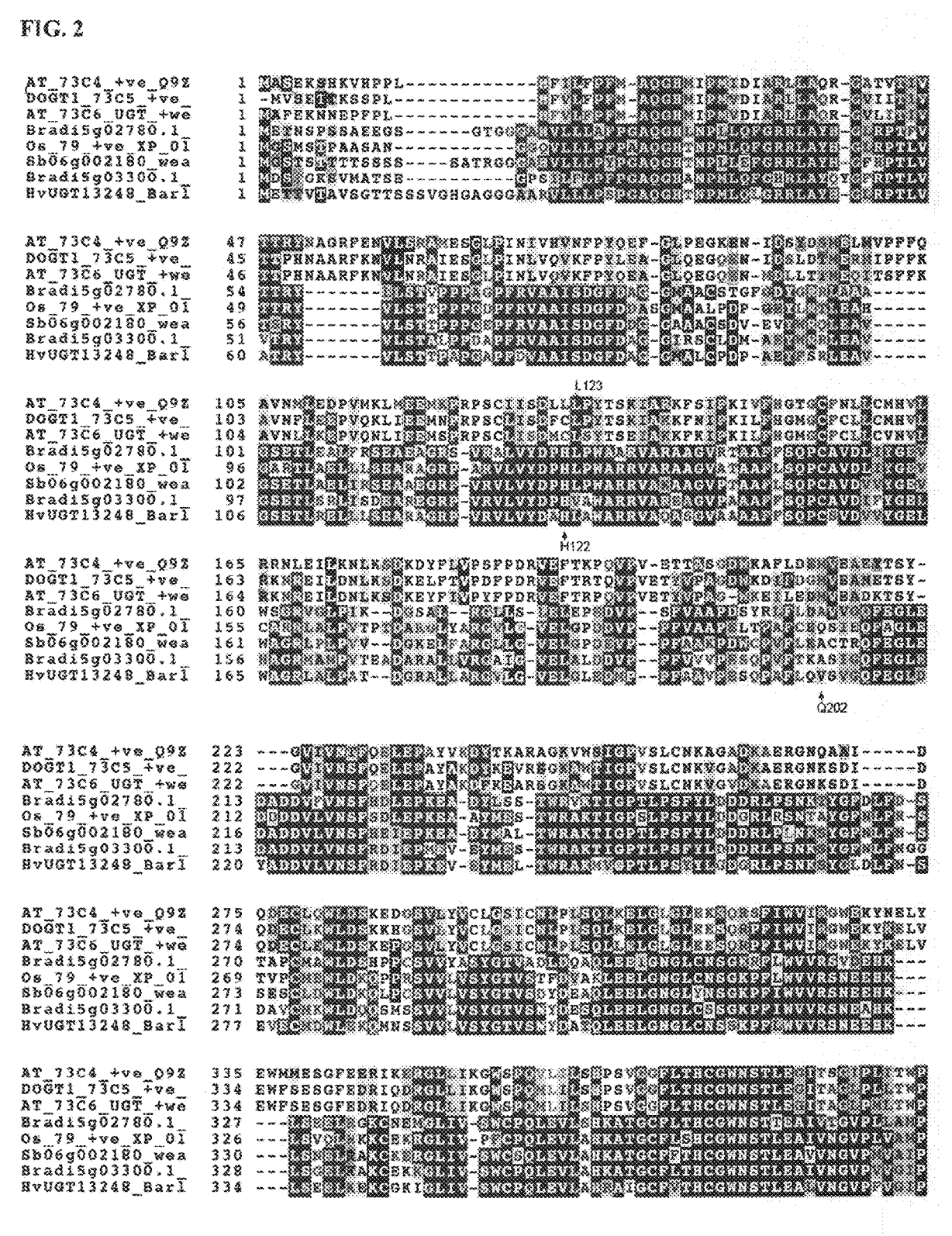

Clustal alignment of the amino acid sequences for these enzymes is shown in FIG. 2. The key for the sequence identifiers is shown in Table 4. This shows that the residues in those enzymes that are equivalent to H122 and L123 in Os79 are similar to those in Os79 and are inconsistent with activity towards T-2 in those wild-type enzymes. Thus the Clustal and structural alignment for H122 and L123 in Os79 agrees, even for those orthologs with low sequence similarity. The corresponding amino acids in these enzymes is shown in Table 5.

TABLE 4

| Sequence Acronym in FIG. 1 and Table 3 | Sequence Identifier | Location |
| --- | --- | --- |
| Os_79_+ve_XP_01 | XP_015635481.1 GI: 1002262256 | ncbi.nlm.nih.gov/protein/1002262256/ |
| Sb06g002180_wea | XM_002447461.1 | ncbi.nlm.nih.gov/gene/8067747 |
| HvUGT13248_Barl | GU170355.1 | ncbi.nlm.nih.gov/nuccore/289188049 |
| Bradi5g03300.1_ | XP_010239695.1 | ncbi.nlm.nih.gov/protein/XP_010239695.1 |
| Bradi5g02780.1_ | XP_003581017.1 | ncbi.nlm.nih.gov/protein/XP_003581017.1 |
| AT_73C6_UGT_+we | NP_181217.1 | ncbi.nlm.nih.gov/protein/NP_181217.1 |
| DOGT1_73C5_+ve_ | NP_181218.1 | ncbi.nlm.nih.gov/protein/15228037?report=fasta |
| AT_73C4_+ve_Q9Z | NP_181215.1 | ncbi.nlm.nih.gov/protein/15228033?report=fasta |

TABLE 5

| Enzyme | His122/L123 | Percent Sequence Identity and Similarity to Os79 |
| --- | --- | --- |
| Os_79_+ve_XP_01 | H122 L123 | 100 |
| Sb06g002180_wea | H128 L129 | 73, 83 |
| HvUGT13248_Barl | H132 L133 | 73, 83 |

TABLE 5-continued

| Enzyme | His122/L123 | Percent Sequence Identity and Similarity to Os79 |
| --- | --- | --- |
| Bradi5g03300.1_ | H123 V124 | 70, 80 |
| Bradi5g02780.1_ | H127 L128 | 70, 78 |
| AT_73C6_UGT_+we | C132 L132 | 30, 47 |
| DOGT1_73C5_+ve_ | C130 L131 | 30, 47 |
| AT_73C4_+ve_Q9Z | L132 L133 | 29, 46 |

The Clustal and structural alignment for Q202 in Os79 do not completely agree for the orthologs with low sequence similarity such that prediction of the corresponding residue to Q202 based on sequence alone is inaccurate. The structurally equivalent positions are shown in Table 6 based on homology models.

TABLE 6

| Enzyme | Residue No. Equiv. to Q202 in Os79 (Clustal) | Residue No. Equiv. to Q202 in Os79 (structural align. based on predicted models except for Os79) | Percentage Seq. Identity and Similarity to Os79 |
| --- | --- | --- | --- |
| Os_79_+ve_XP_01 | Q202 | Q202 | 100 |
| Sb06g002180_wea | A206 | A206 | 73, 83 |
| HvUGT13248_Barl | V210 | V210 | 73, 83 |
| Bradi5g03300.1_ | A203 | A203 | 70, 80 |
| Bradi5g02780.1 | A203 | A203 | 70, 78 |
| AT_73C6_UGT_+we | M213 | I209 | 30, 47 |
| DOGT1_73C5_+ve_ | M213 | I209 | 30, 47 |
| AT_73C4_+ve_Q9Z | M214 | F210 | 29, 46 |

Example 12

Transgenic Plants Incorporating the Disclosed Sequences

It has previously been shown that introduction of the barley glucosyltransferase gene (HvUGT13248) into wheat confers resistance to fungal head blight caused by *Fusarium graminearum* (Li, et al., *Mol. Plant Microbe Interact.* 28:1237-1246, 2015; "Li"). However, as detailed herein above, the barley glucosyltransferase gene (HvUGT13248) does not have activity towards T-2 toxin or DAS. Thus introduction of a variant of HvUGT13248, or any of the other variant sequences disclosed herein that have been shown to glycosylate T-2 toxin into a plant will provide such a plant with resistance to fungal species that synthesize T-2 and related toxins. Likewise, introduction of the Os79 variants described herein, as well as other variant sequences disclosed herein, into a plant, for example maize, oat, wheat, potatoes or barley, will result in the same or better protection against FHB caused by *Fusarium graminearum* and *Fusarium* species that synthesize T-2 toxin, due to the higher enzymatic activity of these variant sequences towards DON or T-2 toxin compared to that of HvUGT13248. Furthermore, the type II resistance correlates with the enzymatic activity, and hence Os79 variants, as well as the other variants disclosed herein, will provide more resistance due to their higher enzymatic activity. This is because trichothecene mycotoxins are known virulence factors for infection where reduction of levels of active toxin lead to lower fungal infection (Wu, et al., *Curr. Drug Metab.* 14:641-660, 2013; Muhitch, et al., *Plant Sci.* 157:201-207, 2000; Proctor, et al., *Mol. Plant Microbe Interact.* 8:593-601, 1995).

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more."

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

While the disclosure has been described in connection with specific embodiments thereof, it will be understood that the present disclosure is capable of further modifications by one of skill in the art. It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. The present disclosure is therefore intended to encompass any variations, uses, or adaptations of the invention following, in general, the principles of the invention and including such departures from the present disclosure as come within known or customary practice within the art to which the invention pertains and as may be applied to the essential features herein before set forth.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications, patents, patent publications, and nucleic acid and amino acid sequences cited are incorporated by reference herein in their entirety for all purposes.

What is claimed is:

1. A polynucleotide comprising a DNA sequence encoding a modified UDP-glycosyltransferase polypeptide, said polypeptide comprising at least two mutations relative to a wild-type UDP glycosyltransferase polypeptide, wherein the mutation renders the modified UDP glycosyltransferase polypeptide capable of glycosylating T-2 toxin, diacetoxyscirpenol (DAS), 4-acetyl-NIV (4-ANIV) or 4,15-diacetyl-NIV (4,15-di-ANIV) from *Fusarium*, wherein said modified UDP glycosyltransferase polypeptide comprises a mutation at positions corresponding to amino acids 122 and 123 of SEQ ID NO:2.

2. The polynucleotide of claim 1, wherein said modified UDP glycosyltransferase polypeptide comprises the amino acid sequence of SEQ ID NO:4, SEQ ID NO:6 or SEQ ID NO:22.

3. The polynucleotide of claim 1, wherein said modified UDP glycosyltransferase polypeptide comprises at least three mutations relative to a wild-type UDP-glycosyltransferase polypeptide, and wherein said modified UDP glycosyltransferase polypeptide comprises a mutation at positions corresponding to amino acids 122, 123 and 202 of SEQ ID NO:2.

4. The polynucleotide of claim 3, wherein said modified UDP glycosyltransferase polypeptide comprises the amino acid sequence of SEQ ID NO:8 or SEQ ID NO:10.

5. The polynucleotide of claim 1, wherein said polynucleotide is operably linked to a regulatory element.

6. The polynucleotide of claim 3, wherein said regulatory element is a heterologous regulatory element.

7. The polynucleotide of claim 6, wherein said regulatory element is a promoter.

8. The polynucleotide of claim 7, wherein said promoter is functional in a plant.

9. The polynucleotide of claim 7, wherein said promoter is an inducible promoter.

10. A polypeptide encoded by the polynucleotide of claim 1.

11. The polypeptide of claim 10, wherein said polynucleotide encodes the amino acid sequence of SEQ ID NO:4, SEQ ID NO:6, SEQ ID NO:8, SEQ ID NO:10 or SEQ ID NO:22.

12. The polypeptide of claim 11, wherein said polynucleotide is encoded by the nucleic acid sequence of SEQ ID NO:3, SEQ ID NO:5, SEQ ID NO:7, SEQ ID NO:9 or SEQ ID NO:21.

13. A plant, plant part, cell, or seed comprising the polynucleotide of claim 1.

14. The plant, plant part, cell, or seed of claim 13, defined as a monocotyledonous plant, seed, cell, or plant part.

15. The plant, plant part, cell, or seed of claim 14, wherein said monocotyledonous plant is selected from the group consisting of: corn, wheat, rice, barley, oats and sorghum.

16. The plant, plant part, cell, or seed of claim 13, defined as a dicotyledonous plant, seed, cell, or plant part.

17. The plant, plant part, cell, or seed of claim 16, wherein said dicotyledonous plant is selected from the group consisting of: soybean, alfalfa, sunflower, cotton, canola, sweet potato, tomato, banana, curcubits, peppers and sugar beet.

18. A method of increasing the resistance of a plant to *Fusarium* infection, comprising expressing in said plant the polynucleotide of claim 1.

19. The method of claim 18, wherein said plant is defined as a monocotyledonous plant.

20. The method of claim 18, wherein said plant is defined as a dicotyledonous plant.

21. The method of claim 18, comprising transforming said plant with said polynucleotide and regenerating the plant therefrom.

22. The method of claim 18, comprising self-pollinating a parent plant comprising said polynucleotide with itself or crossing a parent plant comprising said polynucleotide with a second plant to obtain the plant in which resistance to *Fusarium* infection is increased.

23. A method of increasing the resistance of a plant to *Fusarium* infection, comprising modifying a UDP-glycosyltransferase polypeptide of said plant, wherein said polypeptide comprises:

a) at least a first mutation relative to a wild-type UDP glycosyltransferase polypeptide, and wherein said modified UDP glycosyl transferase polypeptide comprises a mutation at a position corresponding to amino acid 202 of SEQ ID NO:2;
b) at least two mutations relative to a wild-type UDP glycosyltransferase polypeptide, and wherein said modified UDP glycosyl transferase polypeptide comprises a mutation at positions corresponding to amino acids 122 and 123 of SEQ ID NO:2; or
c) at least three mutations relative to a wild-type UDP-glycosyltransferase polypeptide, and wherein said modified UDP glycosyltransferase polypeptide comprises a mutation at positions corresponding to amino acids 122, 123 and 202 of SEQ ID NO:2.

24. The method of claim 23, wherein said modifying comprises site-specific mutagenesis.

25. The method of claim 24, wherein said site-specific mutagenesis comprises the use of single primer, zinc finger nucleases (ZFN), TALEN, or CRISPR technology.

26. A polynucleotide comprising a DNA sequence encoding a modified UDP-glycosyltransferase polypeptide, said polypeptide comprising at least a first mutation relative to a wild-type UDP glycosyltransferase polypeptide, wherein the mutation renders the modified UDP glycosyltransferase polypeptide capable of glycosylating T-2 toxin, diacetoxyscirpenol (DAS), 4-acetyl-NIV (4-ANIV) or 4,15-diacetyl-NIV (4,15-di-ANIV) from *Fusarium*, wherein said modified UDP glycosyl transferase polypeptide comprises a mutation at a position corresponding to amino acid 202 of SEQ ID NO:2.

27. The polynucleotide of claim 26, wherein said modified UDP glycosyltransferase polypeptide comprises the amino acid sequence of SEQ ID NO:12, SEQ ID NO:14 or SEQ ID NO:16.

28. A polypeptide encoded by the polynucleotide of claim 26.

29. The polypeptide of claim 28, wherein said polynucleotide encodes the amino acid sequence of SEQ ID NO:12, SEQ ID NO:14, or SEQ ID NO:16.

30. The polypeptide of claim 29, wherein said polynucleotide is encoded by the nucleic acid sequence of SEQ ID NO:11, SEQ ID NO:13, or SEQ ID NO:15.

31. A plant, plant part, cell, or seed comprising the polynucleotide of claim 26.

* * * * *

SEQUENCE LISTING

```
<160> NUMBER OF SEQ ID NOS: 53

<210> SEQ ID NO 1
<211> LENGTH: 1398
<212> TYPE: DNA
<213> ORGANISM: Oryza sativa

<400> SEQUENCE: 1
atgggctcta tgtccactcc tgccgctagt gcgaacggtg gtcaggtcct tcttttacca      60
ttcccggctg ctcaaggtca caccaatcct atgttacagt ttggaagaag attggcctat     120
cacgggttgc gtccgacttt agtgacaacc aggtatgttc tttccacaac cccacctcct     180
ggagatccct ttcgtgttgc tgctattagc gacggttttg atgatgcctc tggtatggct     240
gcgctaccag atcccggtga atacctgaga actcttgaag cacatggtgc taggacgtta     300
gcagaattgc ttctttcaga agcgagagct ggtagaccag ccagagtttt agtctacgat     360
ccacatctac catgggctag aagagtggca agagcggctg gagttgcaac agccgcattt     420
ctaagtcaac catgtgctgt ggacttgatc tatggcgagg tatgtgctag aagattagca     480
ctaccagtta ccccaacaga tgccagaggt ttatatgcaa gaggtgttct aggtgttgaa     540
ttggggccag atgatgttcc acccttcgta gcagcccctg aattaactcc tgccttctgt     600
gagcaatcta tcgagcagtt tgctggcttg gaggatgacg acgacgtact ggtcaattcc     660
ttctcggatt tggaaccaaa agaagctgct tacatggagt cgacgtggag agcaaagacg     720
```

-continued

```
ataggaccct cactaccatc cttttatctg gacgacggta gattgaggtc gaataccgct     780
tacggtttca atctgtttag gtcaactgtc ccgtgtatgg aatggttgga caaacaacct     840
ccccgttcag tggttttggt gtcatacgga acagtttcta cttttgatgt tgctaaactg     900
gaagaactgg gaaatggatt gtgcaattca ggtaaacctt ttctatgggt cgttagaagt     960
aacgaagagc ataagttgtc tgtccagttg agaagaagt gtgagaaaag aggcttgata    1020
gttccgttct gcccacaatt ggaagtgttg gcccataaag caacaggttg cttcttatct    1080
cattgtggtt ggaacagcac attggaagcc atagtgaatg gagtcccttt agtagctatg    1140
cctcactggg cagatcaacc tactattagc aagtatgtcg aaagtttatg gggcatgggt    1200
gttcgtgtac aattagataa atctgggatc ttacaaagag aagaagtaga aagatgcatt    1260
agggaagtaa tggatgggga tcgtaaagaa gattacagaa ggaacgccac taggttaatg    1320
aagaaagcga agaatcaat gcaagagggc ggctctagtg acaagaacat tgcagagttt    1380
gcagcaaagt attccaat                                                 1398
```

<210> SEQ ID NO 2
<211> LENGTH: 466
<212> TYPE: PRT
<213> ORGANISM: Oryza sativa

<400> SEQUENCE: 2

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Thr Pro Pro Gly Asp Pro Phe
    50                  55                  60

Arg Val Ala Ala Ile Ser Asp Gly Phe Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro His Leu Pro Trp Ala Arg Arg
        115                 120                 125

Val Ala Arg Ala Ala Gly Val Ala Thr Ala Ala Phe Leu Ser Gln Pro
    130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Asp Val Pro Phe Val Ala Ala
            180                 185                 190

Pro Glu Leu Thr Pro Ala Phe Cys Glu Gln Ser Ile Glu Gln Phe Ala
        195                 200                 205

Gly Leu Glu Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
```

```
                        245                 250                 255
Ser Asn Thr Ala Tyr Gly Phe Asn Leu Phe Arg Ser Thr Val Pro Cys
        260                 265                 270

Met Glu Trp Leu Asp Lys Gln Pro Pro Arg Ser Val Val Leu Val Ser
        275                 280                 285

Tyr Gly Thr Val Ser Thr Phe Asp Val Ala Lys Leu Glu Glu Leu Gly
        290                 295                 300

Asn Gly Leu Cys Asn Ser Gly Lys Pro Phe Leu Trp Val Val Arg Ser
305                 310                 315                 320

Asn Glu Glu His Lys Leu Ser Val Gln Leu Arg Lys Lys Cys Glu Lys
                325                 330                 335

Arg Gly Leu Ile Val Pro Phe Cys Pro Gln Leu Glu Val Leu Ala His
            340                 345                 350

Lys Ala Thr Gly Cys Phe Leu Ser His Cys Gly Trp Asn Ser Thr Leu
                355                 360                 365

Glu Ala Ile Val Asn Gly Val Pro Leu Val Ala Met Pro His Trp Ala
        370                 375                 380

Asp Gln Pro Thr Ile Ser Lys Tyr Val Glu Ser Leu Trp Gly Met Gly
385                 390                 395                 400

Val Arg Val Gln Leu Asp Lys Ser Gly Ile Leu Gln Arg Glu Glu Val
                405                 410                 415

Glu Arg Cys Ile Arg Glu Val Met Asp Gly Asp Arg Lys Glu Asp Tyr
            420                 425                 430

Arg Arg Asn Ala Thr Arg Leu Met Lys Lys Ala Lys Glu Ser Met Gln
                435                 440                 445

Glu Gly Gly Ser Ser Asp Lys Asn Ile Ala Glu Phe Ala Ala Lys Tyr
        450                 455                 460

Ser Asn
465

<210> SEQ ID NO 3
<211> LENGTH: 1401
<212> TYPE: DNA
<213> ORGANISM: Oryza sativa

<400> SEQUENCE: 3
atgggctcta tgtccactcc tgccgctagt gcgaacggtg gtcaggtcct tcttttacca     60
ttcccggctg ctcaaggtca caccaatcct atgttacagt ttggaagaag attggcctat    120
cacgggttgc gtccgacttt agtgacaacc aggtatgttc tttccacaac cccacctcct    180
ggagatccct ttcgtgttgc tgctattagc gacggttttg atgatgcctc tggtatggct    240
gcgctaccag atcccggtga atacctgaga actcttgaag cacatggtgc taggacgtta    300
gcagaattgc ttctttcaga agcgagagct ggtagaccag ccagagtttt agtctacgat    360
ccagcgggcc catgggctag aagagtggca agagcggctg agttgcaac agccgcattt    420 ctaagtcaac catgtgctgt ggacttgatc tatggcgagg tatgtgctag aagattagca    480
ctaccagtta ccccaacaga tgccagaggt ttatatgcaa gaggtgttct aggtgttgaa    540 tggggccag atgatgttcc acccttcgta gcagcccctg aattaactcc tgccttctgt    600
gagcaatcta tcgagcagtt tgctggcttg gaggatgacg acgacgtact ggtcaattcc    660
ttctcggatt tggaaccaaa agaagctgct tacatggagt cgacgtggag agcaaagacg    720
ataggaccct cactaccatc cttttatctg gacgacggta gattgaggtc gaataccgct    780
tacggtttca atctgtttag gtcaactgtc ccgtgtatgg aatggttgga caaacaacct    840
```

```
cccgttcag tggttttggt gtcatacgga acagtttcta cttttgatgt tgctaaactg     900
gaagaactgg gaaatggatt gtgcaattca ggtaaacctt ttctatgggt cgttagaagt     960
aacgaagagc ataagttgtc tgtccagttg agaagaagt gtgagaaaag aggcttgata    1020
gttccgttct gcccacaatt ggaagtgttg cccataaag caacaggttg cttcttatct    1080
cattgtggtt ggaacagcac attggaagcc atagtgaatg gagtcccttt agtagctatg    1140
cctcactggg cagatcaacc tactattagc aagtatgtcg aaagtttatg ggcatgggt    1200 gttcgtgtac aattagataa atctgggatc ttacaaagag aagaagtaga aagatgcatt    1260
agggaagtaa tggatgggga tcgtaaagaa gattacagaa ggaacgccac taggttaatg    1320
aagaaagcga agaatcaat gcaagagggc ggctctagtg acaagaacat tgcagagttt    1380
gcagcaaagt attccaatta a                                              1401
```

<210> SEQ ID NO 4
<211> LENGTH: 466
<212> TYPE: PRT
<213> ORGANISM: Oryza sativa

<400> SEQUENCE: 4

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Thr Pro Pro Gly Asp Pro Phe
    50                  55                  60

Arg Val Ala Ala Ile Ser Asp Gly Phe Asp Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro Ala Gly Pro Trp Ala Arg Arg
        115                 120                 125

Val Ala Arg Ala Ala Gly Val Ala Thr Ala Ala Phe Leu Ser Gln Pro
    130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Val Pro Pro Phe Val Ala Ala
            180                 185                 190

Pro Glu Leu Thr Pro Ala Phe Cys Glu Gln Ser Ile Glu Gln Phe Ala
        195                 200                 205

Gly Leu Glu Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
                245                 250                 255

Ser Asn Thr Ala Tyr Gly Phe Asn Leu Phe Arg Ser Thr Val Pro Cys
            260                 265                 270
```

Met Glu Trp Leu Asp Lys Gln Pro Pro Arg Ser Val Leu Val Ser
     275                 280                 285

Tyr Gly Thr Val Ser Thr Phe Asp Val Ala Lys Leu Glu Glu Leu Gly
     290                 295                 300

Asn Gly Leu Cys Asn Ser Gly Lys Pro Phe Leu Trp Val Val Arg Ser
305                 310                 315                 320

Asn Glu Glu His Lys Leu Ser Val Gln Leu Arg Lys Lys Cys Glu Lys
                325                 330                 335

Arg Gly Leu Ile Val Pro Phe Cys Pro Gln Leu Glu Val Leu Ala His
             340                 345                 350

Lys Ala Thr Gly Cys Phe Leu Ser His Cys Gly Trp Asn Ser Thr Leu
         355                 360                 365

Glu Ala Ile Val Asn Gly Val Pro Leu Val Ala Met Pro His Trp Ala
     370                 375                 380

Asp Gln Pro Thr Ile Ser Lys Tyr Val Glu Ser Leu Trp Gly Met Gly
385                 390                 395                 400

Val Arg Val Gln Leu Asp Lys Ser Gly Ile Leu Gln Arg Glu Glu Val
                405                 410                 415

Glu Arg Cys Ile Arg Glu Val Met Asp Gly Asp Arg Lys Glu Asp Tyr
             420                 425                 430

Arg Arg Asn Ala Thr Arg Leu Met Lys Lys Ala Lys Glu Ser Met Gln
         435                 440                 445

Glu Gly Gly Ser Ser Asp Lys Asn Ile Ala Glu Phe Ala Ala Lys Tyr
     450                 455                 460

Ser Asn
465

<210> SEQ ID NO 5
<211> LENGTH: 1401
<212> TYPE: DNA
<213> ORGANISM: Oryza sativa

<400> SEQUENCE: 5

| | | |
|---|---|---|
| atgggctcta tgtccactcc tgccgctagt gcgaacggtg gtcaggtcct tcttttacca | 60 |
| ttcccggctg ctcaaggtca caccaatcct atgttacagt ttggaagaag attggcctat | 120 |
| cacgggttgc gtccgacttt agtgacaacc aggtatgttc tttccacaac cccacctcct | 180 |
| ggagatccct ttcgtgttgc tgctattagc gacggttttg atgatgcctc tggtatggct | 240 |
| gcgctaccag atcccggtga atacctgaga actcttgaag cacatggtgc taggacgtta | 300 |
| gcagaattgc ttctttcaga agcgagagct ggtagaccag ccagagtttt agtctacgat | 360 |
| ccagcggcgc catgggctag aagagtggca agagcggctg gagttgcaac agccgcattt | 420 |
| ctaagtcaac catgtgctgt ggacttgatc tatggcgagg tatgtgctag aagattagca | 480 |
| ctaccagtta ccccaacaga tgccagaggt ttatatgcaa gaggtgttct aggtgttgaa | 540 |
| tggggccag atgatgttcc acccttcgta gcagcccctg aattaactcc tgccttctgt | 600 |
| gagcaatcta tcgagcagtt tgctggcttg gaggatgacg acgacgtact ggtcaattcc | 660 |
| ttctcggatt tggaaccaaa agaagctgct acatggagt cgacgtggag agcaaagacg | 720 |
| ataggaccct cactaccatc ctttatctg gacgacggta gattgaggtc gaataccgct | 780 |
| tacggtttca atctgtttag gtcaactgtc ccgtgtatgg aatggttgga caaacaacct | 840 |
| ccccgttcag tggttttggt gtcatacgga acagttctac ttttgatgt tgctaaactg | 900 |
| gaagaactgg gaaatggatt gtgcaattca ggtaaacctt ttctatgggt cgttagaagt | 960 |

```
aacgaagagc ataagttgtc tgtccagttg agaaagaagt gtgagaaaag aggcttgata    1020
gttccgttct gcccacaatt ggaagtgttg gcccataaag caacaggttg cttcttatct    1080
cattgtggtt ggaacagcac attggaagcc atagtgaatg gagtcccttt agtagctatg    1140
cctcactggg cagatcaacc tactattagc aagtatgtcg aaagtttatg gggcatgggt    1200
gttcgtgtac aattagataa atctgggatc ttacaaagag aagaagtaga aagatgcatt    1260
agggaagtaa tggatgggga tcgtaaagaa gattacagaa ggaacgccac taggttaatg    1320
aagaaagcga agaatcaat gcaagagggc ggctctagtg acaagaacat tgcagagttt    1380
gcagcaaagt attccaatta a                                              1401
```

<210> SEQ ID NO 6
<211> LENGTH: 466
<212> TYPE: PRT
<213> ORGANISM: Oryza sativa

<400> SEQUENCE: 6

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Pro Pro Gly Asp Pro Phe
    50                  55                  60

Arg Val Ala Ala Ile Ser Asp Gly Phe Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro Ala Ala Pro Trp Ala Arg Arg
        115                 120                 125

Val Ala Arg Ala Ala Gly Val Ala Thr Ala Ala Phe Leu Ser Gln Pro
    130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Val Pro Pro Phe Val Ala Ala
            180                 185                 190

Pro Glu Leu Thr Pro Ala Phe Cys Glu Gln Ser Ile Glu Gln Phe Ala
        195                 200                 205

Gly Leu Glu Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
                245                 250                 255

Ser Asn Thr Ala Tyr Gly Phe Asn Leu Phe Arg Ser Thr Val Pro Cys
            260                 265                 270

Met Glu Trp Leu Asp Lys Gln Pro Pro Arg Ser Val Val Leu Val Ser
        275                 280                 285
```

```
Tyr Gly Thr Val Ser Thr Phe Asp Val Ala Lys Leu Glu Glu Leu Gly
        290                 295                 300
Asn Gly Leu Cys Asn Ser Gly Lys Pro Phe Leu Trp Val Val Arg Ser
305                 310                 315                 320
Asn Glu Glu His Lys Leu Ser Val Gln Leu Arg Lys Lys Cys Glu Lys
                325                 330                 335
Arg Gly Leu Ile Val Pro Phe Cys Pro Gln Leu Glu Val Leu Ala His
            340                 345                 350
Lys Ala Thr Gly Cys Phe Leu Ser His Cys Gly Trp Asn Ser Thr Leu
        355                 360                 365
Glu Ala Ile Val Asn Gly Val Pro Leu Val Ala Met Pro His Trp Ala
    370                 375                 380
Asp Gln Pro Thr Ile Ser Lys Tyr Val Glu Ser Leu Trp Gly Met Gly
385                 390                 395                 400
Val Arg Val Gln Leu Asp Lys Ser Gly Ile Leu Gln Arg Glu Glu Val
                405                 410                 415
Glu Arg Cys Ile Arg Glu Val Met Asp Gly Asp Arg Lys Glu Asp Tyr
            420                 425                 430
Arg Arg Asn Ala Thr Arg Leu Met Lys Lys Ala Lys Glu Ser Met Gln
        435                 440                 445
Glu Gly Gly Ser Ser Asp Lys Asn Ile Ala Glu Phe Ala Ala Lys Tyr
    450                 455                 460
Ser Asn
465

<210> SEQ ID NO 7
<211> LENGTH: 1401
<212> TYPE: DNA
<213> ORGANISM: Oryza sativa

<400> SEQUENCE: 7
atgggctcta tgtccactcc tgccgctagt gcgaacggtg gtcaggtcct tcttttacca      60
ttcccggctg ctcaaggtca caccaatcct atgttacagt ttggaagaag attggcctat     120
cacgggttgc gtccgacttt agtgacaacc aggtatgttc tttccacaac cccacctcct     180
ggagatccct ttcgtgttgc tgctattagc gacggttttg atgatgcctc tggtatggct     240
gcgctaccag atcccggtga ataccctgaga actcttgaag cacatggtgc taggacgtta     300
gcagaattgc ttctttcaga agcgagagct ggtagaccag ccagagtttt agtctacgat     360
ccagcggcgc catgggctag aagagtggca agagcggctg gagttgcaac agccgcattt     420
ctaagtcaac catgtgctgt ggacttgatc tatggcgagg tatgtgctag aagattagca     480
ctaccagtta ccccaacaga tgccagaggt ttatatgcaa gaggtgttct aggtgttgaa     540
tggggccag atgatgttcc accttcgta gcagcccctg aattaactcc tgccttctgt     600
gaggcgtcta tcgagcagtt tgctggcttg gaggatgacg acgacgtact ggtcaattcc     660
ttctcggatt tggaaccaaa agaagctgct tacatggagt cgacgtggag agcaaagacg     720
ataggaccct cactaccatc ctttatctg gacgacggta gattgaggtc gaataccgct     780
tacggtttca atctgtttag gtcaactgtc ccgtgtatgg aatggttgga caaacaacct     840
ccccgttcag tggttttggt gtcatacgga acagtttcta cttttgatgt tgctaaactg     900
gaagaactgg gaaatggatt gtgcaattca ggtaaacctt ttctatgggt cgttagaagt     960
aacgaagagc ataagttgtc tgtccagttg agaaagaagt gtgagaaaag aggcttgata    1020
gttccgttct gcccacaatt ggaagtgttg gcccataaag caacaggttg cttcttatct    1080
```

-continued

```
cattgtggtt ggaacagcac attggaagcc atagtgaatg agtccctttg agtagctatg      1140
cctcactggg cagatcaacc tactattagc aagtatgtcg aaagtttatg ggcatgggt      1200 gttcgtgtac aattagataa atctgggatc ttacaaagag aagaagtaga aagatgcatt      1260
agggaagtaa tggatgggga tcgtaaagaa gattacagaa ggaacgccac taggttaatg      1320
aagaaagcga agaatcaat gcaagagggc ggctctagtg acaagaacat tgcagagttt      1380
gcagcaaagt attccaatta a                                                1401
```

<210> SEQ ID NO 8
<211> LENGTH: 466
<212> TYPE: PRT
<213> ORGANISM: Oryza sativa
<400> SEQUENCE: 8

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Pro Pro Gly Asp Pro Phe
    50                  55                  60

Arg Val Ala Ala Ile Ser Asp Gly Phe Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro Ala Ala Pro Trp Ala Arg Arg
        115                 120                 125

Val Ala Arg Ala Ala Gly Val Ala Thr Ala Ala Phe Leu Ser Gln Pro
    130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Asp Val Pro Pro Phe Val Ala Ala
            180                 185                 190

Pro Glu Leu Thr Pro Ala Phe Cys Glu Ala Ser Ile Glu Gln Phe Ala
        195                 200                 205

Gly Leu Glu Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
                245                 250                 255

Ser Asn Thr Ala Tyr Gly Phe Asn Leu Phe Arg Ser Thr Val Pro Cys
            260                 265                 270

Met Glu Trp Leu Asp Lys Gln Pro Pro Arg Ser Val Val Leu Val Ser
        275                 280                 285

Tyr Gly Thr Val Ser Thr Phe Asp Val Ala Lys Leu Glu Glu Leu Gly
    290                 295                 300

Asn Gly Leu Cys Asn Ser Gly Lys Pro Phe Leu Trp Val Val Arg Ser
```

Asn Glu Glu His Lys Leu Ser Val Gln Leu Arg Lys Lys Cys Glu Lys
305                 310                 315                 320

Arg Gly Leu Ile Val Pro Phe Cys Pro Gln Leu Glu Val Leu Ala His
            325                 330                 335

Lys Ala Thr Gly Cys Phe Leu Ser His Cys Gly Trp Asn Ser Thr Leu
        340                 345                 350

Glu Ala Ile Val Asn Gly Val Pro Leu Val Ala Met Pro His Trp Ala
    355                 360                 365

Asp Gln Pro Thr Ile Ser Lys Tyr Val Glu Ser Leu Trp Gly Met Gly
370                 375                 380

Val Arg Val Gln Leu Asp Lys Ser Gly Ile Leu Gln Arg Glu Glu Val
        385                 390                 395                 400

Glu Arg Cys Ile Arg Glu Val Met Asp Gly Asp Arg Lys Glu Asp Tyr
            405                 410                 415

Arg Arg Asn Ala Thr Arg Leu Met Lys Lys Ala Lys Glu Ser Met Gln
        420                 425                 430

Glu Gly Gly Ser Ser Asp Lys Asn Ile Ala Glu Phe Ala Ala Lys Tyr
    435                 440                 445

Ser Asn
450                 455                 460

465

<210> SEQ ID NO 9
<211> LENGTH: 1401
<212> TYPE: DNA
<213> ORGANISM: Oryza sativa

<400> SEQUENCE: 9
atgggctcta tgtccactcc tgccgctagt gcgaacggtg gtcaggtcct tcttttacca        60
ttcccggctg ctcaaggtca caccaatcct atgttacagt ttggaagaag attggcctat       120
cacgggttgc gtccgacttt agtgacaacc aggtatgttc tttccacaac cccacctcct       180
ggagatccct ttcgtgttgc tgctattagc gacggttttg atgatgcctc tggtatggct       240
gcgctaccag atcccggtga atacctgaga actcttgaag cacatggtgc taggacgtta       300
gcagaattgc ttcttcaga agcgagagct ggtagaccag ccagagtttt agtctacgat       360
ccagcggcgc catgggctag aagagtggca agagcggctg agttgcaac agccgcattt       420
ctaagtcaac catgtgctgt ggacttgatc tatggcgagg tatgtctag aagattagca       480
ctaccagtta ccccaacaga tgccagaggt ttatatgcaa gaggtgttct aggtgttgaa       540
ttggggccag atgatgttcc acccttcgta gcagcccctg aattaactcc tgccttctgt       600
gagctgtcta tcgagcagtt tgctggcttg gaggatgacg acgacgtact ggtcaattcc       660
ttctcggatt tggaaccaaa agaagctgct tacatggagt cgacgtggag agcaaagacg       720
ataggaccct cactaccatc ctttatctg acgacggta gattgaggtc gaataccgct       780
tacggtttca atctgtttag gtcaactgtc ccgtgtatgg aatggttgga caaacaacct       840
ccccgttcag tggttttggt gtcatacgga acagtttcta cttttgatgt tgctaaactg       900
gaagaactgg gaaatggatt gtgcaattca ggtaaacctt ttctatgggt cgttagaagt       960
aacgaagagc ataagttgtc tgtccagttg agaaagaagt gtgagaaaag aggcttgata      1020
gttccgttct gcccacaatt ggaagtgttg gcccataaag caacaggttg cttcttatct      1080
cattgtggtt ggaacagcac attggaagcc atagtgaatg gagtcccttt agtagctatg      1140
cctcactggg cagatcaacc tactattagc aagtatgtcg aaagtttatg gggcatgggt      1200

```
gttcgtgtac aattagataa atctgggatc ttacaaagag aagaagtaga aagatgcatt    1260
agggaagtaa tggatgggga tcgtaaagaa gattacagaa ggaacgccac taggttaatg    1320
aagaaagcga agaatcaat gcaagagggc ggctctagtg acaagaacat tgcagagttt     1380
gcagcaaagt attccaatta a                                              1401
```

<210> SEQ ID NO 10
<211> LENGTH: 466
<212> TYPE: PRT
<213> ORGANISM: Oryza sativa

<400> SEQUENCE: 10

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Thr Pro Pro Gly Asp Pro Phe
    50                  55                  60

Arg Val Ala Ala Ile Ser Asp Gly Phe Asp Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro Ala Ala Pro Trp Ala Arg Arg
        115                 120                 125

Val Ala Arg Ala Ala Gly Val Ala Thr Ala Ala Phe Leu Ser Gln Pro
    130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Asp Val Pro Pro Phe Val Ala Ala
            180                 185                 190

Pro Glu Leu Thr Pro Ala Phe Cys Glu Leu Ser Ile Glu Gln Phe Ala
        195                 200                 205

Gly Leu Glu Asp Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
                245                 250                 255

Ser Asn Thr Ala Tyr Gly Phe Asn Leu Phe Arg Ser Thr Val Pro Cys
            260                 265                 270

Met Glu Trp Leu Asp Lys Gln Pro Pro Arg Ser Val Val Leu Val Ser
        275                 280                 285

Tyr Gly Thr Val Ser Thr Phe Asp Val Ala Lys Leu Glu Glu Leu Gly
    290                 295                 300

Asn Gly Leu Cys Asn Ser Gly Lys Pro Phe Leu Trp Val Val Arg Ser
305                 310                 315                 320

Asn Glu Glu His Lys Leu Ser Val Gln Leu Arg Lys Lys Cys Glu Lys
                325                 330                 335
```

```
Arg Gly Leu Ile Val Pro Phe Cys Pro Gln Leu Glu Val Leu Ala His
                340                 345                 350
Lys Ala Thr Gly Cys Phe Leu Ser His Cys Gly Trp Asn Ser Thr Leu
            355                 360                 365
Glu Ala Ile Val Asn Gly Val Pro Leu Val Ala Met Pro His Trp Ala
370                 375                 380
Asp Gln Pro Thr Ile Ser Lys Tyr Val Glu Ser Leu Trp Gly Met Gly
385                 390                 395                 400
Val Arg Val Gln Leu Asp Lys Ser Gly Ile Leu Gln Arg Glu Glu Val
                405                 410                 415
Glu Arg Cys Ile Arg Glu Val Met Asp Gly Asp Arg Lys Glu Asp Tyr
            420                 425                 430
Arg Arg Asn Ala Thr Arg Leu Met Lys Lys Ala Lys Glu Ser Met Gln
        435                 440                 445
Glu Gly Gly Ser Ser Asp Lys Asn Ile Ala Glu Phe Ala Ala Lys Tyr
    450                 455                 460
Ser Asn
465

<210> SEQ ID NO 11
<211> LENGTH: 1401
<212> TYPE: DNA
<213> ORGANISM: Oryza sativa

<400> SEQUENCE: 11
```

| | | | | | |
|---|---|---|---|---|---|
| atgggctcta | tgtccactcc | tgccgctagt | gcgaacggtg | gtcaggtcct | tcttttacca | 60 |
| ttcccggctg | ctcaaggtca | caccaatcct | atgttacagt | ttggaagaag | attggcctat | 120 |
| cacgggttgc | gtccgacttt | agtgacaacc | aggtatgttc | tttccacaac | cccacctcct | 180 |
| ggagatccct | tcgtgttgc | tgctattagc | gacggttttg | atgatgcctc | tggtatggct | 240 |
| gcgctaccag | atcccggtga | ataccctgaga | actcttgaag | cacatggtgc | taggacgtta | 300 |
| gcagaattgc | ttcttcaga | agcgagagct | ggtagaccag | ccagagtttt | agtctacgat | 360 |
| ccacatctac | catgggctag | aagagtggca | agagcggctg | gagttgcaac | agccgcattt | 420 |
| ctaagtcaac | catgtgctgt | ggacttgatc | tatggcgagg | tatgtgctag | aagattagca | 480 |
| ctaccagtta | ccccaacaga | tgccagaggt | ttatatgcaa | gaggtgttct | aggtgttgaa | 540 |
| ttggggccag | atgatgttcc | acccttcgta | gcagcccctg | aattaactcc | tgccttctgt | 600 |
| gaggcgtcta | tcgagcagtt | tgctggcttg | gaggatgacg | acgacgtact | ggtcaattcc | 660 |
| ttctcggatt | tggaaccaaa | agaagctgct | tacatggagt | cgacgtggag | agcaaagacg | 720 |
| ataggaccct | cactaccatc | cttttatctg | gacgacggta | gattgaggtc | gaataccgct | 780 |
| tacggtttca | atctgtttag | gtcaactgtc | ccgtgtatgg | aatggttgga | caaacaacct | 840 |
| ccccgttcag | tggttttggt | gtcatacgga | acagtttcta | cttttgatgt | tgctaaactg | 900 |
| gaagaactgg | gaaatggatt | gtgcaattca | ggtaaaccct | tctatgggt | cgttagaagt | 960 |
| aacgaagagc | ataagttgtc | tgtccagttg | agaaagaagt | gtgagaaaag | aggcttgata | 1020 |
| gttccgttct | gcccacaatt | ggaagtgttg | gcccataaag | caacaggttg | cttcttatct | 1080 |
| cattgtggtt | ggaacagcac | attggaagcc | atagtgaatg | gagtcccttt | agtagctatg | 1140 |
| cctcactggg | cagatcaacc | tactattagc | aagtatgtcg | aaagtttatg | gggcatgggt | 1200 |
| gttcgtgtac | aattagataa | atctgggatc | ttacaaagag | aagaagtaga | agatgcatt | 1260 |
| agggaagtaa | tggatgggga | tcgtaaagaa | gattacagaa | ggaacgccac | taggttaatg | 1320 |

-continued

```
aagaaagcga aagaatcaat gcaagagggc ggctctagtg acaagaacat tgcagagttt    1380
gcagcaaagt attccaatta a                                               1401
```

<210> SEQ ID NO 12
<211> LENGTH: 466
<212> TYPE: PRT
<213> ORGANISM: Oryza sativa

<400> SEQUENCE: 12

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Thr Pro Pro Gly Asp Pro Phe
    50                  55                  60

Arg Val Ala Ala Ile Ser Asp Gly Phe Asp Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro His Leu Pro Trp Ala Arg Arg
        115                 120                 125

Val Ala Arg Ala Ala Gly Val Ala Thr Ala Ala Phe Leu Ser Gln Pro
130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Asp Val Pro Pro Phe Val Ala Ala
            180                 185                 190

Pro Glu Leu Thr Pro Ala Phe Cys Glu Ala Ser Ile Glu Gln Phe Ala
        195                 200                 205

Gly Leu Glu Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
                245                 250                 255

Ser Asn Thr Ala Tyr Gly Phe Asn Leu Phe Arg Ser Thr Val Pro Cys
            260                 265                 270

Met Glu Trp Leu Asp Lys Gln Pro Pro Arg Ser Val Val Leu Val Ser
        275                 280                 285

Tyr Gly Thr Val Ser Thr Phe Asp Val Ala Lys Leu Glu Glu Leu Gly
    290                 295                 300

Asn Gly Leu Cys Asn Ser Gly Lys Pro Phe Leu Trp Val Val Arg Ser
305                 310                 315                 320

Asn Glu Glu His Lys Leu Ser Val Gln Leu Arg Lys Cys Glu Lys
                325                 330                 335

Arg Gly Leu Ile Val Pro Phe Cys Pro Gln Leu Glu Val Leu Ala His
            340                 345                 350
```

```
Lys Ala Thr Gly Cys Phe Leu Ser His Cys Gly Trp Asn Ser Thr Leu
            355                 360                 365
Glu Ala Ile Val Asn Gly Val Pro Leu Val Ala Met Pro His Trp Ala
    370                 375                 380
Asp Gln Pro Thr Ile Ser Lys Tyr Val Glu Ser Leu Trp Gly Met Gly
385                 390                 395                 400
Val Arg Val Gln Leu Asp Lys Ser Gly Ile Leu Gln Arg Glu Glu Val
                405                 410                 415
Glu Arg Cys Ile Arg Glu Val Met Asp Gly Asp Arg Lys Glu Asp Tyr
            420                 425                 430
Arg Arg Asn Ala Thr Arg Leu Met Lys Lys Ala Lys Glu Ser Met Gln
        435                 440                 445
Glu Gly Gly Ser Ser Asp Lys Asn Ile Ala Glu Phe Ala Ala Lys Tyr
    450                 455                 460
Ser Asn
465

<210> SEQ ID NO 13
<211> LENGTH: 1401
<212> TYPE: DNA
<213> ORGANISM: Oryza sativa

<400> SEQUENCE: 13
atgggctcta tgtccactcc tgccgctagt gcgaacggtg gtcaggtcct tcttttacca        60
ttcccggctg ctcaaggtca caccaatcct atgttacagt ttggaagaag attggcctat       120
cacgggttgc gtccgacttt agtgacaacc aggtatgttc tttccacaac cccacctcct       180
ggagatccct ttcgtgttgc tgctattagc gacggttttg atgatgcctc tggtatggct       240
gcgctaccag atcccggtga atacctgaga actcttgaag cacatggtgc taggacgtta       300
gcagaattgc ttctttcaga agcgagagct ggtagaccag ccagagtttt agtctacgat       360
ccacatctac catgggctag aagagtggca agagcggctg gagttgcaac agccgcattt       420
ctaagtcaac catgtgctgt ggacttgatc tatggcgagg tatgtgctag aagattagca       480
ctaccagtta ccccaacaga tgccagaggt ttatatgcaa gaggtgttct aggtgttgaa       540
ttggggccag atgatgttcc acccttcgta gcagcccctg aattaactcc tgccttctgt       600
gaggtgtcta tcgagcagtt tgctggcttg gaggatgacg acgacgtact ggtcaattcc       660
ttctcggatt tggaaccaaa agaagctgct tacatggagt cgacgtggag agcaaagacg       720
ataggaccct cactaccatc ctttttatctg gacgacggta gattgaggtc gaataccgct       780
tacggtttca atctgtttag gtcaactgtc ccgtgtatgg aatggttgga caaacaacct       840
ccccgttcag tggttttggt gtcatacgga acagtttcta cttttgatgt tgctaaactg       900
gaagaactgg gaaatggatt gtgcaattca ggtaaacctt ttctatgggt cgttagaagt       960
aacgaagagc ataagttgtc tgtccagttg agaaagaagt gtgagaaaag aggcttgata      1020
gttccgttct gcccacaatt ggaagtgttg gcccataaag caacaggttg cttcttatct      1080
cattgtggtt ggaacagcac attggaagcc atagtgaatg gagtcccttt agtagctatg      1140
cctcactggg cagatcaacc tactattagc aagtatgtcg aaagtttatg gggcatgggt      1200
gttcgtgtac aattagataa atctgggatc ttacaaagag aagaagtaga agatgcatt       1260 agggaagtaa tggatgggga tcgtaaagaa gattacagaa ggaacgccac taggttaatg      1320
aagaaagcga agaatcaat gcaagagggc ggctctagtg acaagaacat tgcagagttt       1380
gcagcaaagt attccaatta a                                                 1401
```

<210> SEQ ID NO 14
<211> LENGTH: 466
<212> TYPE: PRT
<213> ORGANISM: Oryza sativa

<400> SEQUENCE: 14

Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Thr Pro Pro Gly Asp Pro Phe
50                  55                  60

Arg Val Ala Ala Ile Ser Asp Gly Phe Asp Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro His Leu Pro Trp Ala Arg Arg
        115                 120                 125

Val Ala Arg Ala Ala Gly Val Ala Thr Ala Ala Phe Leu Ser Gln Pro
130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Asp Val Pro Pro Phe Val Ala Ala
            180                 185                 190

Pro Glu Leu Thr Pro Ala Phe Cys Glu Val Ser Ile Glu Gln Phe Ala
        195                 200                 205

Gly Leu Glu Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
                245                 250                 255

Ser Asn Thr Ala Tyr Gly Phe Asn Leu Phe Arg Ser Thr Val Pro Cys
            260                 265                 270

Met Glu Trp Leu Asp Lys Gln Pro Pro Arg Ser Val Val Leu Val Ser
        275                 280                 285

Tyr Gly Thr Val Ser Thr Phe Asp Val Ala Lys Leu Glu Glu Leu Gly
    290                 295                 300

Asn Gly Leu Cys Asn Ser Gly Lys Pro Phe Leu Trp Val Val Arg Ser
305                 310                 315                 320

Asn Glu Glu His Lys Leu Ser Val Gln Leu Arg Lys Lys Cys Glu Lys
                325                 330                 335

Arg Gly Leu Ile Val Pro Phe Cys Pro Gln Leu Glu Val Leu Ala His
            340                 345                 350

Lys Ala Thr Gly Cys Phe Leu Ser His Cys Gly Trp Asn Ser Thr Leu
        355                 360                 365

Glu Ala Ile Val Asn Gly Val Pro Leu Val Ala Met Pro His Trp Ala

```
                  370              375              380
Asp Gln Pro Thr Ile Ser Lys Tyr Val Glu Ser Leu Trp Gly Met Gly
385                 390                 395                 400

Val Arg Val Gln Leu Asp Lys Ser Gly Ile Leu Gln Arg Glu Glu Val
                405                 410                 415

Glu Arg Cys Ile Arg Glu Val Met Asp Gly Asp Arg Lys Glu Asp Tyr
            420                 425                 430

Arg Arg Asn Ala Thr Arg Leu Met Lys Lys Ala Lys Glu Ser Met Gln
        435                 440                 445

Glu Gly Gly Ser Ser Asp Lys Asn Ile Ala Glu Phe Ala Ala Lys Tyr
    450                 455                 460

Ser Asn
465

<210> SEQ ID NO 15
<211> LENGTH: 1401
<212> TYPE: DNA
<213> ORGANISM: Oryza sativa

<400> SEQUENCE: 15
atgggctcta tgtccactcc tgccgctagt gcgaacggtg gtcaggtcct tcttttacca    60
ttcccggctg ctcaaggtca caccaatcct atgttacagt tggaagaag attggcctat    120 cacgggttgc gtccgacttt agtgacaacc aggtatgttc tttccacaac cccacctcct    180
ggagatccct ttcgtgttgc tgctattagc gacggttttg atgatgcctc tggtatggct    240
gcgctaccag atcccggtga atacctgaga actcttgaag cacatggtgc taggacgtta    300
gcagaattgc ttctttcaga agcgagagct ggtagaccag ccagagtttt agtctacgat    360
ccacatctac catgggctag aagagtggca agagcggctg gagttgcaac agccgcattt    420
ctaagtcaac catgtgctgt ggacttgatc tatggcgagg tatgtgctag aagattagca    480
ctaccagtta ccccaacaga tgccagaggt ttatatgcaa gaggtgttct aggtgttgaa    540
ttggggccag atgatgttcc acccttcgta gcagcccctg aattaactcc tgccttctgt    600
gagctgtcta tcgagcagtt tgctggcttg gaggatgacg acgacgtact ggtcaattcc    660
ttctcggatt tggaaccaaa agaagctgct tacatggagt cgacgtggag agcaaagacg    720
ataggaccct cactaccatc ctttatctg gacgacggta gattgaggtc gaataccgct    780
tacggtttca atctgtttag gtcaactgtc ccgtgtatgg aatggttgga caaacaacct    840
ccccgttcag tggttttggt gtcatacgga acagtttcta cttttgatgt tgctaaactg    900
gaagaactgg gaaatggatt gtgcaattca ggtaaacctt ttctatgggt cgttagaagt    960
aacgaagagc ataagttgtc tgtccagttg agaaagaagt gtgagaaaag aggcttgata   1020
gttccgttct gcccacaatt ggaagtgttg gcccataaag caacaggttg cttcttatct   1080
cattgtggtt ggaacagcac attggaagcc atagtgaatg gagtcccttt agtagctatg   1140
cctcactggg cagatcaacc tactattagc aagtatgtcg aaagtttatg gggcatgggt   1200
gttcgtgtac aattagataa atctgggatc ttacaaagag aagaagtaga aagatgcatt   1260
agggaagtaa tggatgggga tcgtaaagaa gattacagaa ggaacgccac taggttaatg   1320
aagaaagcga aagaatcaat gcaagagggc ggctctagtg acaagaacat tgcagagttt   1380
gcagcaaagt attccaatta a                                              1401

<210> SEQ ID NO 16
<211> LENGTH: 466
```

<212> TYPE: PRT
<213> ORGANISM: Oryza sativa

<400> SEQUENCE: 16

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Thr Pro Pro Gly Asp Pro Phe
    50                  55                  60

Arg Val Ala Ala Ile Ser Asp Gly Phe Asp Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro His Leu Pro Trp Ala Arg Arg
        115                 120                 125

Val Ala Arg Ala Ala Gly Val Ala Thr Ala Ala Phe Leu Ser Gln Pro
130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
            165                 170                 175

Leu Gly Val Glu Leu Gly Pro Asp Asp Val Pro Pro Phe Val Ala Ala
        180                 185                 190

Pro Glu Leu Thr Pro Ala Phe Cys Glu Leu Ser Ile Glu Gln Phe Ala
    195                 200                 205

Gly Leu Glu Asp Asp Asp Val Leu Val Asn Ser Phe Ser Asp Leu
210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
            245                 250                 255

Ser Asn Thr Ala Tyr Gly Phe Asn Leu Phe Arg Ser Thr Val Pro Cys
        260                 265                 270

Met Glu Trp Leu Asp Lys Gln Pro Pro Arg Ser Val Val Leu Val Ser
    275                 280                 285

Tyr Gly Thr Val Ser Thr Phe Asp Val Ala Lys Leu Glu Glu Leu Gly
290                 295                 300

Asn Gly Leu Cys Asn Ser Gly Lys Pro Phe Leu Trp Val Val Arg Ser
305                 310                 315                 320

Asn Glu Glu His Lys Leu Ser Val Gln Leu Arg Lys Lys Cys Glu Lys
            325                 330                 335

Arg Gly Leu Ile Val Pro Phe Cys Pro Gln Leu Glu Val Leu Ala His
        340                 345                 350

Lys Ala Thr Gly Cys Phe Leu Ser His Cys Gly Trp Asn Ser Thr Leu
    355                 360                 365

Glu Ala Ile Val Asn Gly Val Pro Leu Val Ala Met Pro His Trp Ala
370                 375                 380

Asp Gln Pro Thr Ile Ser Lys Tyr Val Glu Ser Leu Trp Gly Met Gly
385                 390                 395                 400
```

Val Arg Val Gln Leu Asp Lys Ser Gly Ile Leu Gln Arg Glu Glu Val
            405                 410                 415

Glu Arg Cys Ile Arg Glu Val Met Asp Gly Asp Arg Lys Glu Asp Tyr
        420                 425                 430

Arg Arg Asn Ala Thr Arg Leu Met Lys Lys Ala Lys Glu Ser Met Gln
            435                 440                 445

Glu Gly Gly Ser Ser Asp Lys Asn Ile Ala Glu Phe Ala Ala Lys Tyr
    450                 455                 460

Ser Asn
465

<210> SEQ ID NO 17
<211> LENGTH: 1401
<212> TYPE: DNA
<213> ORGANISM: Oryza sativa

<400> SEQUENCE: 17
atgggctcta tgtccactcc tgccgctagt gcgaacggtg gtcaggtcct tcttttacca       60
ttcccggctg ctcaaggtca caccaatcct atgttacagt tggaagaag attggcctat      120 cacgggttgc gtccgacttt agtgacaacc aggtatgttc tttccacaac cccacctcct      180
ggagatccct ttcgtgttgc tgctattagc gacggttttg atgatgcctc tggtatggct      240
gcgctaccag atcccggtga atacctgaga actcttgaag cacatggtgc taggacgtta      300
gcagaattgc ttctttcaga agcgagagct ggtagaccag ccagagtttt agtctacgat      360
ccacatctac catgggctag aagagtggca agagcggctg gagttgcaac agccgcattt      420
ctaagtcaac catgtgctgt ggacttgatc tatggcgagg tatgtgctag aagattagca      480
ctaccagtta ccccaacaga tgccagaggt ttatatgcaa gaggtgttct aggtgttgaa      540
ttggggccag atgatgttcc acccttcgta gcagcccctg aattaactcc tgccttctgt      600
gagcaatcta tcgagcagtt tgctggcttg gaggatgacg acgacgtact ggtcaattcc      660
ttctcggatt tggaaccaaa agaagctgct tacatggagt cgacgtggag agcaaagacg      720
ataggaccct cactaccatc cttttatctg gacgacggta gattgaggtc gaataccgct      780
tacggtttca atctgtttag gtcaactgtc ccgtgtatgg aatggttgga caaacaacct      840
ccccgttcag tggttttggt gtcatacgga acagtttcta cttttgatgt tgctaaactg      900
gaagaactgg gaaatggatt gtgcaattca ggtaaacctt ttctatgggt cgttagaagt      960
aacgaagagc ataagttgtc tgtccagttg agaaagaagt gtgagaaaag aggcttgata     1020
gttccgttct gcccacaatt ggaagtgttg gcccataaag caacaggttg cttcttatct     1080
cattgtggtt ggaacagcac attggaagcc atagtgaatg gagtccttt agtagctatg     1140 cctcactggt ctgatcaacc tactattagc aagtatgtcg aaagtttatg gggcatgggt     1200
gttcgtgtac aattagataa atctgggatc ttacaaagag aagaagtaga agatgcatt     1260 agggaagtaa tggatgggga tcgtaaagaa gattacagaa ggaacgccac taggttaatg     1320
aagaaagcga agaatcaat gcaagagggc ggctctagtg acaagaacat tgcagagttt     1380
gcagcaaagt attccaatta a                                               1401

<210> SEQ ID NO 18
<211> LENGTH: 466
<212> TYPE: PRT
<213> ORGANISM: Oryza sativa

<400> SEQUENCE: 18

```
Met Gly Ser Met Ser Thr Pro Ala Ala Ser Ala Asn Gly Gly Gln Val
1               5                   10                  15

Leu Leu Leu Pro Phe Pro Ala Ala Gln Gly His Thr Asn Pro Met Leu
            20                  25                  30

Gln Phe Gly Arg Arg Leu Ala Tyr His Gly Leu Arg Pro Thr Leu Val
        35                  40                  45

Thr Thr Arg Tyr Val Leu Ser Thr Thr Pro Pro Gly Asp Pro Phe
    50                  55                  60

Arg Val Ala Ala Ile Ser Asp Gly Phe Asp Asp Ala Ser Gly Met Ala
65                  70                  75                  80

Ala Leu Pro Asp Pro Gly Glu Tyr Leu Arg Thr Leu Glu Ala His Gly
                85                  90                  95

Ala Arg Thr Leu Ala Glu Leu Leu Ser Glu Ala Arg Ala Gly Arg
            100                 105                 110

Pro Ala Arg Val Leu Val Tyr Asp Pro His Leu Pro Trp Ala Arg Arg
        115                 120                 125

Val Ala Arg Ala Ala Gly Val Ala Thr Ala Ala Phe Leu Ser Gln Pro
    130                 135                 140

Cys Ala Val Asp Leu Ile Tyr Gly Glu Val Cys Ala Arg Arg Leu Ala
145                 150                 155                 160

Leu Pro Val Thr Pro Thr Asp Ala Arg Gly Leu Tyr Ala Arg Gly Val
                165                 170                 175

Leu Gly Val Glu Leu Gly Pro Asp Asp Val Pro Pro Phe Val Ala Ala
            180                 185                 190

Pro Glu Leu Thr Pro Ala Phe Cys Glu Gln Ser Ile Glu Gln Phe Ala
        195                 200                 205

Gly Leu Glu Asp Asp Asp Val Leu Val Asn Ser Phe Ser Asp Leu
    210                 215                 220

Glu Pro Lys Glu Ala Ala Tyr Met Glu Ser Thr Trp Arg Ala Lys Thr
225                 230                 235                 240

Ile Gly Pro Ser Leu Pro Ser Phe Tyr Leu Asp Asp Gly Arg Leu Arg
                245                 250                 255

Ser Asn Thr Ala Tyr Gly Phe Asn Leu Phe Arg Ser Thr Val Pro Cys
            260                 265                 270

Met Glu Trp Leu Asp Lys Gln Pro Pro Arg Ser Val Val Leu Val Ser
        275                 280                 285

Tyr Gly Thr Val Ser Thr Phe Asp Val Ala Lys Leu Glu Glu Leu Gly
    290                 295                 300

Asn Gly Leu Cys Asn Ser Gly Lys Pro Phe Leu Trp Val Arg Ser
305                 310                 315                 320

Asn Glu Glu His Lys Leu Ser Val Gln Leu Arg Lys Lys Cys Glu Lys
                325                 330                 335

Arg Gly Leu Ile Val Pro Phe Cys Pro Gln Leu Glu Val Leu Ala His
            340                 345                 350

Lys Ala Thr Gly Cys Phe Leu Ser His Cys Gly Trp Asn Ser Thr Leu
        355                 360                 365

Glu Ala Ile Val Asn Gly Val Pro Leu Val Ala Met Pro His Trp Ser
    370                 375                 380

Asp Gln Pro Thr Ile Ser Lys Tyr Val Glu Ser Leu Trp Gly Met Gly
385                 390                 395                 400

Val Arg Val Gln Leu Asp Lys Ser Gly Ile Leu Gln Arg Glu Glu Val
                405                 410                 415
```

Glu Arg Cys Ile Arg Glu Val Met Asp Gly Asp Lys Glu Asp Tyr
              420                 425                 430

Arg Arg Asn Ala Thr Arg Leu Met Lys Lys Ala Lys Glu Ser Met Gln
            435                 440                 445

Glu Gly Gly Ser Ser Asp Lys Asn Ile Ala Glu Phe Ala Ala Lys Tyr
        450                 455                 460

Ser Asn
465

<210> SEQ ID NO 19
<211> LENGTH: 1428
<212> TYPE: DNA
<213> ORGANISM: Hordeum vulgare

<400> SEQUENCE: 19

| | |
|---|---:|
| atggagacca cggtcaccgc ggtgtcaggc accacgagct cgagcgtcgg ccatggagcc | 60 |
| ggcggcggtg ctgcgagagt cctcctcctc ccgagcccgg agcgcaggg ccacaccaac | 120 |
| ccgatgctcc agttgggccg ccgcctggcg taccacggcc tccgcccac actcgtcgcc | 180 |
| acccgctacg tgctctccac caccccggcc cccgtgcgc ccttcgacgt ggccgcgatc | 240 |
| tccgacggct cgacgccgg tggcatggcc ttgtgccccg accggccgga gtacttctcc | 300 |
| cggctggagg ccgtgggctc cgagacgctg cgggagctcc tcctgtcgga ggcgcgcgcg | 360 |
| gggcggcccg tgcgcgtgct ggtgtacgac gctcacctgg cgtgggcacg gcgggtggca | 420 |
| caggcatccg gcgtcgcggc cgcggccttc ttctcccagc cgtgctcggt ggacgtcgtc | 480 |
| tacggggagc tgtgggcggg gcggctggcg ctgccggcca cggacgggcg cgcgctgctc | 540 |
| gcaagaggag tgctgggcgt ggagctgggg ctggaggaca tgccgccgtt cgcagcggtg | 600 |
| ccggagtcgc agccggcgtt cctccaggtg tcagttgggc agttcgaggg gctggactac | 660 |
| gccgacgacg tgctcgtcaa ctcattccgt gacatcgagc caaggaggt agagtacatg | 720 |
| gaattaacat ggagagcgaa gatggttgga ccaaccttgc catcatacta cctcggcgat | 780 |
| ggtcgcctac atctaataa atcatatggt ttcgacttgt tcaacagcga tgtggagtgt | 840 |
| atggattggc tagagaagca aatgaattca tctgttgtgc tcgtgtccta tgggactgtc | 900 |
| tccaattatg atgcaaccca gctagaggag cttggcaatg gtttgtgcaa ttctagcaaa | 960 |
| cctttctttt gggttgtaag atccaatgag gaacacaagt tatccgaaga actcaaagaa | 1020 |
| aaatgtggga aaattggatt aatagtctca tggtgcccccc agcttgaggt tcttgcacat | 1080 |
| agggctatag ttgcttcgt tacccactgt ggatggaact caacactaga ggcacttgtt | 1140 |
| aatggtgtcc ctttgtggg tattccacat tgggcagacc aacccaccat tgcaaagtat | 1200 |
| gtggagagtg catggggtat gggtgtgcgt gcacggaaaa acaagaatgg atgtctaaag | 1260 |
| aaggaggagg ttgagaggtg cattagagag gtgatggatg gggagagaaa ggatgagtac | 1320 |
| aaaaaaaatg ccatgaactg gatgcaaaag gccaaggagg caatgcaaga aggaggaagt | 1380 |
| tcagacaagc atgtagctga attcgctacc aagtattcgt caatataa | 1428 |

<210> SEQ ID NO 20
<211> LENGTH: 475
<212> TYPE: PRT
<213> ORGANISM: Hordeum vulgare

<400> SEQUENCE: 20

Met Glu Thr Thr Val Thr Ala Val Ser Gly Thr Thr Ser Ser Ser Val
1               5                   10                  15

```
Gly His Gly Ala Gly Gly Ala Ala Arg Val Leu Leu Pro Ser
        20              25              30

Pro Gly Ala Gln Gly His Thr Asn Pro Met Leu Gln Leu Gly Arg Arg
            35              40              45

Leu Ala Tyr His Gly Leu Arg Pro Thr Leu Val Ala Thr Arg Tyr Val
 50              55              60

Leu Ser Thr Thr Pro Ala Pro Gly Ala Pro Phe Asp Val Ala Ala Ile
65              70              75              80

Ser Asp Gly Phe Asp Ala Gly Gly Met Ala Leu Cys Pro Asp Pro Ala
                85              90              95

Glu Tyr Phe Ser Arg Leu Glu Ala Val Gly Ser Glu Thr Leu Arg Glu
                100             105             110

Leu Leu Leu Ser Glu Ala Arg Ala Gly Arg Pro Val Arg Val Leu Val
            115             120             125

Tyr Asp Ala His Leu Ala Trp Ala Arg Arg Val Ala Gln Ala Ser Gly
    130             135             140

Val Ala Ala Ala Phe Phe Ser Gln Pro Cys Ser Val Asp Val Val
145             150             155             160

Tyr Gly Glu Leu Trp Ala Gly Arg Leu Ala Leu Pro Ala Thr Asp Gly
                165             170             175

Arg Ala Leu Leu Ala Arg Gly Val Leu Gly Val Glu Leu Gly Leu Glu
                180             185             190

Asp Met Pro Pro Phe Ala Ala Val Pro Glu Ser Gln Pro Ala Phe Leu
            195             200             205

Gln Val Ser Val Gly Gln Phe Glu Gly Leu Asp Tyr Ala Asp Val
    210             215             220

Leu Val Asn Ser Phe Arg Asp Ile Glu Pro Lys Glu Val Glu Tyr Met
225             230             235             240

Glu Leu Thr Trp Arg Ala Lys Met Val Gly Pro Thr Leu Pro Ser Tyr
                245             250             255

Tyr Leu Gly Asp Gly Arg Leu Pro Ser Asn Lys Ser Tyr Gly Phe Asp
                260             265             270

Leu Phe Asn Ser Asp Val Glu Cys Met Asp Trp Leu Glu Lys Gln Met
            275             280             285

Asn Ser Ser Val Val Leu Val Ser Tyr Gly Thr Val Ser Asn Tyr Asp
    290             295             300

Ala Thr Gln Leu Glu Glu Leu Gly Asn Gly Leu Cys Asn Ser Ser Lys
305             310             315             320

Pro Phe Leu Trp Val Val Arg Ser Asn Glu Glu His Lys Leu Ser Glu
                325             330             335

Glu Leu Lys Glu Lys Cys Gly Lys Ile Gly Leu Ile Val Ser Trp Cys
                340             345             350

Pro Gln Leu Glu Val Leu Ala His Arg Ala Ile Gly Cys Phe Val Thr
            355             360             365

His Cys Gly Trp Asn Ser Thr Leu Glu Ala Leu Val Asn Gly Val Pro
    370             375             380

Phe Val Gly Ile Pro His Trp Ala Asp Gln Pro Thr Ile Ala Lys Tyr
385             390             395             400

Val Glu Ser Ala Trp Gly Met Gly Val Arg Ala Arg Lys Asn Lys Asn
                405             410             415

Gly Cys Leu Lys Lys Glu Glu Val Glu Arg Cys Ile Arg Glu Val Met
                420             425             430

Asp Gly Glu Arg Lys Asp Glu Tyr Lys Lys Asn Ala Met Asn Trp Met
```

435                 440                 445
Gln Lys Ala Lys Glu Ala Met Gln Glu Gly Gly Ser Ser Asp Lys His
    450                 455                 460

Val Ala Glu Phe Ala Thr Lys Tyr Ser Ser Ile
465                 470                 475

<210> SEQ ID NO 21
<211> LENGTH: 1428
<212> TYPE: DNA
<213> ORGANISM: Hordeum vulgare

<400> SEQUENCE: 21

| | |
|---|---|
| atggagacca cggtcaccgc ggtgtcaggc accacgagct cgagcgtcgg ccatggagcc | 60 |
| ggcggcggtg ctgcgagagt cctcctcctc ccgagcccgg gagcgcaggg ccacaccaac | 120 |
| ccgatgctcc agttgggccg ccgcctggcg taccacggcc tccgcccac actcgtcgcc | 180 |
| acccgctacg tgctctccac caccccggcc cccggtgcgc ccttcgacgt ggccgcgatc | 240 |
| tccgacggct cgacgccgg tggcatggcc ttgtgccccg accggcgga gtacttctcc | 300 |
| cggctggagg ccgtgggctc cgagacgctc cgggagctcc tcctgtcgga ggcgcgcgcg | 360 |
| gggcggcccg tgcgcgtgct ggtgtacgac gctgcgcgg cgtgggcacg gcgggtggca | 420 |
| caggcatccg gcgtcgcggc cgcggccttc ttctcccagc cgtgctcggt ggacgtcgtc | 480 |
| tacggggagc tgtgggcggg gcggctggcg ctgccggcca cggacgggcg cgcgctgctc | 540 |
| gcaagaggag tgctgggcgt ggagctgggg ctggaggaca tgccgccgtt cgcagcggtg | 600 |
| ccggagtcgc agccggcgtt cctccaggtg tcagttgggc agttcgaggg gctggactac | 660 |
| gccgacgacg tgctcgtcaa ctcattccgt gacatcgagc caaggaggt agagtacatg | 720 |
| gaattaacat ggagagcgaa gatggttgga ccaaccttgc catcatacta cctcggcgat | 780 |
| ggtcgcctac catctaataa atcatatggt ttcgacttgt tcaacagcga tgtggagtgt | 840 |
| atggattggc tagagaagca aatgaattca tctgttgtgc tcgtgtccta tgggactgtc | 900 |
| tccaattatg atgcaaccca gctagaggag cttggcaatg gtttgtgcaa ttctagcaaa | 960 |
| cctttctctt gggttgtaag atccaatgag gaacacaagt tatccgaaga actcaaagaa | 1020 |
| aaatgtggga aaattggatt aatagtctca tggtgccccc agcttgaggt tcttgcacat | 1080 |
| agggctatag gttgcttcgt tacccactgt ggatggaact caacactaga ggcacttgtt | 1140 |
| aatggtgtcc cttttgtggg tattccacat tgggcagacc aacccaccat tgcaaagtat | 1200 |
| gtggagagtg catggggtat gggtgtgcgt gcacggaaaa acaagaatgg atgtctaaag | 1260 |
| aaggaggagg ttgagaggtg cattagagag gtgatggatg gggagagaaa ggatgagtac | 1320 |
| aaaaaaaatg ccatgaactg gatgcaaaag gccaaggagg caatgcaaga aggaggaagt | 1380 |
| tcagacaagc atgtagctga attcgctacc aagtattcgt caatataa | 1428 |

<210> SEQ ID NO 22
<211> LENGTH: 475
<212> TYPE: PRT
<213> ORGANISM: Hordeum vulgare

<400> SEQUENCE: 22

Met Glu Thr Thr Val Thr Ala Val Ser Gly Thr Ser Ser Ser Val
1               5                   10                  15

Gly His Gly Ala Gly Gly Ala Ala Arg Val Leu Leu Leu Pro Ser
            20                  25                  30

Pro Gly Ala Gln Gly His Thr Asn Pro Met Leu Gln Leu Gly Arg Arg

```
            35                  40                  45
Leu Ala Tyr His Gly Leu Arg Pro Thr Leu Val Ala Thr Arg Tyr Val
 50                  55                  60
Leu Ser Thr Thr Pro Ala Pro Gly Ala Pro Phe Asp Val Ala Ala Ile
 65                  70                  75                  80
Ser Asp Gly Phe Asp Ala Gly Gly Met Ala Leu Cys Pro Asp Pro Ala
                 85                  90                  95
Glu Tyr Phe Ser Arg Leu Glu Ala Val Gly Ser Glu Thr Leu Arg Glu
                100                 105                 110
Leu Leu Leu Ser Glu Ala Arg Ala Gly Arg Pro Val Arg Val Leu Val
                115                 120                 125
Tyr Asp Ala Ala Ala Trp Ala Arg Arg Val Ala Gln Ala Ser Gly
     130                 135                 140
Val Ala Ala Ala Ala Phe Phe Ser Gln Pro Cys Ser Val Asp Val Val
145                 150                 155                 160
Tyr Gly Glu Leu Trp Ala Gly Arg Leu Ala Leu Pro Ala Thr Asp Gly
                165                 170                 175
Arg Ala Leu Leu Ala Arg Gly Val Leu Gly Val Glu Leu Gly Leu Glu
                180                 185                 190
Asp Met Pro Pro Phe Ala Ala Val Pro Glu Ser Gln Pro Ala Phe Leu
     195                 200                 205
Gln Val Ser Val Gly Gln Phe Glu Gly Leu Asp Tyr Ala Asp Asp Val
     210                 215                 220
Leu Val Asn Ser Phe Arg Asp Ile Glu Pro Lys Glu Val Glu Tyr Met
225                 230                 235                 240
Glu Leu Thr Trp Arg Ala Lys Met Val Gly Pro Thr Leu Pro Ser Tyr
                245                 250                 255
Tyr Leu Gly Asp Gly Arg Leu Pro Ser Asn Lys Ser Tyr Gly Phe Asp
                260                 265                 270
Leu Phe Asn Ser Asp Val Glu Cys Met Asp Trp Leu Glu Lys Gln Met
     275                 280                 285
Asn Ser Ser Val Val Leu Val Ser Tyr Gly Thr Val Ser Asn Tyr Asp
     290                 295                 300
Ala Thr Gln Leu Glu Glu Leu Gly Asn Gly Leu Cys Asn Ser Ser Lys
305                 310                 315                 320
Pro Phe Leu Trp Val Val Arg Ser Asn Glu Glu His Lys Leu Ser Glu
                325                 330                 335
Glu Leu Lys Glu Lys Cys Gly Lys Ile Gly Leu Ile Val Ser Trp Cys
                340                 345                 350
Pro Gln Leu Glu Val Leu Ala His Arg Ala Ile Gly Cys Phe Val Thr
     355                 360                 365
His Cys Gly Trp Asn Ser Thr Leu Glu Ala Leu Val Asn Gly Val Pro
     370                 375                 380
Phe Val Gly Ile Pro His Trp Ala Asp Gln Pro Thr Ile Ala Lys Tyr
385                 390                 395                 400
Val Glu Ser Ala Trp Gly Met Gly Val Arg Ala Arg Lys Asn Lys Asn
                405                 410                 415
Gly Cys Leu Lys Lys Glu Glu Val Glu Arg Cys Ile Arg Glu Val Met
                420                 425                 430
Asp Gly Glu Arg Lys Asp Glu Tyr Lys Lys Asn Ala Met Asn Trp Met
     435                 440                 445
Gln Lys Ala Lys Glu Ala Met Gln Glu Gly Gly Ser Ser Asp Lys His
     450                 455                 460
```

Val Ala Glu Phe Ala Thr Lys Tyr Ser Ser Ile
465                 470                 475

<210> SEQ ID NO 23
<211> LENGTH: 1491
<212> TYPE: DNA
<213> ORGANISM: Arabidopsis thaliana

<400> SEQUENCE: 23

| | | | | | |
|---|---|---|---|---|---|
| atggcttccg | aaaaatccca | caaagttcat | cctcctcttc | actttattct | tttcccttc | 60 |
| atggctcagg | gccacatgat | tcccatgatt | gatatagcaa | ggctcttggc | tcagcgcggt | 120 |
| gcgacagtaa | ctattgtcac | gacacgttat | aatgcaggga | ggttcgagaa | tgtcttaagt | 180 |
| cgtgccatgg | agtctggttt | acccatcaac | atagtgcatg | tgaattttcc | atatcaagaa | 240 |
| tttggtttgc | cagaaggaaa | agagaatata | gattcgtatg | actcaatgga | gctgatggta | 300 |
| cctttcttc | aagcagttaa | catgctcgaa | gatccggtca | tgaagctcat | ggaagagatg | 360 |
| aaacctagac | ctagctgtat | tatttctgat | ttgctcttgc | cttatacaag | caaaatcgca | 420 |
| aggaaattca | gtataccaaa | gatagttttc | cacggcacgg | gttgctttaa | tcttttgtgt | 480 |
| atgcatgttc | tacgcagaaa | cctcgagatc | ttgaagaact | aaagtcgga | taagattat | 540 |
| ttcctggttc | ctagttttcc | tgatagagtt | gaatttacaa | gcctcaagt | tccagtggaa | 600 |
| acaactgcaa | gtggagattg | aaagcgttc | ttggacgaaa | tggtagaagc | agaatacaca | 660 |
| tcctatggtg | tgatcgtcaa | cacatttcag | gagttggagc | ctgcttatgt | caaagactac | 720 |
| acgaaggcta | gggctggaaa | agtatggtcc | attggacctg | tttccttgtg | caacaaggca | 780 |
| ggtgctgata | agctgagag | ggaaaccag | ccgccattg | atcaagatga | gtgtcttcaa | 840 |
| tggcttgatt | ctaaagaaga | tggttcggtg | ttatatgttt | gccttggaag | tatctgtaat | 900 |
| ctacctttgt | ctcagctcaa | ggagctgggg | ctaggccttg | aaaaatccca | aagatctttt | 960 |
| atttgggtca | taagaggttg | gaaaaagtat | aatgaactat | atgagtggat | gatggagagc | 1020 |
| ggttttgaag | aaagaatcaa | agagagagga | cttcttatta | aagggtggtc | acctcaagtc | 1080 |
| cttatccttt | cacatccttc | cgttggagga | ttcctgacac | actgtggatg | gaactcgact | 1140 |
| ctcgaaggaa | tcacctcagg | cattccactg | atcacttggc | cgctgtttgg | agaccaattc | 1200 |
| tgcaaccaaa | aactggtcgt | tcaagtacta | aaagccggtg | taagtgccgg | ggttgaagaa | 1260 |
| gtcatgaaat | ggggagaaga | ggagaaaata | ggagtgttag | tggataaaga | aggagtaaag | 1320 |
| aaggcagtgg | aagagttaat | gggtgcgagt | gatgatgcaa | aagagaggag | aagaagagtc | 1380 |
| aaagagcttg | gagaatcagc | tcacaaggct | gtggaagaag | gaggctcttc | tcattctaac | 1440 |
| atcacatact | tgctacaaga | cataatgcaa | caagtgaaat | ccaagaactg | a | 1491 |

<210> SEQ ID NO 24
<211> LENGTH: 496
<212> TYPE: PRT
<213> ORGANISM: Arabidopsis thaliana

<400> SEQUENCE: 24

Met Ala Ser Glu Lys Ser His Lys Val His Pro Pro Leu His Phe Ile
1               5                   10                  15

Leu Phe Pro Phe Met Ala Gln Gly His Met Ile Pro Met Ile Asp Ile
                20                  25                  30

Ala Arg Leu Leu Ala Gln Arg Gly Ala Thr Val Thr Ile Val Thr Thr
            35                  40                  45

-continued

Arg Tyr Asn Ala Gly Arg Phe Glu Asn Val Leu Ser Arg Ala Met Glu
    50              55                  60

Ser Gly Leu Pro Ile Asn Ile Val His Val Asn Phe Pro Tyr Gln Glu
65              70                  75                  80

Phe Gly Leu Pro Glu Gly Lys Glu Asn Ile Asp Ser Tyr Asp Ser Met
                85                  90                  95

Glu Leu Met Val Pro Phe Phe Gln Ala Val Asn Met Leu Glu Asp Pro
            100                 105                 110

Val Met Lys Leu Met Glu Met Lys Pro Arg Pro Ser Cys Ile Ile
            115                 120                 125

Ser Asp Leu Leu Pro Tyr Thr Ser Lys Ile Ala Arg Lys Phe Ser
130                 135                 140

Ile Pro Lys Ile Val Phe His Gly Thr Gly Cys Phe Asn Leu Leu Cys
145                 150                 155                 160

Met His Val Leu Arg Arg Asn Leu Glu Ile Leu Lys Asn Leu Lys Ser
                165                 170                 175

Asp Lys Asp Tyr Phe Leu Val Pro Ser Phe Pro Asp Arg Val Glu Phe
            180                 185                 190

Thr Lys Pro Gln Val Pro Val Glu Thr Thr Ala Ser Gly Asp Trp Lys
            195                 200                 205

Ala Phe Leu Asp Glu Met Val Glu Ala Glu Tyr Thr Ser Tyr Gly Val
210                 215                 220

Ile Val Asn Thr Phe Gln Glu Leu Glu Pro Ala Tyr Val Lys Asp Tyr
225                 230                 235                 240

Thr Lys Ala Arg Ala Gly Lys Val Trp Ser Ile Gly Pro Val Ser Leu
            245                 250                 255

Cys Asn Lys Ala Gly Ala Asp Lys Ala Glu Arg Gly Asn Gln Ala Ala
            260                 265                 270

Ile Asp Gln Asp Glu Cys Leu Gln Trp Leu Asp Ser Lys Glu Asp Gly
            275                 280                 285

Ser Val Leu Tyr Val Cys Leu Gly Ser Ile Cys Asn Leu Pro Leu Ser
            290                 295                 300

Gln Leu Lys Glu Leu Gly Leu Gly Leu Glu Lys Ser Gln Arg Ser Phe
305                 310                 315                 320

Ile Trp Val Ile Arg Gly Trp Glu Lys Tyr Asn Glu Leu Tyr Glu Trp
                325                 330                 335

Met Met Glu Ser Gly Phe Glu Glu Arg Ile Lys Glu Arg Gly Leu Leu
            340                 345                 350

Ile Lys Gly Trp Ser Pro Gln Val Leu Ile Leu Ser His Pro Ser Val
            355                 360                 365

Gly Gly Phe Leu Thr His Cys Gly Trp Asn Ser Thr Leu Glu Gly Ile
            370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
            405                 410                 415

Gly Val Glu Glu Val Met Lys Trp Gly Glu Glu Lys Ile Gly Val
            420                 425                 430

Leu Val Asp Lys Glu Gly Val Lys Lys Ala Val Glu Leu Met Gly
            435                 440                 445

Ala Ser Asp Asp Ala Lys Glu Arg Arg Arg Val Lys Glu Leu Gly
450                 455                 460

Glu Ser Ala His Lys Ala Val Glu Glu Gly Gly Ser Ser His Ser Asn

Ile Thr Tyr Leu Leu Gln Asp Ile Met Gln Gln Val Lys Ser Lys Asn
465                 470                 475                 480
                485                 490                 495

<210> SEQ ID NO 25
<211> LENGTH: 1485
<212> TYPE: DNA
<213> ORGANISM: Arabidopsis thaliana

<400> SEQUENCE: 25

| | | | | | |
|---|---|---|---|---|---|
| atggtttccg | aaacaaccaa | atcttctcca | cttcactttg | ttctcttccc | tttcatggct | 60 |
| caaggccaca | tgattcccat | ggttgatatt | gcaaggctct | tggctcagcg | tggtgtgatc | 120 |
| ataacaattg | tcacgacgcc | tcacaatgca | gcgaggttca | gaatgtcct | aaaccgtgcc | 180 |
| attgagtctg | gcttgcccat | caacttagtg | caagtcaagt | ttccatatct | agaagctggt | 240 |
| ttgcaagaag | gacaagagaa | tatcgattct | cttgacacaa | tggagcggat | gataccttc | 300 |
| tttaaagcgg | ttaactttct | cgaagaacca | gtccagaagc | tcattgaaga | gatgaaccct | 360 |
| cgaccaagct | gtctaatttc | tgattttgt | ttgccttata | caagcaaaat | cgccaagaag | 420 |
| ttcaatatcc | caaagatcct | cttccatggc | atgggttgct | tttgtcttct | gtgtatgcat | 480 |
| gttttacgca | agaaccgtga | gatcttggac | aatttaaagt | cagataagga | gcttttcact | 540 |
| gttcctgatt | tcctgatag | agttgaattc | acaagaacgc | aagttccggt | agaaacatat | 600 |
| gttccagctg | gagactggaa | agatatcttt | gatggtatgg | tagaagcgaa | tgagacatct | 660 |
| tatggtgtga | tcgtcaactc | atttcaagag | ctcgagcctg | cttatgccaa | agactacaag | 720 |
| gaggtaaggt | ccggtaaagc | atggaccatt | ggacccgttt | ccttgtgcaa | caaggtagga | 780 |
| gccgacaaag | cagagagggg | aaacaaatca | gacattgatc | aagatgagtg | ccttaaatgg | 840 |
| ctcgattcta | gaaacatgg | ctcggtgctt | tacgtttgtc | ttggaagtat | ctgtaatctt | 900 |
| cctttgtctc | aactcaagga | gctgggacta | ggcctagagg | aatcccaaag | accttcatt | 960 |
| tgggtcataa | gaggttggga | gaagtacaaa | gagttagttg | agtggttctc | ggaaagcggc | 1020 |
| tttgaagata | gaatccaaga | tagaggactt | ctcatcaaag | gatggtcccc | tcaaatgctt | 1080 |
| atcctttcac | atccatcagt | tggagggttc | ctaacacact | gtggttggaa | ctcgactctt | 1140 |
| gaggggataa | ctgctggtct | accgctactt | acatggccgc | tattcgcaga | ccaattctgc | 1200 |
| aatgagaaat | tggtcgttga | ggtactaaaa | gccggtgtaa | gatccggggt | tgaacagcct | 1260 |
| atgaaatggg | gagaagagga | gaaaatagga | gtgttggtgg | ataaagaagg | agtgaagaag | 1320 |
| gcagtggaag | aattaatggg | tgagagtgat | gatgcaaaag | agaagaagaag | aagagccaaa | 1380 |
| gagcttggag | attcagctca | caaggctgtg | aagaaggag | gctcttctca | ttctaacatc | 1440 |
| tctttcttgc | tacaagacat | aatggaactg | cagaaccca | ataat | | 1485 |

<210> SEQ ID NO 26
<211> LENGTH: 495
<212> TYPE: PRT
<213> ORGANISM: Arabidopsis thaliana

<400> SEQUENCE: 26

Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

```
Asn Ala Ala Arg Phe Lys Asn Val Leu Asn Arg Ala Ile Glu Ser Gly
     50                  55                  60

Leu Pro Ile Asn Leu Val Gln Val Lys Phe Pro Tyr Leu Glu Ala Gly
 65                  70                  75                  80

Leu Gln Glu Gly Gln Glu Asn Ile Asp Ser Leu Asp Thr Met Glu Arg
                 85                  90                  95

Met Ile Pro Phe Phe Lys Ala Val Asn Phe Leu Glu Glu Pro Val Gln
                100                 105                 110

Lys Leu Ile Glu Glu Met Asn Pro Arg Pro Ser Cys Leu Ile Ser Asp
            115                 120                 125

Phe Cys Leu Pro Tyr Thr Ser Lys Ile Ala Lys Phe Asn Ile Pro
130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
                180                 185                 190

Thr Gln Val Pro Val Glu Thr Tyr Val Pro Ala Gly Asp Trp Lys Asp
            195                 200                 205

Ile Phe Asp Gly Met Val Glu Ala Asn Glu Thr Ser Tyr Gly Val Ile
            210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
                260                 265                 270

Asp Gln Asp Glu Cys Leu Lys Trp Leu Asp Ser Lys Lys His Gly Ser
            275                 280                 285

Val Leu Tyr Val Cys Leu Gly Ser Ile Cys Asn Leu Pro Leu Ser Gln
            290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
                340                 345                 350

Lys Gly Trp Ser Pro Gln Met Leu Ile Leu Ser His Pro Ser Val Gly
            355                 360                 365

Gly Phe Leu Thr His Cys Gly Trp Asn Ser Thr Leu Glu Gly Ile Thr
            370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Lys Ile Gly Val Leu
                420                 425                 430

Val Asp Lys Glu Gly Val Lys Lys Ala Val Glu Leu Met Gly Glu
            435                 440                 445

Ser Asp Asp Ala Lys Glu Arg Arg Arg Ala Lys Glu Leu Gly Asp
    450                 455                 460
```

Ser Ala His Lys Ala Val Glu Glu Gly Gly Ser His Ser Asn Ile
465                 470                 475                 480

Ser Phe Leu Leu Gln Asp Ile Met Glu Leu Ala Glu Pro Asn Asn
                485                 490                 495

<210> SEQ ID NO 27
<211> LENGTH: 1488
<212> TYPE: DNA
<213> ORGANISM: Arabidopsis thaliana

<400> SEQUENCE: 27

| | | | | | |
|---|---|---|---|---|---|
| atggctttcg | aaaaaaacaa | cgaaccttt | cctcttcact | ttgttctctt | cccttcatg | 60 |
| gctcaaggcc | acatgattcc | catggttgat | attgcaaggc | tcttggctca | gcgaggtgtg | 120 |
| cttataacaa | ttgtcacgac | gcctcacaat | gcagcaaggt | tcaagaatgt | cctaaaccgt | 180 |
| gccattgagt | ctggtttgcc | catcaaccta | gtgcaagtca | agtttccata | tcaagaagct | 240 |
| ggtctgcaag | aaggacaaga | aaatatggat | ttgcttacca | cgatggagca | gataacatct | 300 |
| ttctttaaag | cggttaactt | actcaaagaa | ccagtccaga | accttattga | agagatgagc | 360 |
| ccgcgaccaa | gctgtctaat | ctctgatatg | tgtttgtcgt | atacaagcga | aatcgccaag | 420 |
| aagttcaaaa | taccaaagat | cctcttccat | ggcatgggtt | gcttttgtct | tctgtgtgtt | 480 |
| aacgttctgc | gcaagaaccg | tgagatcttg | gacaatttaa | agtctgataa | ggagtacttc | 540 |
| attgttcctt | attttcctga | tagagttgaa | ttcacaagac | ctcaagttcc | ggtggaaaca | 600 |
| tatgttcctg | caggctggaa | agagatcttg | gaggatatgg | tagaagcgga | taagacatct | 660 |
| tatggtgtta | tagtcaactc | atttcaagag | ctcgaacctg | cgtatgccaa | agacttcaag | 720 |
| gaggcaaggt | ctggtaaagc | atggaccatt | ggacctgttt | ccttgtgcaa | caaggtagga | 780 |
| gtagacaaag | cagagagggg | aaacaaatca | gatattgatc | aagatgagtg | ccttgaatgg | 840 |
| ctcgattcta | aggaaccggg | atctgtgctc | tacgtttgcc | ttggaagtat | ttgtaatctt | 900 |
| cctctgtctc | agctccttga | gctgggacta | ggcctagagg | aatcccaaag | accttcatc | 960 |
| tgggtcataa | gaggttggga | gaaatacaaa | gagttagttg | agtggttctc | ggaaagcggc | 1020 |
| tttgaagata | gaatccaaga | tagaggactt | ctcatcaaag | gatggtcccc | tcaaatgctt | 1080 |
| atccttcac | atccttctgt | tggagggttc | ttaacgcact | gcggatggaa | ctcgactctt | 1140 |
| gaggggataa | ctgctggtct | accaatgctt | acatggccac | tatttgcaga | ccaattctgc | 1200 |
| aacgagaaac | tggtcgtaca | aatactaaaa | gtcggtgtaa | gtgccgaggt | taaagaggtc | 1260 |
| atgaaatggg | gagaagaaga | gaagatagga | gtgttggtgg | ataaagaagg | agtgaagaag | 1320 |
| gcagtggaag | aactaatggg | tgagagtgat | gatgcaaaag | agaagaagaag | aagagccaaa | 1380 |
| gagcttggag | aatcagctca | caaggctgtg | gaagaaggag | ctcctctca | ttctaatatc | 1440 |
| actttcttgc | tacaagacat | aatgcaacta | gcacagtcca | ataattga | | 1488 |

<210> SEQ ID NO 28
<211> LENGTH: 495
<212> TYPE: PRT
<213> ORGANISM: Arabidopsis thaliana

<400> SEQUENCE: 28

Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
                20                  25                  30

Arg Leu Leu Ala Gln Arg Gly Val Leu Ile Thr Ile Val Thr Thr Pro

```
                35                  40                  45
His Asn Ala Ala Arg Phe Lys Asn Val Leu Asn Arg Ala Ile Glu Ser
 50                  55                  60

Gly Leu Pro Ile Asn Leu Val Gln Val Lys Phe Pro Tyr Gln Glu Ala
 65                  70                  75                  80

Gly Leu Gln Glu Gly Gln Glu Asn Met Asp Leu Leu Thr Thr Met Glu
                     85                  90                  95

Gln Ile Thr Ser Phe Phe Lys Ala Val Asn Leu Leu Lys Glu Pro Val
                100                 105                 110

Gln Asn Leu Ile Glu Glu Met Ser Pro Arg Pro Ser Cys Leu Ile Ser
                115                 120                 125

Asp Met Cys Leu Ser Tyr Thr Ser Glu Ile Ala Lys Lys Phe Lys Ile
                130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
                180                 185                 190

Arg Pro Gln Val Pro Val Glu Thr Tyr Val Pro Ala Gly Trp Lys Glu
                195                 200                 205

Ile Leu Glu Asp Met Val Glu Ala Asp Lys Thr Ser Tyr Gly Val Ile
210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
                260                 265                 270

Asp Gln Asp Glu Cys Leu Glu Trp Leu Asp Ser Lys Glu Pro Gly Ser
                275                 280                 285

Val Leu Tyr Val Cys Leu Gly Ser Ile Cys Asn Leu Pro Leu Ser Gln
                290                 295                 300

Leu Leu Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
                340                 345                 350

Lys Gly Trp Ser Pro Gln Met Leu Ile Leu Ser His Pro Ser Val Gly
                355                 360                 365

Gly Phe Leu Thr His Cys Gly Trp Asn Ser Thr Leu Glu Gly Ile Thr
                370                 375                 380

Ala Gly Leu Pro Met Leu Thr Trp Pro Leu Phe Ala Asp Gln Phe Cys
385                 390                 395                 400

Asn Glu Lys Leu Val Val Gln Ile Leu Lys Val Gly Val Ser Ala Glu
                405                 410                 415

Val Lys Glu Val Met Lys Trp Gly Glu Glu Lys Ile Gly Val Leu
                420                 425                 430

Val Asp Lys Glu Gly Val Lys Lys Ala Val Glu Glu Leu Met Gly Glu
                435                 440                 445

Ser Asp Asp Ala Lys Glu Arg Arg Arg Ala Lys Glu Leu Gly Glu
                450                 455                 460
```

Ser Ala His Lys Ala Val Glu Glu Gly Gly Ser Ser His Ser Asn Ile
465                 470                 475                 480

Thr Phe Leu Leu Gln Asp Ile Met Gln Leu Ala Gln Ser Asn Asn
                485                 490                 495

<210> SEQ ID NO 29
<211> LENGTH: 1407
<212> TYPE: DNA
<213> ORGANISM: Brachypodium distachyon

<400> SEQUENCE: 29

| | | | | |
|---|---|---|---|---|
| atggagacga | attccccgtc | ctccgccgaa | gaaggaagcg | gcaccggcgg cggcgcccat | 60 |
| gttctcctcc | tcgccttccc | ggggcgcag | ggccacctca | acccgctgct gcagttcggc | 120 |
| cgccgcctcg | cctaccacgg | cctccgccca | accttcgtca | ccacccgcta cctcctctcc | 180 |
| accgtcccgc | ccccgcgggg | gcccttccgc | gtcgccgcca | tctccgacgg cttcgacgcc | 240 |
| ggcggcatgg | ccgcgtgcag | cacggggttc | ggggactacg | ccgccgcct ggccgcggcg | 300 |
| ggctccgaaa | ccctggaggc | cctcttccgg | tccgaggccg | aggcggggcg gtccgtgcgc | 360 |
| gcgctcgtgt | acgaccccca | ccttccgtgg | cggcgcgcg | tggcgcgcgc cgccggcgtg | 420 |
| cggaccgcgg | ccttcttctc | gcagccgtgc | gccgtggacc | tcatctacgg ggaggtctgg | 480 |
| tcgggccgcg | tcggcctgcc | gatcaaggac | gggagcgctt | gcgggggtt gctgagctta | 540 |
| gagctcgagc | cggaggacgt | gccgtcgttt | gtggcggcgc | cggactcgta ccggctgttc | 600 |
| ctcgacgctg | tggtggggca | gttcgaaggg | ctggaggacg | ccgacgacgt gtttgtcaac | 660 |
| tcattccacg | acctggagcc | caaggaggca | gattacttgt | catccacatg gcgtgtcaag | 720 |
| accattggcc | cgactctgcc | atcgttctac | ctggacgatg | ataggttgcc atccaacaag | 780 |
| acatatgggt | ttgatctctt | tgacagcaca | gcaccctgca | tggcatggct ggatagccac | 840 |
| cccccttgct | cagttgtcta | cgcctcgtat | ggaactgtcg | ctgacctgga ccaagcccag | 900 |
| ttagaggaga | taggcaatgg | attgtgcaat | tctggtaagc | ggttcctttg ggttgtcagg | 960 |
| tccgttgatg | aacataagtt | atcagaagag | ctccgtggca | aatgcaacga gatgggcctg | 1020 |
| atagtttcat | ggtgccccca | gcttgaggtt | ttatctcaca | aagccacagg ttgtttctta | 1080 |
| actcactgtg | gatggaactc | aacaacagaa | gcaattgtta | ctggcgttcc actgttggct | 1140 |
| atgcctcagt | ggacagatca | accaactaca | gcaaaatacg | ttgaaagtgc atggggaatc | 1200 |
| ggtgtgcgag | tccaccgtga | taatgaagga | gtggttagaa | aggaagaggt agagaggtgc | 1260 |
| ataagagaag | tattagatgg | ggaaaggaag | gaggagtaca | ggaagaatgc tgctaggtgg | 1320 |
| atgaagaagg | ctaaagaggc | aatgcaggaa | ggagggagct | cagacaagaa tattgctgag | 1380 |
| tttgcggcca | agtatgcttc | aagttga | | | 1407 |

<210> SEQ ID NO 30
<211> LENGTH: 468
<212> TYPE: PRT
<213> ORGANISM: Brachypodium distachyon

<400> SEQUENCE: 30

Met Glu Thr Asn Ser Pro Ser Ser Ala Glu Glu Gly Ser Gly Thr Gly
1               5                   10                  15

Gly Gly Ala His Val Leu Leu Leu Ala Phe Pro Gly Ala Gln Gly His
                20                  25                  30

Leu Asn Pro Leu Leu Gln Phe Gly Arg Arg Leu Ala Tyr His Gly Leu
            35                  40                  45

```
Arg Pro Thr Phe Val Thr Thr Arg Tyr Leu Leu Ser Thr Val Pro Pro
        50                  55                  60

Pro Ala Gly Pro Phe Arg Val Ala Ala Ile Ser Asp Gly Phe Asp Ala
65                      70                  75                  80

Gly Gly Met Ala Ala Cys Ser Thr Gly Phe Gly Asp Tyr Gly Arg Arg
                85                  90                  95

Leu Ala Ala Ala Gly Ser Glu Thr Leu Glu Ala Leu Phe Arg Ser Glu
            100                 105                 110

Ala Glu Ala Gly Arg Ser Val Arg Ala Leu Val Tyr Asp Pro His Leu
            115                 120                 125

Pro Trp Ala Ala Arg Val Ala Arg Ala Gly Val Arg Thr Ala Ala
        130                 135                 140

Phe Phe Ser Gln Pro Cys Ala Val Asp Leu Ile Tyr Gly Glu Val Trp
145                 150                 155                 160

Ser Gly Arg Val Gly Leu Pro Ile Lys Asp Gly Ser Ala Leu Arg Gly
                165                 170                 175

Leu Leu Ser Leu Glu Leu Glu Pro Glu Asp Val Pro Ser Phe Val Ala
            180                 185                 190

Ala Pro Asp Ser Tyr Arg Leu Phe Leu Asp Ala Val Val Gly Gln Phe
            195                 200                 205

Glu Gly Leu Glu Asp Ala Asp Asp Val Phe Val Asn Ser Phe His Asp
210                 215                 220

Leu Glu Pro Lys Glu Ala Asp Tyr Leu Ser Ser Thr Trp Arg Val Lys
225                 230                 235                 240

Thr Ile Gly Pro Thr Leu Pro Ser Phe Tyr Leu Asp Asp Asp Arg Leu
                245                 250                 255

Pro Ser Asn Lys Thr Tyr Gly Phe Asp Leu Phe Asp Ser Thr Ala Pro
            260                 265                 270

Cys Met Ala Trp Leu Asp Ser His Pro Pro Cys Ser Val Val Tyr Ala
            275                 280                 285

Ser Tyr Gly Thr Val Ala Asp Leu Asp Gln Ala Gln Leu Glu Glu Ile
        290                 295                 300

Gly Asn Gly Leu Cys Asn Ser Gly Lys Arg Phe Leu Trp Val Val Arg
305                 310                 315                 320

Ser Val Asp Glu His Lys Leu Ser Glu Glu Leu Arg Gly Lys Cys Asn
                325                 330                 335

Glu Met Gly Leu Ile Val Ser Trp Cys Pro Gln Leu Glu Val Leu Ser
            340                 345                 350

His Lys Ala Thr Gly Cys Phe Leu Thr His Cys Gly Trp Asn Ser Thr
        355                 360                 365

Thr Glu Ala Ile Val Thr Gly Val Pro Leu Leu Ala Met Pro Gln Trp
370                 375                 380

Thr Asp Gln Pro Thr Thr Ala Lys Tyr Val Glu Ser Ala Trp Gly Ile
385                 390                 395                 400

Gly Val Arg Val His Arg Asp Asn Glu Gly Val Val Arg Lys Glu Glu
                405                 410                 415

Val Glu Arg Cys Ile Arg Glu Val Leu Asp Gly Glu Arg Lys Glu Glu
            420                 425                 430

Tyr Arg Lys Asn Ala Ala Arg Trp Met Lys Ala Lys Glu Ala Met
        435                 440                 445

Gln Glu Gly Gly Ser Ser Asp Lys Asn Ile Ala Glu Phe Ala Ala Lys
    450                 455                 460
```

Tyr Ala Ser Ser
465

<210> SEQ ID NO 31
<211> LENGTH: 1416
<212> TYPE: DNA
<213> ORGANISM: Sorghum bicolor

<400> SEQUENCE: 31

| | | | | | |
|---|---|---|---|---|---|
| atggggagca | cgagcaccac | caccacctca | tcttcctcct | ctgctacccg | cggcggcggc | 60 |
| gcacacgtgc | tgctcctgcc | gtacccaggc | gcgcagggcc | acacgaaccc | gctgctcgag | 120 |
| ttcggccgcc | gcctcgccta | ccacggcttc | caccccacgc | tcgtcacttc | ccggtacgtg | 180 |
| ctctccacca | ccccgccacc | aggtgagccc | ttcagggtgg | ccgccatctc | cgacggcttc | 240 |
| gacgacggcg | gcgcggccgc | cgtgctccgac | gttgaagtgt | actggcgcca | gctcgaggcc | 300 |
| gtcggctcgg | agacgctggc | ggagctgatc | cgctccgagg | ctgccgaggg | tcgccccgtg | 360 |
| cgcgtgctgg | tctacgaccc | gcacctgccg | tgggcgcggc | gcgtggcgaa | ggcggctggg | 420 |
| gtgccgaccg | cggcgttcct | gtcgcagcct | tgcgccgtcg | acgtcgtcta | cggggaggtg | 480 |
| tgggcgggc | ggctgccact | gccggtggtg | gacgggaaag | agctgtttgc | gcgcgggttg | 540 |
| ctgggtgtgg | agctcgggcc | cgacgaggtg | ccgccgttcg | cggcgaagcc | ggactggtgc | 600 |
| cctgtgttcc | ttgaggcgtg | cacgcggcag | ttcgaggggc | tggaggacgc | cgacgacgtg | 660 |
| ctcgtcaact | cattccacga | gatcgaaccc | aaggaggcag | attatatggc | actaacgtgg | 720 |
| cgtgcaaaga | caataggccc | aaccttgcca | tcattttatc | ttgatgatga | ccgcttgccg | 780 |
| ttgaacaaga | gttacggttt | caacctcttc | aacagcagcg | agtcttgtct | ggattggctt | 840 |
| gacaagcagc | ttccatgttc | tgtagttctt | gtatcctatg | gtactgtctc | tgattatgat | 900 |
| gaagcacagt | tagaagagct | gggcaatgga | ttgtacaatt | ctggcaaacc | attcatttgg | 960 |
| gttgtgaggt | caaacgaaga | acacaaattg | tccaatgaac | ttcgtgccaa | gtgcaaggaa | 1020 |
| cgtggcctta | tcgtttcttg | gtgctcccag | ctcgaagttc | tagcacataa | agccacaggt | 1080 |
| tgtttcttca | cacattgcgg | atggaactcg | acgctggaag | cagtagttaa | tggtgtgcca | 1140 |
| atggtggcaa | taccacactg | gcagaccag | ccgaccatat | caaaatatat | ggagagcata | 1200 |
| tggggattgg | gtgtccgggt | gcgcaaggat | gagaaaggct | tggtgacgag | agacgaggtg | 1260 |
| gaaaggtgca | tcaaggatgt | tatggatggg | gatagaaagg | ataattatag | gatgaacgcc | 1320 |
| actatgtgga | tgcaaaaggc | caaggaagcc | atgcagaatg | gagggagctc | ggacaagaat | 1380 |
| gtttgtgaat | tcgtggcgaa | gtattcatca | aattag | | | 1416 |

<210> SEQ ID NO 32
<211> LENGTH: 471
<212> TYPE: PRT
<213> ORGANISM: Sorghum bicolor

<400> SEQUENCE: 32

Met Gly Ser Thr Ser Thr Thr Thr Thr Ser Ser Ser Ser Ala Thr
1               5                   10                  15

Arg Gly Gly Gly Ala His Val Leu Leu Leu Pro Tyr Pro Gly Ala Gln
                20                  25                  30

Gly His Thr Asn Pro Leu Leu Glu Phe Gly Arg Arg Leu Ala Tyr His
            35                  40                  45

Gly Phe His Pro Thr Leu Val Thr Ser Arg Tyr Val Leu Ser Thr Thr
        50                  55                  60

```
Pro Pro Pro Gly Glu Pro Phe Arg Val Ala Ala Ile Ser Asp Gly Phe
 65                  70                  75                  80

Asp Asp Gly Gly Ala Ala Ala Cys Ser Asp Val Glu Val Tyr Trp Arg
                 85                  90                  95

Gln Leu Glu Ala Val Gly Ser Glu Thr Leu Ala Glu Leu Ile Arg Ser
            100                 105                 110

Glu Ala Ala Glu Gly Arg Pro Val Arg Val Leu Val Tyr Asp Pro His
            115                 120                 125

Leu Pro Trp Ala Arg Arg Val Ala Lys Ala Ala Gly Val Pro Thr Ala
        130                 135                 140

Ala Phe Leu Ser Gln Pro Cys Ala Val Asp Val Val Tyr Gly Glu Val
145                 150                 155                 160

Trp Ala Gly Arg Leu Pro Leu Pro Val Asp Gly Lys Glu Leu Phe
            165                 170                 175

Ala Arg Gly Leu Leu Gly Val Glu Leu Gly Pro Asp Glu Val Pro Pro
            180                 185                 190

Phe Ala Ala Lys Pro Asp Trp Cys Pro Val Phe Leu Glu Ala Cys Thr
            195                 200                 205

Arg Gln Phe Glu Gly Leu Glu Asp Ala Asp Val Leu Val Asn Ser
210                 215                 220

Phe His Glu Ile Glu Pro Lys Glu Ala Asp Tyr Met Ala Leu Thr Trp
225                 230                 235                 240

Arg Ala Lys Thr Ile Gly Pro Thr Leu Pro Ser Phe Tyr Leu Asp Asp
            245                 250                 255

Asp Arg Leu Pro Leu Asn Lys Ser Tyr Gly Phe Asn Leu Phe Asn Ser
        260                 265                 270

Ser Glu Ser Cys Leu Asp Trp Leu Asp Lys Gln Leu Pro Cys Ser Val
        275                 280                 285

Val Leu Val Ser Tyr Gly Thr Val Ser Asp Tyr Asp Glu Ala Gln Leu
        290                 295                 300

Glu Glu Leu Gly Asn Gly Leu Tyr Asn Ser Gly Lys Pro Phe Ile Trp
305                 310                 315                 320

Val Val Arg Ser Asn Glu Glu His Lys Leu Ser Asn Glu Leu Arg Ala
            325                 330                 335

Lys Cys Lys Glu Arg Gly Leu Ile Val Ser Trp Cys Ser Gln Leu Glu
            340                 345                 350

Val Leu Ala His Lys Ala Thr Gly Cys Phe Phe Thr His Cys Gly Trp
            355                 360                 365

Asn Ser Thr Leu Glu Ala Val Asn Gly Val Pro Met Val Ala Ile
        370                 375                 380

Pro His Trp Ala Asp Gln Pro Thr Ile Ser Lys Tyr Met Glu Ser Ile
385                 390                 395                 400

Trp Gly Leu Gly Val Arg Val Arg Lys Asp Glu Lys Gly Leu Val Thr
                405                 410                 415

Arg Asp Glu Val Glu Arg Cys Ile Lys Asp Val Met Asp Gly Asp Arg
            420                 425                 430

Lys Asp Asn Tyr Arg Met Asn Ala Thr Met Trp Met Gln Lys Ala Lys
        435                 440                 445

Glu Ala Met Gln Asn Gly Gly Ser Ser Asp Lys Asn Val Cys Glu Phe
        450                 455                 460

Val Ala Lys Tyr Ser Ser Asn
465                 470
```

```
<210> SEQ ID NO 33
<211> LENGTH: 1410
<212> TYPE: DNA
<213> ORGANISM: Brachypodium distachyon

<400> SEQUENCE: 33
atggacagca caggcaaatc ggtgatggcg accagcgagg ggccgagcat cctcttcctc      60
ccgttcccgg gggcgcaggg ccacgcgaac ccgatgctcc agttcggcca ccgcctggct     120
taccagtacg gcttccgccc cacgctcgtc gtcacccgct acgtgctctc cacggccctg     180
cccccgacg cgcccttccg cgtggccgcc atctccgacg gcttcgacgc cggcggcatt     240
cggtcgtgcc tcgacatggc ggagtactgg cgccggctgg aggcggtcgg gtcggagact     300
tgtcgcggc tcatctccga cgaggcgcgc gaggggcggc ccgtcagggt gctcgtgtac     360
gacccgcacg tggcgtgggc gcggcgggtg gcacggggag ccggcgtgcc cgcggcggcc     420
ttcttttcgc agccgtgcgc ggtggacatc ttctacgggg agctgcacgc ggggcggatg     480
gcgatgcccg tcacggaggc ggacgcgcga gcgctgctgg tgcgcggagc gatagggtg     540
gagcttgcgc tggatgatgt gccgcccttc gtggtcgtgc cggagtcgca gccggtgttc     600
accaaggcgt cgattgggca gttcgaaggg ctggaggatg ccgacgacgt gctcgtcaat     660
tccttccgcg acatcgagcc aatggaggta gaatatatgg agtcaacgtg gcgagccaag     720
acgataggcc aaccttgcc gtcattctac cttgatgacg accgtctgcc atccaacaag     780
tcttatggtt tcaatctctt caacggtggt gatgcagttt gcatgaaatg gttggatcaa     840
cagagcatgt catctgttgt gcttgtgtcc tatgggactg tctccaacta cgacgaatcc     900
cagctagagg agctaggaaa tggactatgc agttctggca agccttttat ttgggttgtg     960
agatccaacg aggcacacaa attgtcaggc gaactcaagg cgaaatgcga agaagggga    1020
ctaattgttt cttggtgccc ccaactcgag gttctggcac acaaggccac gggttgtttc    1080
ttaacacatt gtggatggaa ctccacatta gaggcgatcg ttaacggtgt acctgtagtg    1140
ggaattccac attgggcaga ccagccaacc atcgcgaagt atgtggagag cgcatgggac    1200
atgggcgtgc gagtgaagaa aagcttgaat ggacaactaa ggaggagga gatcgagaga    1260
tgcatcaagg aggtgatgga tagtgagagg aaggatgagt atacaaggaa tgccgcgaag    1320
tggatgcaaa aggccaagga gacaatgcac gcgggaggaa gctcaaacaa acatattgct    1380
gaattcgctg ctaagtattc gtcaagttaa                                     1410

<210> SEQ ID NO 34
<211> LENGTH: 469
<212> TYPE: PRT
<213> ORGANISM: Brachypodium distachyon

<400> SEQUENCE: 34

Met Asp Ser Thr Gly Lys Ser Val Met Ala Thr Ser Glu Gly Pro Ser
 1               5                  10                  15

Ile Leu Phe Leu Pro Phe Pro Gly Ala Gln Gly His Ala Asn Pro Met
                20                  25                  30

Leu Gln Phe Gly His Arg Leu Ala Tyr Gln Tyr Gly Phe Arg Pro Thr
             35                  40                  45

Leu Val Val Thr Arg Tyr Val Leu Ser Thr Ala Leu Pro Pro Asp Ala
         50                  55                  60

Pro Phe Arg Val Ala Ala Ile Ser Asp Gly Phe Asp Ala Gly Gly Ile
 65                  70                  75                  80

Arg Ser Cys Leu Asp Met Ala Glu Tyr Trp Arg Arg Leu Glu Ala Val
```

```
                    85                  90                  95
Gly Ser Glu Thr Leu Ser Arg Leu Ile Ser Asp Glu Ala Arg Glu Gly
                100                 105                 110

Arg Pro Val Arg Val Leu Val Tyr Asp Pro His Val Ala Trp Ala Arg
            115                 120                 125

Arg Val Ala Arg Glu Ala Gly Val Pro Ala Ala Phe Phe Ser Gln
130                 135                 140

Pro Cys Ala Val Asp Ile Phe Tyr Gly Glu Leu His Ala Gly Arg Met
145                 150                 155                 160

Ala Met Pro Val Thr Glu Ala Asp Ala Arg Ala Leu Leu Val Arg Gly
                165                 170                 175

Ala Ile Gly Val Glu Leu Ala Leu Asp Asp Val Pro Pro Phe Val Val
                180                 185                 190

Val Pro Glu Ser Gln Pro Val Phe Thr Lys Ala Ser Ile Gly Gln Phe
            195                 200                 205

Glu Gly Leu Glu Asp Ala Asp Asp Val Leu Val Asn Ser Phe Arg Asp
            210                 215                 220

Ile Glu Pro Met Glu Val Glu Tyr Met Glu Ser Thr Trp Arg Ala Lys
225                 230                 235                 240

Thr Ile Gly Pro Thr Leu Pro Ser Phe Tyr Leu Asp Asp Arg Leu
                245                 250                 255

Pro Ser Asn Lys Ser Tyr Gly Phe Asn Leu Phe Asn Gly Gly Asp Ala
            260                 265                 270

Val Cys Met Lys Trp Leu Asp Gln Gln Ser Met Ser Ser Val Val Leu
            275                 280                 285

Val Ser Tyr Gly Thr Val Ser Asn Tyr Asp Glu Ser Gln Leu Glu Glu
            290                 295                 300

Leu Gly Asn Gly Leu Cys Ser Ser Gly Lys Pro Phe Ile Trp Val Val
305                 310                 315                 320

Arg Ser Asn Glu Ala His Lys Leu Ser Gly Glu Leu Lys Ala Lys Cys
                325                 330                 335

Glu Lys Lys Gly Leu Ile Val Ser Trp Cys Pro Gln Leu Glu Val Leu
                340                 345                 350

Ala His Lys Ala Thr Gly Cys Phe Leu Thr His Cys Gly Trp Asn Ser
                355                 360                 365

Thr Leu Glu Ala Ile Val Asn Gly Val Pro Val Gly Ile Pro His
            370                 375                 380

Trp Ala Asp Gln Pro Thr Ile Ala Lys Tyr Val Glu Ser Ala Trp Asp
385                 390                 395                 400

Met Gly Val Arg Val Lys Lys Ser Leu Asn Gly Gln Leu Arg Arg Glu
                405                 410                 415

Glu Ile Glu Arg Cys Ile Lys Glu Val Met Asp Ser Glu Arg Lys Asp
                420                 425                 430

Glu Tyr Thr Arg Asn Ala Ala Lys Trp Met Gln Lys Ala Lys Glu Thr
                435                 440                 445

Met His Ala Gly Gly Ser Ser Asn Lys His Ile Ala Glu Phe Ala Ala
                450                 455                 460

Lys Tyr Ser Ser Ser
465

<210> SEQ ID NO 35
<211> LENGTH: 23
<212> TYPE: DNA
<213> ORGANISM: Artificial sequence
```

```
<220> FEATURE:
<223> OTHER INFORMATION: Primer

<400> SEQUENCE: 35
atgggctcta tgtccactcc tgc                                              23

<210> SEQ ID NO 36
<211> LENGTH: 24
<212> TYPE: DNA
<213> ORGANISM: Artificial sequence
<220> FEATURE:
<223> OTHER INFORMATION: Primer

<400> SEQUENCE: 36
attggaatac tttgctgcaa actc                                             24

<210> SEQ ID NO 37
<211> LENGTH: 37
<212> TYPE: DNA
<213> ORGANISM: Artificial sequence
<220> FEATURE:
<223> OTHER INFORMATION: Primer

<400> SEQUENCE: 37
tcctgccttc tgtgaggcgt ctatcgagca gtttgct                               37

<210> SEQ ID NO 38
<211> LENGTH: 37
<212> TYPE: DNA
<213> ORGANISM: Artificial sequence
<220> FEATURE:
<223> OTHER INFORMATION: Primer

<400> SEQUENCE: 38
tcctgccttc tgtgagctgt ctatcgagca gtttgct                               37

<210> SEQ ID NO 39
<211> LENGTH: 37
<212> TYPE: DNA
<213> ORGANISM: Artificial sequence
<220> FEATURE:
<223> OTHER INFORMATION: Primer

<400> SEQUENCE: 39
tcctgccttc tgtgaggtgt ctatcgagca gtttgct                               37

<210> SEQ ID NO 40
<211> LENGTH: 43
<212> TYPE: DNA
<213> ORGANISM: Artificial sequence
<220> FEATURE:
<223> OTHER INFORMATION: Primer

<400> SEQUENCE: 40
gctatgcctc actggtctga tcaacctact attagcaagt atg                        43

<210> SEQ ID NO 41
<211> LENGTH: 44
<212> TYPE: DNA
<213> ORGANISM: Artificial sequence
<220> FEATURE:
<223> OTHER INFORMATION: Primer

<400> SEQUENCE: 41
agagttttag tctacgatcc agcggcgcca tgggctagaa gagt                       44
```

```
<210> SEQ ID NO 42
<211> LENGTH: 44
<212> TYPE: DNA
<213> ORGANISM: Artificial sequence
<220> FEATURE:
<223> OTHER INFORMATION: Primer

<400> SEQUENCE: 42
agagttttag tctacgatcc agcgggccca tgggctagaa gagt            44

<210> SEQ ID NO 43
<211> LENGTH: 56
<212> TYPE: DNA
<213> ORGANISM: Artificial sequence
<220> FEATURE:
<223> OTHER INFORMATION: Primer

<400> SEQUENCE: 43
cccgtgcgcg tgctggtgta cgacgctgcg gcggcgtggg cacggcgggt ggcaca     56

<210> SEQ ID NO 44
<211> LENGTH: 18
<212> TYPE: DNA
<213> ORGANISM: Artificial sequence
<220> FEATURE:
<223> OTHER INFORMATION: Primer

<400> SEQUENCE: 44
atggagacca cggtcacc                                          18

<210> SEQ ID NO 45
<211> LENGTH: 29
<212> TYPE: DNA
<213> ORGANISM: Artificial sequence
<220> FEATURE:
<223> OTHER INFORMATION: Primer

<400> SEQUENCE: 45
ttatattgac gaatacttgg tagcgaatt                              29

<210> SEQ ID NO 46
<211> LENGTH: 1401
<212> TYPE: DNA
<213> ORGANISM: Oryza sativa

<400> SEQUENCE: 46
atggggagca tgagcacacc ggcggcgagc gccaacggcg ggcaagtgct cctgttgccg     60
ttcccggcgg cgcagggcca caccaacccg atgctccagt cgggcgccg cctcgcgtac    120
cacggcctcc gccccaccct cgtcaccacg cggtacgtgc tctccaccac gccgccgccg    180
ggggacccct tccgcgtcgc cgccatctcc gacggcttcg acgacgccag cggcatggcc    240
gcgctcccgg accccgggga gtacctccgc accctggagg ctcacggtgc acgcacgctg    300
gcggagctcc tcctctccga ggcgcgcgcg gggcggccgg cgcgcgtgct ggtgtacgac    360
ccgcacctgc cgtgggcgcg ccgcgtggcg cgcgccgccg gcgtggccac cgctgcgttc    420
ctgtcgcagc cgtgcgccgt cgacctcatc tacgggagg tgtgcgcgcg gcggctggcg    480
ctgccggtga cgccgacgga cgcgagaggt ctgtacgcgc ggggtgtgct ggcgtcgag    540
ctggggcccg acgacgtgcc ggccgttcgtt gcggcgccag agttgacacc agccttctgt    600
gagcagtcga tcgagcagtt cgccggactg gaggacgacg acgacgtgct cgtcaactca    660
ttctctgacc tcgagccaaa ggaggcagca tacatggagt cgacatggcg cgcgaagacg    720
```

```
atcggcccgt cattgccttc gttctacctc gacgacggcc ggctgcggtc gaacacagca    780
tacgggttca atctcttcag gagcaccgtg ccatgcatgg aatggctgga caagcaacct    840
cctcgctctg tcgtccttgt gtcgtacggg acagtctcca ccttcgacgt agccaagctg    900
gaggagctcg gcaatggcct ttgcaactcc ggcaagccat tcctttgggt tgtcaggtcc    960
aatgaggagc acaagttatc tgtccaactc cgaaaaaagt gtgagaagag aggactaatt   1020 gttcccttt gcccccagct ggaggtgctt gctcacaagg ccacaggttg tttcttgtcg   1080
cactgtggat ggaactcgac attggaggca attgttaatg gcgtaccgct tgtggcaatg   1140
ccacattggg ctgaccaacc aaccatttca aagtatgtgg agagcttgtg gggcatgggc   1200
gtgcgagtgc agctggacaa gagcggcatc ttacaaggg aagaggtaga gagatgcatc   1260
cgggaggtga tggatggtga caggaaggag gactacagga ggaatgctac aaggttgatg   1320
aagaaagcta aggagtcaat gcaggaagga gggagctctg acaagaatat tgctgaattt   1380
gctgcgaagt attcaaattg a                                              1401
```

<210> SEQ ID NO 47
<211> LENGTH: 47
<212> TYPE: DNA
<213> ORGANISM: Artificial sequence
<220> FEATURE:
<223> OTHER INFORMATION: Primer

<400> SEQUENCE: 47
ggttttggtg tcatacggag tggtttctac ttttgatgtt gctaaac    47

<210> SEQ ID NO 48
<211> LENGTH: 47
<212> TYPE: DNA
<213> ORGANISM: Artificial sequence
<220> FEATURE:
<223> OTHER INFORMATION: Primer

<400> SEQUENCE: 48
ggttttggtg tcatacggaa gcgtttctac ttttgatgtt gctaaac    47

<210> SEQ ID NO 49
<211> LENGTH: 37
<212> TYPE: DNA
<213> ORGANISM: Artificial sequence
<220> FEATURE:
<223> OTHER INFORMATION: Primer

<400> SEQUENCE: 49
tcctgccttc tgtgaggaat ctatcgagca gtttgct    37

<210> SEQ ID NO 50
<211> LENGTH: 40
<212> TYPE: DNA
<213> ORGANISM: Artificial sequence
<220> FEATURE:
<223> OTHER INFORMATION: Primer

<400> SEQUENCE: 50
cctgaattaa ctcctgccca atgtgagcaa tctatcgagc    40

<210> SEQ ID NO 51
<211> LENGTH: 35
<212> TYPE: DNA
<213> ORGANISM: Artificial sequence
<220> FEATURE:

```
<223> OTHER INFORMATION: Primer

<400> SEQUENCE: 51
cagccgcatt tctaagtgcg ccatgtgctg tggac                              35

<210> SEQ ID NO 52
<211> LENGTH: 34
<212> TYPE: DNA
<213> ORGANISM: Artificial sequence
<220> FEATURE:
<223> OTHER INFORMATION: Primer

<400> SEQUENCE: 52
gccttctgtg agcaattgat cgagcagttt gctg                               34

<210> SEQ ID NO 53
<211> LENGTH: 34
<212> TYPE: DNA
<213> ORGANISM: Artificial sequence
<220> FEATURE:
<223> OTHER INFORMATION: Primer

<400> SEQUENCE: 53
gccttctgtg agcaagctat cgagcagttt gctg                               34
```